United States Patent
Ito et al.

(10) Patent No.: US 12,199,280 B2
(45) Date of Patent: Jan. 14, 2025

(54) NON-AQUEOUS SECONDARY BATTERY AND NON-AQUEOUS ELECTROLYTE

(71) Applicant: Asahi Kasei Kabushiki Kaisha, Tokyo (JP)

(72) Inventors: Makoto Ito, Tokyo (JP); Hirokazu Kamine, Tokyo (JP); Naoki Matsuoka, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 415 days.

(21) Appl. No.: 17/632,885

(22) PCT Filed: May 28, 2021

(86) PCT No.: PCT/JP2021/020557
§ 371 (c)(1),
(2) Date: Feb. 4, 2022

(87) PCT Pub. No.: WO2021/241761
PCT Pub. Date: Dec. 2, 2021

(65) Prior Publication Data
US 2022/0293929 A1     Sep. 15, 2022

(30) Foreign Application Priority Data
May 28, 2020  (JP) ................................ 2020-093707
May 29, 2020  (JP) ................................ 2020-094801

(51) Int. Cl.
*H01M 4/525*   (2010.01)
*C07D 213/06*  (2006.01)
(Continued)

(52) U.S. Cl.
CPC .......... *H01M 4/525* (2013.01); *C07D 213/06* (2013.01); *H01M 4/505* (2013.01);
(Continued)

(58) Field of Classification Search
CPC .. H01M 4/525; H01M 4/505; H01M 10/0525; H01M 10/0567; H01M 10/0569;
(Continued)

(56) References Cited

U.S. PATENT DOCUMENTS

| | | | |
|---|---|---|---|
| 9,947,484 B2 * | 4/2018 | Takahashi | .............. H01G 11/64 |
| 2006/0024577 A1 * | 2/2006 | Schwake | ............. H01M 10/052 |
| | | | 429/188 |

(Continued)

FOREIGN PATENT DOCUMENTS

| | | |
|---|---|---|
| CN | 109888372 A | 6/2019 |
| CN | 111129498 A | 5/2020 |

(Continued)

OTHER PUBLICATIONS

Myung et al., "Nickel-Rich Layered Cathode Materials for Automotive Lithium-Ion Batteries: Achievements and Perspectives," ACS Energy Letters, 2: 196-223 (2016).

(Continued)

*Primary Examiner* — Matthew J Merkling
(74) *Attorney, Agent, or Firm* — Morgan, Lewis & Bockius LLP

(57) ABSTRACT

Provided is a non-aqueous secondary battery that includes a positive electrode, a negative electrode, a separator, and a non-aqueous electrolyte. The positive electrode includes $LiNi_xCo_yMn_zO_2$ ($0.7<x<0.9$, $0<y<0.2$, $0<z<0.2$) as a lithium-containing metal oxide, and when the positive electrode before and after cycle testing of the non-aqueous secondary battery is analyzed by powder X-ray diffraction using Cu-Kα radiation, the rate of change of the c-axis lattice constant is 1.0% or less. The non-aqueous electrolyte includes 5-20% by volume of acetonitrile and has an ion conductivity of at least 10 mS/cm and less than 15 mS/cm at 20° C.

20 Claims, 4 Drawing Sheets

(51) Int. Cl.
*H01M 4/02* (2006.01)
*H01M 4/505* (2010.01)
*H01M 10/0525* (2010.01)
*H01M 10/0567* (2010.01)
*H01M 10/0569* (2010.01)

(52) U.S. Cl.
CPC ... *H01M 10/0525* (2013.01); *H01M 10/0567* (2013.01); *H01M 10/0569* (2013.01); *H01M 2004/027* (2013.01); *H01M 2004/028* (2013.01); *H01M 2300/0034* (2013.01)

(58) Field of Classification Search
CPC ..... H01M 2004/027; H01M 2004/028; H01M 2300/0034; C07D 213/06
See application file for complete search history.

(56) References Cited

U.S. PATENT DOCUMENTS

| | | | |
|---|---|---|---|
| 2007/0231705 A1 | 10/2007 | Ohzuku et al. | |
| 2009/0191455 A1* | 7/2009 | Gao | H01M 10/0567 252/182.1 |
| 2011/0039162 A1 | 2/2011 | Maeda | |
| 2012/0316716 A1 | 12/2012 | Odani et al. | |
| 2013/0224535 A1 | 8/2013 | Matsuoka et al. | |
| 2013/0252112 A1* | 9/2013 | Doe | H01M 10/0568 429/328 |
| 2014/0255796 A1 | 9/2014 | Matsuoka et al. | |
| 2015/0372348 A1 | 12/2015 | Buqa et al. | |
| 2016/0164078 A1* | 6/2016 | Hong | H01M 4/622 429/217 |
| 2016/0380263 A1* | 12/2016 | Nakayama | H01M 4/366 429/223 |
| 2017/0033402 A1 | 2/2017 | Kubota et al. | |
| 2017/0062818 A1 | 3/2017 | Ogata et al. | |
| 2017/0170513 A1 | 6/2017 | Sakamoto et al. | |
| 2017/0207453 A1 | 7/2017 | Oda | |
| 2017/0346128 A1 | 11/2017 | Fujii et al. | |
| 2018/0062207 A1 | 3/2018 | Matsuoka et al. | |
| 2019/0006662 A1 | 1/2019 | Amine et al. | |
| 2019/0165417 A1 | 5/2019 | Morita et al. | |
| 2019/0221839 A1 | 7/2019 | Inoue et al. | |
| 2019/0393556 A1 | 12/2019 | Matsuoka et al. | |
| 2020/0091554 A1 | 3/2020 | Matsuoka et al. | |
| 2020/0335782 A1 | 10/2020 | Oh et al. | |
| 2021/0075011 A1 | 3/2021 | Lim et al. | |
| 2021/0167378 A1 | 6/2021 | Koshika et al. | |
| 2021/0194052 A1 | 6/2021 | Oh et al. | |
| 2021/0344046 A1 | 11/2021 | Matsuoka et al. | |
| 2022/0077497 A1* | 3/2022 | Keshavarz | H01M 10/052 |

FOREIGN PATENT DOCUMENTS

| | | |
|---|---|---|
| EP | 2945213 A1 | 11/2015 |
| EP | 3831780 A1 | 6/2021 |
| JP | 2000-207934 A | 7/2000 |
| JP | 2012-099289 A | 5/2012 |
| JP | 2013-016456 A | 1/2013 |
| JP | 2015-065050 A | 4/2015 |
| JP | 2015-176760 A | 10/2015 |
| JP | 2016-207313 A | 12/2016 |
| JP | 2017-0109241 A | 1/2017 |
| JP | 2017-054822 A | 3/2017 |
| JP | 2017-073251 A | 4/2017 |
| JP | 2017-102995 A | 6/2017 |
| JP | 2018-098174 A | 6/2018 |
| JP | 2019-506703 A | 3/2019 |
| JP | 2019-099388 A | 6/2019 |
| JP | 2019-140054 A | 8/2019 |
| JP | 2019-175632 A | 10/2019 |
| JP | 2019-212400 A | 12/2019 |
| KR | 10-2011-0016378 A | 2/2011 |
| KR | 10-2019-0064459 A | 6/2019 |
| WO | 2011/135953 A1 | 11/2011 |
| WO | 2012/057311 A1 | 5/2012 |
| WO | 2013/062056 A1 | 5/2013 |
| WO | 2015/129187 A1 | 9/2015 |
| WO | 2015/156399 A1 | 10/2015 |
| WO | 2015/163139 A1 | 10/2015 |
| WO | 2016/017783 A1 | 2/2016 |
| WO | 2016/103511 A1 | 6/2016 |
| WO | 2016/159108 A1 | 10/2016 |
| WO | 2017/123836 A1 | 7/2017 |
| WO | 2018/169028 A1 | 9/2018 |
| WO | 2018/169029 A1 | 9/2018 |
| WO | 2019/151724 A1 | 8/2019 |
| WO | 2020/054863 A1 | 3/2020 |

OTHER PUBLICATIONS

Noh et al., "Comparison of the structural and electrochemical properties of layered Li[NixCoyMnz]O2 (x=1/3, 0.5, 0.6, 0.7, 0.8 and 0.85) cathode material for lithium-ion batteries," Journal of Power Sources, 233: 121-130 (2013).
Jung et al., "Chemical versus Electrochemical Electrolyte Oxidation on NMC111, NMC622, NMC811, LNMO, and Conductive Carbon," Journal of Physical Chemistry Letters, 8: 4820-4825 (2017).
International Search Report issued in corresponding International Patent Application No. PCT/JP2021/020557 dated Aug. 17, 2021.
Supplementary European Search Report issued in related European Patent Application No. 21813063.1 dated Oct. 7, 2022.
Schipper et al., "From Surface ZrO2 Coating to Bulk Zr Doping by High Temperature Annealing of Nickel-Rich Lithiated Oxides and Their Enhanced Electrochemical Performance in Lithium Ion Batteries," Advanced Energy Materials, 8 (4): 1701682 (2018).
Ho et al., "Crucial role of thioacetamide for ZrO2 coating on the fragile surface of Ni-rich layered cathode in lithium ion batteries," Journal of Power Sources, 450 (2020).
International Preliminary Report on Patentability and Written Opinion issued in corresponding International Patent Application No. PCT/JP2021/020557 dated Nov. 17, 2022.
Partial European Search Report issued in European Patent Application No. 24185762.2 dated Nov. 21, 2024.

* cited by examiner

NON-AQUEOUS SECONDARY BATTERY AND NON-AQUEOUS ELECTROLYTE

FIELD

The present invention relates to a non-aqueous secondary battery and a non-aqueous electrolyte solution.

BACKGROUND

Non-aqueous secondary batteries including lithium ion batteries are mainly characterized by having a lightweight, a high energy and a long life, and are widely used as power sources for various portable electronic devices. In recent years, for the purpose of increasing the capacity, lithium-containing metal oxides having a high nickel ratio are used in positive electrode active materials. However, there remains a problem that such non-aqueous secondary batteries have poor long-term durability although they can be provided with an increased capacity.

In view of this problem, studies have been carried out on, for example, non-aqueous electrolyte solutions, additives, and non-aqueous secondary battery electrode materials containing the same (e.g., PTL 1).

According to PTL 2, it is reported that an increase in the positive electrode resistance during charging and discharging is controlled and the cycle characteristics are improved by controlling the crystallite size of a positive electrode active material and adding fluoroethylene carbonate to a non-aqueous electrolyte solution.

According to PTL 3, it is reported that expansion and contraction of a positive electrode during charging and discharging are reduced and the cycle characteristics at a high voltage are improved by defining the c/a axis ratio of the positive electrode to be in a prescribed range.

According to PTL 4, it is reported that excellent cycle characteristics and rate characteristics as well as a high energy density are obtained by defining the crystal size and the specific surface area of a positive electrode to be in prescribed ranges.

Further, in association with the expansion of the large-scale energy storage industry centered around electric vehicles in recent years, there is a strong demand for a higher energy density in non-aqueous secondary batteries. With regard to non-aqueous solvents of lithium ion batteries, nitrile-based solvents having an excellent balance between the viscosity and the dielectric constant have been proposed as high-ionic-conductivity electrolyte solutions. Thereamong, acetonitrile has a high potential.

For example, PTL 5 discloses a non-aqueous secondary battery that is operated with high-capacity electrodes using a non-aqueous electrolyte solution containing acetonitrile as a non-aqueous solvent, and reports that a solid electrolyte interface (SEI) is strengthened by adding plural kinds of electrode protection additives.

PTL 6 reports that the use of a specific organic lithium salt strengthens an SEI and inhibits decomposition of an electrolyte solution. Further, PTL 7 describes the use of an acetonitrile-containing non-aqueous electrolyte solution.

In NPL 1, it is reported that a higher energy density is obtained as the Ni content ratio is increased in a layered rock salt type positive electrode active material.

However, in non-aqueous secondary batteries, there is a problem of having to attain both an improved energy density and a satisfactory long-term durability. For example, NPL 2 describes that a higher Ni ratio in a positive electrode active material leads to a further progress of deterioration at a low voltage. NPL 3 reports a mechanism which induces decomposition of a lithium salt triggered by decomposition of a high-dielectric solvent.

CITATION LIST

Patent Literature

[PTL 1] WO2018/169028
[PTL 2] WO2015/129187
[PTL 3] WO2011/135953
[PTL 4] Japanese Unexamined Patent Publication (Kokai) No. 2018-98174
[PTL 5] WO2013/062056
[PTL 6] WO2012/057311
[PTL 7] WO2016/159108
[PTL 8] Japanese Unexamined Patent Publication (Kokai) No. 2017-10924
[PTL 9] Japanese Unexamined Patent Publication (Kokai) No. 2016-207313

Non Patent Literature

[NPL 1] ACS Energy Lett., 2, 196-223 (2017)
[NPL 2] J. Power Sources, 233, 121-130 (2013)
[NPL 3] J. Phys. Chem. Lett., 8, 4820-4825 (2017)

SUMMARY

Technical Problem

As a factor that causes deterioration of a non-aqueous secondary battery containing a positive electrode active material having a Ni ratio of higher than 0.5 in a lithium-containing metal oxide, it is known that expansion and contraction of the positive electrode active material due to charging and discharging induce cracking at the primary particle boundaries of the positive electrode active material, causing various deterioration. Further, the progress of deterioration causes spinel transition, and this leads to a problem that, for example, the crystal structure can no longer be maintained and the cycle performance is markedly impaired.

Particularly, it was confirmed that, when a non-aqueous electrolyte solution having a high ionic conductivity as described in PTL 1 was applied to a non-aqueous secondary battery containing a positive electrode active material having a high nickel ratio, lithium was preferentially extracted from the positive electrode active material on the electrode surface, and this caused a marked progress of cracking of the positive electrode active material on the electrode surface, resulting in a sudden capacity drop in the middle of a cycle. FIGS. 1 and 2 of the present specification provide cross-sectional SEM images of positive electrodes, which were taken after producing non-aqueous secondary batteries using non-aqueous electrolyte solutions having different ionic conductivities and carrying out 100 cycles under a 50° C. environment after initial charging and discharging. It is seen that a larger number of cracks of the positive electrode active material were generated on the positive electrode surface with the use of the non-aqueous electrolyte solution having a higher ionic conductivity.

Further, even with the crystallite size, the specific surface area, and/or the c/a axis ratio being controlled in prescribed ranges as described in PTLs 2 to 4, the positive electrode active material having a high Ni ratio was cracked, and favorable cycle performance was not sufficiently obtained.

These non-aqueous secondary batteries aimed at an increase in the energy density have not been put into full-scale practical use since they are inferior to the existing non-aqueous secondary batteries in terms of long-term durability and high-temperature durability. Non-aqueous electrolyte solutions and electrodes are both required to be durable under a more severe environment.

PTL 8 reports a non-aqueous electrolyte solution in which a dinitrile compound and a fluorosulfonylimide compound are used in combination. However, a non-aqueous secondary battery containing this non-aqueous electrolyte solution has a low capacity, and no description is offered with regard to the long-term durability and the high-temperature durability. In addition, the non-aqueous electrolyte solution described in PTL 8 has a low content of non-aqueous solvent other than the dinitrile compound and is, therefore, presumed to have a high viscosity and poor output characteristics.

PTL 9 reports a non-aqueous secondary battery in which a titanium-containing oxide, a compound containing amide anion, and a nitrile-based compound are used as a negative electrode, a lithium salt, and a non-aqueous solvent, respectively; however, since the concentration of the lithium salt is high, it is presumed that the electrolyte solution has a high viscosity, a low ionic conductivity, and a poor wettability to the electrodes. In addition, since the titanium-containing oxide used in the negative electrode descried in PTL 9 has a high operating potential, the battery can provide a low power capacity.

Moreover, particularly, the use of an acetonitrile-containing non-aqueous electrolyte solution in combination with a positive electrode that contains a lithium-nickel composite metal oxide having a high Ni content ratio as a positive electrode active material in a non-aqueous secondary battery has a problem of greatly impairing the high-temperature cycle performance.

In PTLs 5 to 7, reports are made on lithium ion secondary batteries using an acetonitrile-containing non-aqueous electrolyte solution; however, the long-term durability and the high-temperature durability were evaluated using a positive electrode active material having a low Ni ratio, and problems caused by the use of a positive electrode active material having a high Ni ratio are not indicated.

The present invention was made in view of the above-described problems. A first object of the present invention is to provide a non-aqueous secondary battery in which, despite a positive electrode active material having a high nickel ratio is used and acetonitrile is contained in a non-aqueous electrolyte solution, various deterioration of the positive electrode active material during charging and discharging under a high temperature environment can be inhibited. A second object of the present invention is to provide a non-aqueous electrolyte solution and a non-aqueous secondary battery which can exert a high capacity as well as excellent cycle characteristics and high-temperature durability even when the non-aqueous electrolyte solution contains acetonitrile.

Solution to Problem

The present inventors intensively studied to solve the above-described problems and consequently discovered that the problems can be solved by using a non-aqueous electrolyte solution or non-aqueous secondary battery that has the below-described constitution, thereby completing the present invention. In other words, the present invention encompasses the followings.

<1> A non-aqueous secondary battery, including:

a positive electrode that contains a positive electrode active material;

a negative electrode that contains a negative electrode active material;

a separator; and a non-aqueous electrolyte solution, wherein the positive electrode active material contains:

a lithium-containing metal oxide represented by the following Formula (a):

  (a)

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0<t<0.3$, $0.7\leq q+r+s+t\leq 1.2$, and $1.8<u<2.2$ are satisfied; and p is a value determined by a charge-discharge state of the battery}, or a positive electrode active material composite formed of:

a core particle containing a lithium-containing metal oxide represented by the following Formula (b):

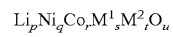  (b)

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0\leq t<0.3$, $0.7\leq q+r+s+t\leq 1.2$, and $1.8<u<2.2$ are satisfied; and p is a value determined by a charge-discharge state of the battery}; and a coating layer that exists on at least one portion of a surface of the core particle and contains at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd, in the step 1 of constant-current charging the non-aqueous secondary battery to a battery voltage of 4.2 V under a 25° C. environment and subsequently constant-voltage charging the battery to a current value of 0.025 C followed by discharging to 3 V at a constant current, and the step 2 of, after the step 1, carrying out 100 cycles each of which consists of constant-current charging the non-aqueous secondary battery to a battery voltage of 4.2 V under a 50° C. environment and subsequently constant-voltage charging the battery to a current value of 0.025 C followed by discharging to 3 V at a constant current, when a c-axis lattice constant determined by an analysis of the positive electrode of the non-aqueous secondary battery based on powder X-ray diffraction using Cu-Kα radiation before the step 1 is defined as c1, while a c-axis lattice constant determined by an analysis of the positive electrode of the non-aqueous secondary battery based on powder X-ray diffraction using Cu-Kα radiation after constant-current discharging of the battery to a battery voltage of 2.5 V under a 25° C.

environment following the step 2 is defined as c2, a rate of change represented by the following equation:

$$\{(c2/c1)-1\}\times 100$$

is 1.0% or lower, the non-aqueous electrolyte solution contains acetonitrile in an amount of 5 to 20% by volume with respect to a total amount of a non-aqueous solvent, and the non-aqueous electrolyte solution has an ionic conductivity of 10 mS/cm or higher and lower than 15 mS/cm at 20° C.

<2> The non-aqueous secondary battery according to <1>, wherein the lithium-containing metal oxide further satisfies $0.7<q<1$, $0<r<0.2$, and $0<s<0.2$ in Formula (a) or (b).

<3> The non-aqueous secondary battery according to <1> or <2>, wherein the coating layer contains an oxide of at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd.

<4> The non-aqueous secondary battery according to <3>, wherein the coating layer contains zirconium (Zr) oxide.

<5> The non-aqueous secondary battery according to any one of <1> to <4>, wherein $M^2$ in Formula (a) or (b) contains Zr.

<6> A non-aqueous secondary battery, including:

a positive electrode that contains a positive electrode active material;

a negative electrode that contains a negative electrode active material;

a separator; and a non-aqueous electrolyte solution, wherein the positive electrode contains a lithium-containing metal oxide, the lithium-containing metal oxide is represented by the following Formula (c):

$$LiNi_xCo_yMn_zO_2 \qquad (c)$$

{wherein, $0.5<x<1$, $0<y<0.3$, and $0<z<0.3$}, in the step 1 of constant-current charging the non-aqueous secondary battery to a battery voltage of 4.2 V under a 25° C. environment and subsequently constant-voltage charging the battery to a current value of 0.025 C followed by discharging to 3 V at a constant current, and the step 2 of, after the step 1, carrying out 100 cycles each of which consists of constant-current charging the non-aqueous secondary battery to a battery voltage of 4.2 V under a 50° C. environment and subsequently constant-voltage charging the battery to a current value of 0.025 C followed by discharging to 3 V at a constant current, when a c-axis lattice constant determined by an analysis of the positive electrode of the non-aqueous secondary battery based on powder X-ray diffraction using Cu-Kα radiation before the step 1 is defined as c1, while a c-axis lattice constant determined by an analysis of the positive electrode of the non-aqueous secondary battery based on powder X-ray diffraction using Cu-Kα radiation after constant-current discharging of the battery to a battery voltage of 2.5 V under a 25° C. environment following the step 2 is defined as c2, a rate of change represented by the following equation:

$$\{(c2/c1)-1\}\times 100$$

is 1.0% or lower, the non-aqueous electrolyte solution contains acetonitrile in an amount of 5 to 20% by volume with respect to a total amount of a non-aqueous solvent, and the non-aqueous electrolyte solution has an ionic conductivity of 10 mS/cm or higher and lower than 15 mS/cm at 20° C.

<7> The non-aqueous secondary battery according to <6>, wherein the lithium-containing metal oxide further satisfies $0.7<x<0.9$, $0<y<0.2$, and $0<z<0.2$ in Formula (c).

<8> The non-aqueous secondary battery according to any one of <1> to <7>, wherein the c1 is a c-axis lattice constant determined by an analysis of the positive electrode based on powder X-ray diffraction using Cu-Kα radiation before assembly of the non-aqueous secondary battery.

<9> The non-aqueous secondary battery according to any one of <1> to <8>, wherein the rate of change in the c-axis is 0.6% or lower.

<10> The non-aqueous secondary battery according to any one of <1> to <9>, wherein the non-aqueous electrolyte solution contains no acid anhydride.

<11> The non-aqueous secondary battery according to any one of <1> to <10>, wherein the non-aqueous electrolyte solution further contains an imide salt.

<12> The non-aqueous secondary battery according to any one of <1> to <11>, wherein the non-aqueous electrolyte solution further contains a dinitrile compound represented by the following Formula (1):

[Chem. 1]

$$NC-R-CN \qquad (1)$$

{wherein, R represents a straight-chain or branched divalent aliphatic alkyl group having 1 to 12 carbon atoms and optionally containing oxygen atoms}.

<13> The non-aqueous secondary battery according to <12>, wherein the dinitrile compound is at least one compound selected from the group consisting of succinonitrile and methylsuccinonitrile.

<14> The non-aqueous secondary battery according to <12> or <13>, wherein the content of the dinitrile compound is 0.01 to 25% by weight with respect to the whole non-aqueous electrolyte solution.

<15> The non-aqueous secondary battery according to any one of <1> to <14>, wherein the non-aqueous electrolyte solution contains a compound represented by the following Formula (2):

[Chem. 2]

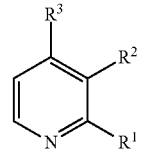

(2)

{wherein, substituents represented by $R^1$, $R^2$, and $R^3$ each independently represent a hydrogen atom, an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, a phenyl group, a cyclohexyl group, a nitrile group, a nitro group, an amino group, an N,N'-dimethylamino group, or an N,N'-diethylamino group; and at least two of the substituents are hydrogen atoms}.

<16> The non-aqueous secondary battery according to <15>, wherein the compound represented by Formula (2) is at least one compound selected from the group consisting of pyridine and 4-(tert-butyl)pyridine.

<17> The non-aqueous secondary battery according to <15> or <16>, wherein the content of the compound represented by Formula (2) is 0.01 to 10% by weight with respect to the whole non-aqueous electrolyte solution.

<18> The non-aqueous secondary battery according to any one of <1> to <17>, wherein the $FSO_3$ anion content in the non-aqueous electrolyte solution is 100 ppm or less with respect to the non-aqueous electrolyte solution.

<19> The non-aqueous secondary battery according to any one of <1> to <18>, wherein the c-axis lattice constant c1 is 14.3 Å or less.

<20> The non-aqueous secondary battery according to any one of <1> to <19>, wherein the c-axis lattice constant c2 is 14.3 Å or less.

<21> The non-aqueous secondary battery according to any one of <1> to <20>, wherein the amount of propionitrile contained in the non-aqueous electrolyte solution is less than 1.0 ppm with respect to a total amount of the non-aqueous electrolyte solution.

<22> A non-aqueous electrolyte solution, containing:
an acetonitrile-containing non-aqueous solvent;
a dinitrile compound represented by the following Formula (1):

[Chem. 3]

NC—R—CN    (1)

{wherein, R represents a straight-chain or branched divalent aliphatic alkyl group having 1 to 12 carbon atoms and optionally containing oxygen atoms}; and
a lithium salt containing $LiPF_6$ and LiFSI,
wherein
the non-aqueous electrolyte solution contains acetonitrile in an amount of 10 to 70% by volume with respect to a total amount of the non-aqueous solvent,
the content of the dinitrile compound is 25% by weight or less with respect to a total amount of the non-aqueous electrolyte solution,
the content of the dinitrile compound is 0.10 or higher in terms of molar ratio with respect to acetonitrile, and
the content of $LiPF_6$ and that of an imide salt containing LiFSI have a relationship of $0<LiPF_6$ imide salt, in terms of molar concentration.

<23> The non-aqueous electrolyte solution according to <22>, wherein the content of the non-aqueous solvent is more than 70% by volume and/or more than 70% by weight, with respect to a total amount of the non-aqueous solvent and the dinitrile compound.

<24> The non-aqueous electrolyte solution according to <22> or <23>, wherein the content of the dinitrile compound is 1% by weight or more with respect to a total amount of the non-aqueous electrolyte solution.

<25> A non-aqueous secondary battery, including:
a positive electrode that includes a positive electrode active material layer on one or both sides of a positive electrode current collector; and
the non-aqueous electrolyte solution according to any one of <22> to <24>, wherein the positive electrode active material contains a lithium-containing metal oxide represented by the following Formula (d):

$Li_pNi_qCo_rM^1_sM^2_tO_u$    (d)

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.4<q<1$, $0<r<0.4$, $0<s<0.4$, $0\leq t<0.3$, $0.7\leq q+r+s+t\leq 1.2$, and $1.8<u<2.2$ are satisfied; and p is a value determined by a charge-discharge state of the battery}.

<26> The non-aqueous secondary battery according to <25>, wherein the lithium-containing metal oxide further satisfies $0.7<q<1$, $0<r<0.2$, and $0<s<0.2$ in Formula (d).

Advantageous Effects of Invention

According to the present invention, first, a non-aqueous secondary battery in which, despite a positive electrode active material having a high nickel ratio is used and acetonitrile is contained in a non-aqueous electrolyte solution, various deterioration of the positive electrode active material during charging and discharging under a high temperature environment can be inhibited, can be provided. Secondly, a non-aqueous secondary battery which can exert a high capacity as well as excellent cycle characteristics and high-temperature durability even when its non-aqueous electrolyte solution contains acetonitrile.

DESCRIPTION OF EMBODIMENTS

Modes for carrying out the present invention (hereinafter, simply referred to as "embodiments") will now be described in detail. The present invention is not limited to the below-described embodiments, and various modifications can be made without departing from the gist of the present invention. In the present specification, those numerical ranges that are expressed with "to" include the numerical values stated before and after "to".

First Embodiment

The non-aqueous electrolyte solution according to a first embodiment, and a non-aqueous secondary battery containing the same will now be described. According to the non-aqueous secondary battery of the present embodiment, in the non-aqueous secondary battery that includes a non-aqueous electrolyte solution, not only cracking of a positive electrode active material during charge-discharge cycles under a high temperature environment can be inhibited by controlling the rate of change in the lattice constant of a positive electrode before and after energization, which is determined based on powder X-ray diffraction, to be 1.0% or lower, but also the amount of lithium extraction from the positive electrode is made uniform and cracking of the positive electrode active material is inhibited by controlling the ionic conductivity of the non-aqueous electrolyte solution containing acetonitrile to be in a prescribed range, as a result of which various deterioration phenomena under a high temperature environment can be inhibited.

[Non-Aqueous Secondary Battery]

The non-aqueous electrolyte solution of the present embodiment can be used in a non-aqueous secondary battery. The non-aqueous secondary battery of the present embodiment is not particularly limited in terms of its negative electrode, positive electrode, separator, and exterior.

Further, examples of the non-aqueous secondary battery of the present embodiment include, but not limited to, lithium ion batteries that are provided with: a positive electrode that contains a positive electrode material capable of occluding and releasing lithium ions as a positive electrode active material; and a negative electrode that contains a negative electrode material capable of occluding and releasing lithium ions as a negative electrode active material, and/or metallic lithium.

Figure 3:
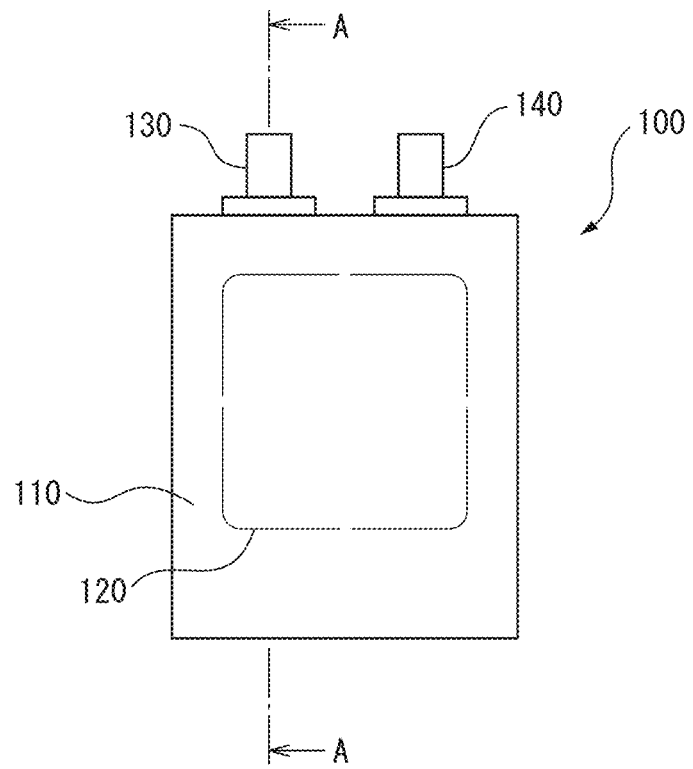
FIG. 3 is a plan view schematically illustrating one example of a non-aqueous secondary battery according to one embodiment of the present invention.
Figure 4:
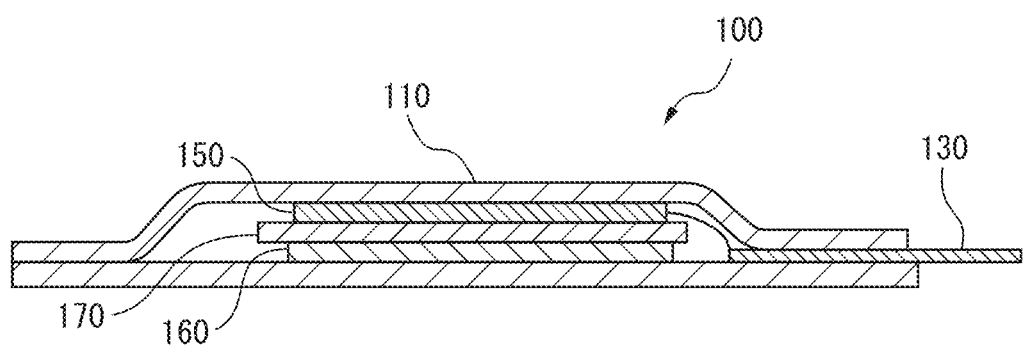
FIG. 4 is a cross-sectional view of the non-aqueous secondary battery illustrated in FIG. 3, taken along a line A-A.

Specifically, the non-aqueous secondary battery of the present embodiment may be a non-aqueous secondary battery illustrated in FIGS. 3 and 4. FIG. 3 is a plan view that schematically illustrates a non-aqueous secondary battery, and FIG. 4 is a cross-sectional view taken along a line A-A of FIG. 3.

A non-aqueous secondary battery 100 illustrated in FIGS. 3 and 4 is formed of a pouch-type cell. The non-aqueous secondary battery 100 includes a laminated electrode structure, which is formed by laminating a positive electrode 150 and a negative electrode 160 via a separator 170, and a non-aqueous electrolyte solution (not illustrated) in a space 120 of a battery exterior 110 composed of a pair of aluminum laminate films. The battery exterior 110 is sealed by heat-fusing the outer peripheries of upper and lower aluminum laminate films. A layered product in which the positive electrode 150, the separator 170 and the negative electrode 160 are sequentially laminated is impregnated with the non-aqueous electrolyte solution. It is noted here that, in FIG. 4, in order to avoid making the drawing complicated, the individual layers constituting the battery exterior 110 and the individual layers of the positive electrode 150 and the negative electrode 160 are not illustrated in a distinguishable manner.

The aluminum laminate films constituting the battery exterior 110 are each preferably an aluminum foil coated with a polyolefin-based resin on both sides.

The positive electrode 150 is connected to a positive electrode lead 130 inside the non-aqueous secondary battery 100. The negative electrode 160 is also connected to a negative electrode lead 140 inside the non-aqueous secondary battery 100, although this is not illustrated. In addition, the positive electrode lead 130 and the negative electrode lead 140 are each drawn to the outside of the battery exterior 110 on one end such that they can be connected to an external device or the like, and their ionomer portions are heat-fused together with one side of the battery exterior 110.

The non-aqueous secondary battery 100 illustrated in FIGS. 3 and 4 has a laminated electrode structure having one each of the positive electrode 150 and the negative electrode 160; however, depending on the capacity design, the number of laminated positive electrodes 150 and that of laminated negative electrodes 160 can be increased as appropriate. When the laminated electrode structure has plural positive electrodes 150 and plural negative electrodes 160, tabs of the electrodes of the same kind may be joined together by welding or like, and the joined tabs may be connected to a single lead by welding or the like and drawn to the outside of the battery. The tabs of the electrodes of the same kind can take, for example, a mode of being composed of an exposed part of a current collector, or a mode of being composed of a metal piece welded to an exposed part of a current collector.

The positive electrode 150 is constituted by a positive electrode active material layer produced from a positive electrode mixture, and a positive electrode current collector. The negative electrode 160 is constituted by a negative electrode active material layer produced from a negative electrode mixture, and a negative electrode current collector. The positive electrode 150 and the negative electrode 160 are arranged such that the positive electrode active material layer and the negative electrode active material layer face each other across the separator 170.

For these members, any material that is included in a conventional lithium ion battery can be used as long as it satisfies the requirements of the present embodiment. The members of the non-aqueous secondary battery will now be each described in more detail.

[Positive Electrode]

In the non-aqueous secondary battery of the present embodiment, the positive electrode has a positive electrode active material layer on one or both sides of a positive electrode current collector.

<Positive Electrode Active Material Layer>

The positive electrode active material layer contains a positive electrode active material, and preferably further contains a conductive aid and a binder as required.

(Positive Electrode Active Material)

The positive electrode active material layer preferably contains a material capable of occluding and releasing lithium ions as the positive electrode active material. When such a material is used, a high voltage and a high energy density tend to be obtained, which is preferred.

The positive electrode active material is preferably a material that contains a lithium-containing metal oxide represented by the following Formula (a):

$$Li_pNi_qCo_rM^1_sM^2_tO_u \qquad (a)$$

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0<t<0.3$, $0.7 \leq q+r+s+t \leq 1.2$, and $1.8<u<2.2$ are satisfied; and p is a value determined by a charge-discharge state of the battery}, or a positive electrode active material composite formed by: a core particle containing a lithium-containing metal oxide represented by the following Formula (b):

$$Li_pNi_qCo_rM^1_sM^2_tO_u \qquad (b)$$

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0\leq t<0.3$, $0.7\leq q+r+s+t\leq 1.2$, and $1.8<u<2.2$ are satisfied; and p is a value determined by a charge-discharge state of the battery}; and a coating layer that exists on at least a portion of the surface of the core particle and contains at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd.

In another mode, the positive electrode contains a lithium-containing metal oxide, and the lithium-containing metal oxide is preferably represented by the following Formula (c):

$$LiNi_xCo_yMn_zO_2 \qquad (c)$$

{wherein, $0.5<x<1$, $0<y<0.3$, and $0<z<0.3$}.

The above-described compound of Formula (c) is a positive electrode active material.

Examples of the positive electrode active material include:

lithium nickel oxides typified by $LiNiO_2$;

lithium-containing composite metal oxides represented by $Li_zMO_2$ (wherein, M contains at least one transition metal element selected from the group consisting of Ni, Mn, and Co and represents two or more metal elements selected from the group consisting of Ni, Mn, Co, Al, and Mg; and z represents a number of larger than 0.9 but smaller than 1.2), which are typified by $LiNi_{0.6}Co_{0.2}Mn_{0.2}O_2$, $LiNi_{0.75}Co_{0.15}Mn_{0.15}O_2$, $LiNi_{0.8}Co_{0.1}Mn_{0.1}O_2$, $LiNi_{0.85}Co_{0.075}Mn_{0.075}O_2$, $LiNi_{0.8}Co_{0.15}Al_{0.05}O_2$, $LiNi_{0.81}Co_{0.1}Al_{0.09}O_2$, and $LiNi_{0.85}Co_{0.1}Al_{0.05}O_2$;

the above-described lithium-containing composite metal oxides to which at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd is added; and materials that contain a core particle containing any of the above-described lithium-containing composite metal oxides, and a coating layer that exists on at least a portion of the surface of the core particle and contains at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd.

Particularly, when the lithium-containing metal oxide represented by Formula (a) or (b) has a high Ni content ratio q and satisfies $0.7<q<1$, $0<r<0.2$ and $0<s<0.2$, a reduction in the amount of rare metal Co to be used and an increase in the energy density are both achieved, which is preferred. For the same reason, Formula (c) preferably satisfies $0.7<x<0.9$, $0<y<0.2$, and $0<z<0.2$.

On the other hand, as the Ni content ratio in the lithium-containing metal oxide increases, cycle deterioration tends to progress under a high temperature environment.

The present inventors analyzed positive electrodes based on powder X-ray diffraction before and after 100 cycles of charging and discharging under a high temperature environment, and found that those positive electrodes with further deterioration tended to have a larger c-axis lattice constant. Therefore, with respect to the c-axis lattice constant of the positive electrode prior to the step of carrying out 100 cycles of charging and discharging under a high temperature environment, the rate of change in the c-axis lattice constant of the positive electrode after the 100 cycles is preferably 1.0% or lower, more preferably 0.8% or lower, still more preferably 0.6% or lower. When the rate of change in the c-axis lattice constant of the positive electrode is in this range, cracking of the positive electrode active material during charge-discharge cycles under a high temperature environment can be inhibited, so that the desired cycle characteristics can be satisfied.

Examples of a method of controlling the rate of change in the c-axis lattice constant of the positive electrode to be in a specific range include the use of a specific positive electrode active material, and the use of a specific acetonitrile-containing non-aqueous electrolyte solution. Specifically, the "specific positive electrode active material" is the above-described lithium-containing metal oxide represented by Formula (a) or (c), or a positive electrode active material composite composed of a coating layer and a core particle containing the lithium-containing metal oxide represented by Formula (b), preferably the above-described lithium-containing metal oxide represented by Formula (a) or the above-described positive electrode active material composite. Further, the "acetonitrile-containing non-aqueous electrolyte solution" is specifically an electrolyte solution that contains acetonitrile in an amount of 5 to 20% by volume with respect to a total amount of a non-aqueous solvent, and has an ionic conductivity of 10 mS/cm or higher but lower than 15 mS/cm at 20° C. The above-described rate of change can be controlled by adding a compound that stabilizes the crystal structure of the positive electrode, which compound is typified by dinitrile compounds and nitrogen-containing cyclic compounds.

More specifically, when the c-axis lattice constant of the positive electrode of the non-aqueous secondary battery according to the first embodiment that is analyzed based on powder X-ray diffraction using Cu-Kα radiation is defined as "c1", and the c-axis lattice constant of the positive electrode of the non-aqueous secondary battery according to the present embodiment that is analyzed based on powder X-ray diffraction using Cu-Kα radiation after carrying out an initial charge-discharge treatment of the non-aqueous secondary battery under a 25° C. environment (hereinafter, also referred to as "step 1") and subsequently carrying out 100 cycles (hereinafter, also referred to as "step 2"), each cycle of which consists of constant-current charging to a battery voltage of 4.2 V under a 50° C. environment, constant-voltage charging to a current value of 0.025 C, and subsequent discharging to 3 V at a constant current (each cycle may be hereinafter referred to as "energization" process) followed by constant-current discharging to a battery voltage of 2.5 V under a 25° C. environment, is defined as "c2", the rate of change represented by the following Equation 1 is preferably 1.0% or lower, more preferably 0.8% or lower, still more preferably 0.6% or lower:

$$\{(c2/c1)-1\}\times 100 \qquad \text{Equation 1.}$$

From the above-described standpoints, it is also preferred that the c-axis lattice constant c1 of the positive electrode prior to the above-described energization process and the c-axis lattice constant c2 of the positive electrode after 100 cycles of the energization process be both 14.3 Å or less ($14.3\times 10^{-10}$ m or less). Powder X-ray diffractometry of the positive electrode using Cu-Kα radiation will be described in detail below in the section of Examples.

The initial charge-discharge treatment (step 1) is carried out under a 25° C. environment, and consists of constant-current charging to a battery voltage of 4.2 V under a 25° C. environment, constant-voltage charging to a current value of 0.025 C, and subsequent discharging to 3 V at a constant current. From the standpoint of forming a stable and strong SEI on the electrode surface, the constant-current charging and the constant-current discharging in the initial charge-discharge treatment (step 1) are carried out at preferably 0.001 to 0.3 C, more preferably 0.002 to 0.25 C, still more preferably 0.003 to 0.2 C. As for a method of the constant-current charging in the initial charge-discharge treatment (step 1), from the standpoint of forming a stable and strong SEI on the electrode surface, it is possible to perform constant-current charging with a certain current density up to a specific battery voltage lower than 4.2 V and subsequently perform constant-current charging with a different current density up to a battery voltage of 4.2 V. Further, from the standpoint of forming a stable and strong SEI on the electrode surface, the initial charge-discharge treatment (step 1) may be repeated plural times. The number of the repeated treatments is preferably 1 to 5, more preferably 1 to 4, still more preferably 1 to 3.

The step 2 consists of carrying out 100 cycles, each of which includes constant-current charging to a battery voltage of 4.2 V under a 50° C. environment, constant-voltage charging to a current value of 0.025 C, and subsequent discharging to 3 V at a constant current (each cycle may be hereinafter referred to as "energization" process). The constant-current charging and the constant-current discharging in the step 2 are carried out at preferably 0.1 to 2 C, more preferably 0.5 to 1.75 C, still more preferably 1.0 to 1.5 C.

After the step 2, the non-aqueous secondary battery is constant-current discharged to a battery voltage of 2.5 V under a 25° C. environment and then disassembled in an inert atmosphere to take out the positive electrode, which is subsequently washed with an organic solvent such as diethyl carbonate, dried, and then measured using a powder X-ray diffractometer. The constant-current discharging immediately before the disassembly is carried out at preferably 0.01 to 1 C, more preferably 0.05 to 0.5 C, still more preferably 0.1 to 0.25 C. The c-axis lattice constant of this positive electrode is defined as "c2".

When the non-aqueous secondary battery prior to assembly is measured, the c-axis lattice constant of the positive electrode prior to the assembly of the non-aqueous secondary battery, which is analyzed based on powder X-ray diffraction using Cu-Kα radiation, is defined as "c1".

When the non-aqeuous secondary battery after assembly is measured, the non-aqueous secondary battery is constant-current discharged to a battery voltage of 2.5 V or lower under a 25° C. environment and then disassembled in an inert atmosphere to take out the positive electrode, which is subsequently washed with an organic solvent such as diethyl carbonate, dried, and then measured using a powder X-ray diffractometer. The constant-current discharging immediately before the disassembly is carried out at preferably 0.01 to 1 C, more preferably 0.05 to 0.5 C, still more preferably 0.1 to 0.25 C. The c-axis lattice constant of this positive electrode is defined as "c1". Further, when the non-aqeuous secondary battery after assembly is measured, two of such non-aqueous secondary batteries are prepared for the measurement. One of the non-aqueous secondary batteries is disassembled before carrying out the step 1 to measure the c1, while the other is disassembled after carrying out both of the steps 1 and 2 to measure the c2.

The positive electrode active material used in the first embodiment preferably contains a lithium-containing metal oxide that contains, as a doping element, at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd, or a core particle containing a lithium-containing metal oxide, and a coating layer that exists on at least a portion of the surface of the core particle and contains, as a coating element, at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd.

By incorporating a doping element into the positive electrode active material, the crystal structure of the positive electrode active material is stabilized, and spinel transition occurring with the progress of deterioration caused by non-uniform lithium extraction is inhibited. By these effects, the rate of change in the c-axis lattice constant is reduced, and cracking of the positive electrode active material is inhibited. As a result, various deterioration phenomena under a high temperature environment can be inhibited.

As the doping element, from the standpoint of strongly stabilizing the crystal structure of the positive electrode active material, Zr, W, Ti, Mg, Ta, and Nb are preferred, Zr and Ti are more preferred, and Zr is still more preferred. From the same standpoint, $M^2$ in Formula (a) or (b) preferably contains Zr.

When the positive electrode active material contains a coating layer, not only the diffusion rate of the acetonitrile-containing non-aqueous electrolyte solution into deep parts of the positive electrode active material particles is reduced and lithium extraction in the deep parts of the positive electrode active material particles is thereby inhibited, but also the crystal structure of the positive electrode active material is stabilized and spinel transition occurring with the progress of deterioration caused by non-uniform lithium extraction is inhibited. By these effects, the rate of change in the c-axis lattice constant is reduced, and cracking of the positive electrode active material is inhibited. As a result, various deterioration phenomena under a high temperature environment can be inhibited.

As the coating element contained in the coating layer, from the standpoint of strongly stabilizing the crystal structure of the positive electrode active material, Zr, W, Al, Ti, Mg, Ta, and Nb are preferred, Zr, Al, and Ti are more preferred, and Zr is still more preferred.

Further, from the standpoint of strongly stabilizing the crystal structure of the positive electrode active material, the coating layer contains preferably an oxide of at least one element selected from the group consisting of Zr, W, Al, Ti, Mg, Ta, and Nb, more preferably an oxide of Zr, Al, and/or Ti, still more preferably zirconium (Zr) oxide (e.g., zirconia). It was revealed that, when Zr oxide is used as the coating element, the rate of change in the c-axis lattice constant can be markedly reduced and various deterioration phenomena under a high temperature environment can be markedly inhibited, as compared to a case where the positive electrode active material does not contain any coating layer or contains Al oxide or Ti oxide as a coating layer.

With regard to the positive electrode active material, from the standpoint of reducing the diffusion rate of the acetonitrile-containing non-aqueous electrolyte solution into deep parts of the positive electrode active material particles and thereby inhibiting lithium extraction in the deep parts of the positive electrode active material particles, a case of containing a coating layer is more preferred than a case of containing a doping element.

When a cross-sectional SEM image of the positive electrode after 100 cycles of charging and discharging under a high temperature environment was observed, a large number of cracks were confirmed between primary particles. These cracks induce an oxidative decomposition reaction of the electrolyte solution, an increase in the internal resistance, and elution of transition metals, resulting in deterioration of the cycle performance. Such cracking of the positive electrode active material associated with charging and discharging is believed to be caused by the stress applied to the crystal interface due to expansion and contraction of crystal. In a positive electrode active material having a large crystallite size, the ratio of crystallite interface is reduced than in a positive electrode active material having a small crystallite size; therefore, by controlling the positive electrode active material to have a large crystallite size, various deterioration phenomena under a high temperature environment can be inhibited. Accordingly, the crystallite size of the positive electrode after 100 cycles of the above-described energization process is preferably 500 Å or larger, more preferably 600 Å or larger.

The positive electrode active material may be a lithium-containing compound other than the above-described lithium-containing metal oxides represented by Formulae (a) and (b), and is not particularly limited as long as it contains lithium. Examples of such a lithium-containing compound include: composite oxides containing lithium and a transition metal element; metal chalcogenides containing lithium; metal phosphate compounds containing lithium and a transition metal element; and metal silicate compounds containing lithium and a transition metal element. From the standpoint of obtaining a higher voltage, the lithium-containing compound is particularly preferably a metal phosphate compound that contains lithium and at least one transition metal element selected from the group consisting of Co, Ni, Mn, Fe, Cu, Zn, Cr, V, and Ti.

More specific examples of the lithium-containing compound include compounds represented by any of the following Formulae (Xa), (Xb), and (Xc):

$$Li_v M^I D_2 \quad (Xa)$$

{wherein, D represents a chalcogen element; $M^I$ represents one or more transition metal elements; and v is determined by a charge-discharge state of the battery and represents a number of 0.05 to 1.10};

$$Li_w M^{II} PO_4 \quad (Xb)$$

{wherein, D represents a chalcogen element; $M^{II}$ represents one or more transition metal elements; and w is determined by a charge-discharge state of the battery and represents a number of 0.05 to 1.10}; and $$Li_t M^{III}_u SiO_4 \quad (Xc)$$

{wherein, D represents a chalcogen element; $M^{III}$ represents one or more transition metal elements; t is determined by a charge-discharge state of the battery and represents a number of 0.05 to 1.10; and u represent a number of 0 to 2}.

The lithium-containing compounds represented by Formula (Xa) have a layered structure, while the compounds represented by Formulae (Xb) or (Xc) have an olivine structure. For the purposes of structure stabilization and the like, these lithium-containing compounds may be, for example, those in which some of the transition metal elements are substituted with Al, Mg, or other transition metal element, those in which these metal elements are incorporated into the crystal grain boundaries, those in which some of the oxygen atoms are substituted with fluorine atoms or the like, or those in which the surface of the positive electrode active material is at least partially coated with other positive electrode active material.

As the positive electrode active material in the present embodiment, any of the above-described lithium-containing compounds may be used, and other positive electrode active material may be used in combination with the lithium-containing compound. Examples of the other positive electrode active material include: metal oxides and metal chalcogenides which have a tunnel structure and a layered structure; sulfur; and conductive polymers. Examples of the metal oxides and metal chalcogenides which have a tunnel structure and a layered structure include oxides, sulfides, and selenides of metals other than lithium, which are typified by $MnO_2$, $FeO_2$, $FeS_2$, $V_2O_5$, $V_6O_{13}$, $TiO_2$, $TiS_2$, $MoS_2$, and $NbSe_2$. The conductive polymers are typified by, for example, polyaniline, polythiophene, polyacetylene, and polypyrrole.

The above-described other positive electrode active material may be used singly or in combination of two or more thereof, and is not particularly limited. However, the positive electrode active material layer preferably contains at least one transition metal element selected from Ni, Mn, and Co, since this allows occlusion and release of lithium ions to occur in a reversible and stable manner and can achieve a high energy density.

When a lithium-containing compound and other positive electrode active material are used in combination as the positive electrode active material, their usage ratio, namely the usage ratio of the lithium-containing compound with respect to the whole positive electrode active material, is preferably 80% by weight or higher, more preferably 85% by weight or higher.

(Conductive Aid)

Examples of the conductive aid include: carbon blacks typified by graphite, acetylene black, and Ketjen black; and carbon fibers. The content ratio of the conductive aid is preferably 10 parts by weight or less, more preferably 1 to 5 parts by weight, with respect to 100 parts by weight of the positive electrode active material.

(Binder)

Examples of the binder include polyvinylidene fluoride (PVDF), polytetrafluoroethylene (PTFE), polyacrylic acid, styrene-butadiene rubbers, and fluororubbers. The content ratio of the binder is preferably 6 parts by weight or less, more preferably 0.5 to 4 parts by weight, with respect to 100 parts by weight of the positive electrode active material.

<Positive Electrode Current Collector>

The positive electrode current collector is composed of, for example, a metal foil such as an aluminum foil, a nickel foil, or a stainless steel foil. The surface of the positive electrode current collector may be coated with carbon, and the positive electrode current collector may be processed into a mesh form. The thickness of the positive electrode current collector is preferably 5 to 40 μm, more preferably 7 to 35 μm, still more preferably 9 to 30 μm.

<Formation of Positive Electrode Active Material Layer>

The positive electrode active material layer is formed by applying a positive electrode mixture-containing slurry, in which a positive electrode mixture obtained by mixing the positive electrode active material with the conductive aid and the binder as required is dispersed in a solvent, to the positive electrode current collector, and subsequently drying the slurry (solvent removal), followed by pressing as required. The solvent is not particularly limited, and any conventionally known solvent can be used. Examples thereof include N-methyl-2-pyrrolidone, dimethylformamide, dimethylacetamide, and water.

[Negative Electrode]

The negative electrode 160 is constituted by a negative electrode active material layer produced from a negative electrode mixture, and a negative electrode current collector. The negative electrode 160 can function as a negative electrode of a non-aqueous secondary battery.

The negative electrode active material layer contains a negative electrode active material, and preferably contains a conductive aid and a binder as required.

Examples of the negative electrode active material include: carbon materials typified by amorphous carbon (hard carbon), artificial graphite, natural graphite, pyrolytic carbon, coke, glassy carbon, calcined organic polymer compounds, mesocarbon microbeads, carbon fibers, activated carbons, graphites, carbon colloids, and carbon blacks; and metallic lithium, metal oxides, metal nitrides, lithium alloys, tin alloys, silicon alloys, intermetallic compounds, organic compounds, inorganic compounds, metal complexes, and organic polymer compounds. These negative electrode active materials may be used singly, or in combination of two or more thereof.

From the standpoint of increasing the battery voltage, the negative electrode active material layer preferably contains, as the negative electrode active material, a material capable of occluding lithium ions at a potential lower than 0.4 V vs. $Li/Li^+$.

Examples of the conductive aid include: carbon blacks typified by graphite, acetylene black, and Ketjen black; and carbon fibers. The content ratio of the conductive aid is preferably 20 parts by weight or less, more preferably 0.1 to 10 parts by weight, with respect to 100 parts by weight of the negative electrode active material.

Examples of the binder include carboxymethyl cellulose, PVDF, PTFE, polyacrylic acid, and fluororubbers, as well as diene-based rubbers such as styrene-butadiene rubbers. The content ratio of the binder is preferably 10 parts by weight or less, more preferably 0.5 to 6 parts by weight, with respect to 100 parts by weight of the negative electrode active material.

The negative electrode active material layer is formed by applying a negative electrode mixture-containing slurry, in which a negative electrode mixture obtained by mixing the negative electrode active material with the conductive aid and the binder as required is dispersed in a solvent, to the negative electrode current collector, and subsequently drying the slurry (solvent removal), followed by pressing as required. The solvent is not particularly limited, and any conventionally known solvent can be used. Examples thereof include N-methyl-2-pyrrolidone, dimethylformamide, dimethylacetamide, and water.

The negative electrode current collector is composed of, for example, a metal foil such as a copper foil, a nickel foil, or a stainless steel foil. The surface of the negative electrode current collector may be coated with carbon, and the negative electrode current collector may be processed into a mesh form. The thickness of the negative electrode current collector is preferably 5 to 40 μm, more preferably 6 to 35 μm, still more preferably 7 to 30 μm.

[Non-Aqueous Electrolyte Solution]

The term "non-aqueous electrolyte solution" used herein (hereinafter, also simply referred to as "electrolyte solution") refers to an electrolyte solution containing water in an amount of 1% by weight or less with respect to a total amount of the electrolyte solution.

The electrolyte solution of the present embodiment preferably contains as little water as possible, but may contain a very small amount of water as long as it does not interfere with solving the problems of the present invention. The content of water is 300 ppm by weight or less, preferably 200 ppm by weight or less, with respect to a total amount of the non-aqueous electrolyte solution. As long as the non-aqueous electrolyte solution is configured to solve the problems of the present invention, those constituent materials of a known non-aqueous electrolyte solution used in a lithium ion battery can be appropriately selected and applied as other constituents.

The electrolyte solution according to the first embodiment can contain acetonitrile, a non-aqueous solvent, and a lithium salt. In the first embodiment, from the standpoint of inhibiting an excessive increase in the internal resistance of the negative electrode, the electrolyte solution preferably contains no acid anhydride.

<Non-Aqueous Solvent>

The non-aqueous solvent will now be described. The term "non-aqueous solvent" used in the present embodiment refers to an element of the electrolyte solution, excluding the lithium salt and various additives. When the electrolyte solution contains an electrode protection additive, the "non-aqueous solvent" means an element of the electrolyte solution, excluding the lithium salt and additives other than the electrode protection additive. Examples of the non-aqueous solvent include: alcohols, such as methanol and ethanol; and aprotic solvents. Thereamong, the non-aqueous solvent is preferably an aprotic solvent. The non-aqueous solvent may also contain a solvent other than the aprotic solvent within a range that does not impair the effects of the present invention.

For example, the non-aqueous solvent according to the non-aqueous electrolyte solution can contain acetonitrile as the aprotic solvent. By incorporating acetonitrile into the non-aqueous solvent, the ionic conductivity of the non-aqueous electrolyte solution is increased, so that the diffusibility of lithium ions in the battery can be improved. Accordingly, when the non-aqueous electrolyte solution contains acetonitrile, particularly in the positive electrode in which the positive electrode active material layer is thickened and the filling amount of the positive electrode active material is thereby increased, lithium ions can diffuse in a favorable manner even into the region in the vicinity of the current collector where lithium ions hardly reach during high-load discharging. Therefore, a sufficient capacity can be extracted during high-load charging as well, making it possible to obtain a non-aqueous secondary battery having excellent load characteristics.

Further, by incorporating acetonitrile into the non-aqueous solvent, the rapid charging characteristics of the non-aqueous secondary battery can be improved. In constant current-constant voltage (CC-CV) charging of the non-aqueous secondary battery, the capacity per unit time in a CC charging period is larger than the charging capacity per unit time in a CV charging period. When acetonitrile is used in the non-aqueous solvent of the non-aqueous electrolyte solution, not only the CC-chargeable region can be increased (the CC charging time can be extended) but also the charging current can be increased; therefore, the time required for bringing the non-aqueous secondary battery into a fully-charged state from the start of charging can be greatly reduced.

It is noted here that acetonitrile is electrochemically easily reduced and decomposed. In addition, some conventional lithium ion secondary batteries using an acetonitrile-containing non-aqueous electrolyte solution have poor long-term durability. From the results of various verification experiments, the reason why a lithium ion secondary battery using an acetonitrile-containing non-aqueous electrolyte solution has poor long-term durability is considered as follows:

An acetonitrile-containing non-aqueous electrolyte solution has a higher ionic conductivity than an existing electrolyte solution and thus causes extraction of more lithium ions from a positive electrode during charging. Accordingly, a large amount of polyvalent transition metals including quadrivalent Ni exits in the positive electrode during charging, and elution of these metals tends to occur easily. This tendency is pronounced when a composite metal oxide containing lithium and nickel and having a high Ni content ratio is used as an active material of the positive electrode. Therefore, when acetonitrile is used, it is preferable to use other solvent (e.g., an aprotic solvent other than acetonitrile) in combination with acetonitrile as the non-aqueous solvent, and/or to add an electrode protection additive for the formation of a protective film on the electrode.

The content of acetonitrile is preferably 5 to 20% by volume in terms of the amount per total amount of the non-aqueous solvent. The content of acetonitrile is more preferably not less than 5% by volume, still more preferably not less than 10% by volume, but more preferably 20% by volume or less, still more preferably 17.5% by volume or less, in terms of the amount per total amount of the non-aqueous solvent. When the content of acetonitrile is 5% by volume or more in terms of the amount per total amount of the non-aqueous solvent, not only the ionic conductivity is increased and high output characteristics tend to be exerted, but also dissolution of the lithium salt can be facilitated. When the content of acetonitrile is 20% by volume or less in terms of the amount per total amount of the non-aqueous solvent, the amount of lithium extraction from the positive electrode is made uniform, so that cracking of the positive electrode active material is inhibited. In addition, since the amount of lithium extraction from the positive electrode is made uniform, spinel transition facilitated by non-uniform lithium extraction is inhibited and the rate of change in the c-axis lattice constant of the positive electrode is reduced, so that cracking of the positive electrode active material is inhibited. As a result, various deterioration phenomena under a high temperature environment can be inhibited. An increase in the internal resistance of the battery is inhibited by the below-described additives; therefore, when the content of acetonitrile in the non-aqueous solvent is in the above-described range, the high-temperature cycle characteristics and other battery characteristics tend to be further improved while maintaining the excellent performance of acetonitrile.

The aprotic solvent other than acetonitrile may be, for example, a cyclic carbonate, a fluoroethylene carbonate, a lactone, a sulfur atom-containing organic compound, a fluorinated linear carbonate, a cyclic ether, a mononitrile other than acetonitrile, an alkoxy group-substituted nitrile, a cyclic nitrile, a short-chain fatty acid ester, a linear ether, a fluorinated ether, a ketone, or a compound in which at least one or all of H atoms of any of the above-described aprotic solvents are substituted with halogen atoms.

Examples of the cyclic carbonate include ethylene carbonate, propylene carbonate, 1,2-butylene carbonate, trans-2,3-butylene carbonate, cis-2,3-butylene carbonate, 1,2-pentylene carbonate, trans-2,3-pentylene carbonate, cis-2,3-pentylene carbonate, vinylene carbonate, 4,5-dimethylvinylene carbonate, and vinylethylene carbonate;

examples of the fluoroethylene carbonate include 4-fluoro-1,3-dioxolan-2-one, 4,4-difluoro-1,3-dioxolan-2-one, cis-4,5-difluoro-1,3-dioxolan-2-one, trans-4,5-difluoro-1,3-dioxolan-2-one, 4,4,5-trifluoro-1,3-dioxolan-2-one, 4,4,5,5-tetrafluoro-1,3-dioxolan-2-one, and 4,4,5-trifluoro-5-methyl-1,3-dioxolan-2-one;

examples of the lactone include γ-butyrolactone, α-methyl-γ-butyrolactone, γ-valerolactone, γ-caprolactone, δ-valerolactone, δ-caprolactone, and ε-caprolactone;

examples of the sulfur atom-containing organic compound include ethylene sulfite, propylene sulfite, butylene sulfite, pentene sulfite, sulfolane, 3-sulfolane, 3-methyl sulfolane, 1,3-propane sultone, 1,4-butane sultone, 1-propene-1,3-sultone, dimethyl sulfoxide, tetramethylene sulfoxide, and ethylene glycol sulfite;

examples of the linear carbonate include ethyl methyl carbonate, dimethyl carbonate, diethyl carbonate, methyl propyl carbonate, methyl isopropyl carbonate, dipropyl carbonate, methyl butyl carbonate, dibutyl carbonate, and ethyl propyl carbonate;

examples of the cyclic ether include tetrahydrofuran, 2-methyl tetrahydrofuran, 1,4-dioxane, and 1,3-dioxane;

examples of the mononitrile other than acetonitrile include propionitrile, butyronitrile, valeronitrile, benzonitrile, and acrylonitrile;

examples of the alkoxy group-substituted nitrile include methoxyacetonitrile and 3-methoxypropionitrile;

examples of the cyclic nitrile include benzonitrile;

examples of the short-chain fatty acid ester include methyl acetate, methyl propionate, methyl isobutyrate, methyl butyrate, methyl isovalerate, methyl valerate, methyl pivalate, methyl hydroangelate, methyl caproate, ethyl acetate, ethyl propionate, ethyl isobutyrate, ethyl butyrate, ethyl isovalerate, ethyl valerate, ethyl pivalate, ethyl hydroangelate, ethyl caproate, propyl acetate, propyl propionate, propyl isobutyrate, propyl butyrate, propyl isovalerate, propyl valerate, propyl pivalate, propyl hydroangelate, propyl caproate, isopropyl acetate, isopropyl propionate, isopropyl isobutyrate, isopropyl butyrate, isopropyl isovalerate, isopropyl valerate, isopropyl pivalate, isopropyl hydroangelate, isopropyl caproate, butyl acetate, butyl propionate, butyl isobutyrate, butyl butyrate, butyl isovalerate, butyl valerate, butyl pivalate, butyl hydroangelate, butyl caproate, isobutyl acetate, isobutyl propionate, isobutyl isobutyrate, isobutyl butyrate, isobutyl isovalerate, isobutyl valerate, isobutyl pivalate, isobutyl hydroangelate, isobutyl caproate, tert-butyl acetate, tert-butyl propionate, tert-butyl isobutyrate, tert-butyl butyrate, tert-butyl isovalerate, tert-butyl valerate, tert-butyl pivalate, tert-butyl hydroangelate, and tert-butyl caproate;

examples of the linear ether include dimethoxyethane, diethyl ether, 1,3-dioxolane, diglyme, triglyme, and tetraglyme;

examples of the fluorinated ether include $Rf^{20}$—$OR^{21}$ (wherein, $Rf^{20}$ represents a fluorine atom-containing alkyl group, and $R^{21}$ represents an organic group optionally containing a fluorine atom);

examples of the ketone include acetone, methyl ethyl ketone, and methyl isobutyl ketone; and examples of the compound in which at least one or all of H atoms of any of the above-described aprotic solvents are substituted with halogen atoms include such compounds in which the halogen atoms are fluorine atoms.

Examples of fluorinated products of the linear carbonate include methyl trifluoroethyl carbonate, trifluorodimethyl carbonate, trifluorodiethyl carbonate, trifluoroethyl methyl carbonate, methyl-2,2-difluoroethyl carbonate, methyl-2,2,2-trifluoroethyl carbonate, and methyl-2,2,3,3-tetrafluoropropyl carbonate. These fluorinated linear carbonates can be represented by the following general formula:

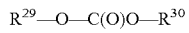

$R^{29}$—O—C(O)O—$R^{30}$ (wherein, $R^{29}$ and $R^{30}$ each represent at least one selected from the group consisting of $CH_3$, $CH_2CH_3$, $CH_2CH_2CH_3$, $CH(CH_3)_2$, and $CH_2Rf^{31}$; $Rf^{31}$ represents an alkyl group having 1 to 3 carbon atoms in which a hydrogen atom is substituted with at least one fluorine atom; and $R^{29}$ and/or $R^{30}$ contain at least one fluorine atom).

Examples of fluorinated products of the short-chain fatty acid ester include fluorinated short-chain fatty acid esters typified by 2,2-difluoroethyl acetate, 2,2,2-trifluoroethyl acetate, and 2,2,3,3-tetrafluoropropyl acetate. These fluorinated short-chain fatty acid esters can be represented by the following general formula:

$R^{32}$—C(O)O—$R^{33}$ (wherein, $R^{32}$ represents at least one selected from the group consisting of $CH_3$, $CH_2CH_3$, $CH_2CH_2CH_3$, $CH(CH_3)_2$, $CF_3CF_2H$, $CFH_2$, $CF_2Rf^{34}$, $CFHRf^{34}$, and $CH_2Rf^{35}$; $R^{33}$ represents at least one selected from the group consisting of $CH_3$, $CH_2CH_3$, $CH_2CH_2CH_3$, $CH(CH_3)_2$, and $CH_2Rf^{35}$; $Rf^{34}$ represents an alkyl group having 1 to 3 carbon atoms in which a hydrogen atom is substituted with at least one fluorine atom; $Rf^{35}$ represents an alkyl group having 1 to 3 carbon atoms in which a hydrogen atom is substituted with at least one fluorine atom; $R^{32}$ and/or $R^{33}$ contain at least one fluorine atom, and $R^{33}$ is not $CH_3$ when $R^{32}$ is $CF_2H$).

In the present embodiment, these aprotic solvents other than acetonitrile may be used singly, or in combination of two or more thereof.

From the standpoint of improving the stability of the non-aqueous electrolyte solution, the non-aqueous solvent in the present embodiment preferably contains at least one of a cyclic carbonate and a linear carbonate in combination with acetonitrile. From the same standpoint, the non-aqueous solvent in the present embodiment more preferably contains a cyclic carbonate in combination with acetonitrile, and still more preferably contains both a cyclic carbonate and a linear carbonate in combination with acetonitrile.

When a cyclic carbonate is used in combination with acetonitrile, the cyclic carbonate particularly preferably contains ethylene carbonate, vinylene carbonate, and/or fluoroethylene carbonate.

<Lithium Salt>

The non-aqueous electrolyte solution of the present embodiment is not particularly limited as long as the lithium salt is not limited above. For example, in the present embodiment, the non-aqueous electrolyte solution contains $LiPF_6$ or an imide salt as the lithium salt.

The content of the lithium salt in the non-aqueous electrolyte solution of the present embodiment is preferably less than 3 mol in terms of the amount per 1 L of the non-aqueous solvent. When the content of the lithium salt is in this range, not only an excessive increase in the viscosity is inhibited, but also the ionic conductivity is increased and high output characteristics tend to be exerted.

(Imide Salt)

The imide salt is a lithium salt represented by LiN$(SO_2C_mF_{2m+1})_2$ [wherein, m represents an integer of 0 to 8] and, specifically, the imide salt preferably contains at least one of $LiN(SO_2F)_2$ and $LiN(SO_2CF_3)_2$. The imide salt may contain only one of these imide salts, or may contain an imide salt other than these imide salts.

When the non-aqueous solvent contains acetonitrile, since the saturation concentration of the imide salt with respect to acetonitrile is higher than that of $LiPF_6$, the non-aqueous solvent preferably contains the imide salt at a molar concentration that satisfies $LiPF_6 \leq$ imide salt as this can inhibit association and precipitation of the lithium salt with acetonitrile at a low temperature. Further, from the standpoint of the ion supply amount, the content of the imide salt is preferably 0.5 mol to 3 mol with respect to 1 L of the non-aqueous solvent. By using an acetonitrile-containing non-aqueous electrolyte solution that contains at least one of $LiN(SO_2F)_2$ and $LiN(SO_2CF_3)_2$, a reduction of the ionic conductivity in a low-temperature range such as −10° C. or −30° C. can be effectively inhibited, so that excellent low-temperature characteristics can be obtained. By restricting the content of the imide salt in this manner, an increase in the resistance during high-temperature heating can be more effectively inhibited as well.

(Fluorine-Containing Inorganic Lithium Salt)

The lithium salt may also contain a fluorine-containing inorganic lithium salt other than $LiPF_6$ and, for example, the lithium salt may contain a fluorine-containing inorganic lithium salt such as $LiBF_4$, $LiAsF_6$, $Li_2SiF_6$, $LiSbF_6$, or $Li_2B_{12}F_bH_{12-b}$ [wherein, b represents an integer of 0 to 3]. The term "inorganic lithium salt" used herein refers to a lithium salt that contains no carbon atom in its anion and is soluble in acetonitrile. Further, the term "fluorine-containing inorganic lithium salt" used herein refers to a lithium salt that contains a fluorine atom in its anion without any carbon atom and is soluble in acetonitrile. A fluorine-containing inorganic lithium salt is excellent in that it forms a passivation film on the surface of the metal foil used as the positive electrode current collector and inhibits corrosion of the positive electrode current collector. Such a fluorine-containing inorganic lithium salt is used singly, or two or more thereof are used in combination. As the fluorine-containing inorganic lithium salt, a double salt compound of LiF and a Lewis acid is desirable and particularly, the use of a fluorine-containing inorganic lithium salt having a phosphorus atom is more preferred since it facilitates the release of free fluorine atoms. A typical fluorine-containing inorganic lithium salt is $LiPF_6$ that releases a $PF_6$ anion when dissolved. The use of a fluorine-containing inorganic lithium salt having a boron atom as the fluorine-containing inorganic lithium salt is preferred since an excess free acid component that may cause battery deterioration is made more likely to be captured and, from this standpoint, $LiBF_4$ is particularly preferred.

In the non-aqueous electrolyte solution of the present embodiment, the content of the fluorine-containing inorganic lithium salt is not particularly limited; however, it is preferably not less than 0.01 mol, more preferably not less than 0.1 mol, still more preferably not less than 0.25 mol, with respect to 1 L of the non-aqueous solvent. When the content of the fluorine-containing inorganic lithium salt is in this range, the ionic conductivity is increased and high output characteristics tend to be exerted. The content of the fluorine-containing inorganic lithium salt is also preferably less than 2.8 mol, more preferably less than 1.5 mol, still more preferably less than 1 mol, with respect to 1 L of the non-aqueous solvent. When the content of the fluorine-containing inorganic lithium salt is in this range, not only the ionic conductivity is increased and high output characteristics can be exerted, but also a reduction in the ionic conductivity due to an increase in the viscosity at a low temperature tends to be inhibited, so that the high-temperature cycle characteristics and other battery characteristics tend to be further improved while maintaining excellent performance of the non-aqueous electrolyte solution.

(Organic Lithium Salt)

The non-aqueous electrolyte solution of the present embodiment may further contain an organic lithium salt. The term "organic lithium salt" used herein refers to a lithium salt that contains a carbon atom in its anion and is soluble in acetonitrile.

The organic lithium salt may be, for example, an oxalic acid group-containing organic lithium salt. Specific examples of the oxalic acid group-containing organic lithium salt include organic lithium salts represented by $LiB(C_2O_4)_2$, $LiBF_2(C_2O_4)$, $LiPF_4(C_2O_4)$, and $LiPF_2(C_2O_4)_2$, among which at least one lithium salt selected from the lithium salts represented by $LiB(C_2O_4)_2$ and $LiBF_2(C_2O_4)$ is preferred. It is more preferable to use one or more of these lithium salts in combination with a fluorine-containing inorganic lithium salt. The oxalic acid group-containing organic lithium salt may be added to the non-aqueous electrolyte solution, or may be incorporated into the negative electrode (negative electrode active material layer).

The amount of the oxalic acid group-containing organic lithium salt to be added to the non-aqueous electrolyte solution is, from the standpoint of ensuring the effects of its use in a more favorable manner, preferably not less than 0.005 mol, more preferably not less than 0.02 mol, still more preferably not less than 0.05 mol, per 1 L of the non-aqueous solvent in the non-aqueous electrolyte solution. However, an excessively large amount of the oxalic acid group-containing organic lithium salt in the non-aqueous electrolyte solution may lead to precipitation of this lithium salt. Therefore, the amount of the oxalic acid group-containing organic lithium salt to be added to the non-aqueous electrolyte solution is preferably less than 1.0 mol, more preferably less than 0.5 mol, still more preferably less than 0.2 mol, per 1 L of the non-aqueous solvent in the non-aqueous electrolyte solution.

Oxalic acid group-containing organic lithium salts are known to be hardly soluble in organic solvents having a low polarity, particularly linear carbonates. An oxalic acid group-containing organic lithium salt sometimes contains a trace amount of lithium oxalate, and may react with a trace amount of water contained in other raw material when mixed as a non-aqueous electrolyte solution and thereby cause the generation of new white precipitates of lithium oxalate. Therefore, the content of lithium oxalate in the non-aqueous electrolyte solution of the present embodiment is preferably, but not particularly limited to, 0 to 500 ppm.

(Other Lithium Salts)

As the lithium salt in the present embodiment, a lithium salt generally used in non-aqueous secondary batteries may be supplementarily added in addition to the above-described lithium salt. Specific examples of such other lithium salt include: inorganic lithium salts containing no fluorine atom in their anions, such as $LiClO_4$, $LiAlO_4$, $LiAlCl_4$, $LiB_{10}Cl_{10}$, and chloroborane Li; organic lithium salts, such as $LiCF_3SO_3$, $LiCF_3CO_2$, $Li_2C_2F_4(SO_3)_2$, $LiC(CF_3SO_2)_3$, $LiC_nF_{(2n+1)}SO_3$ (wherein, n≥2), Li lower aliphatic carboxylate, Li tetraphenyl borate, and $LiB(C_3O_4H_2)_2$; organic lithium salts represented by $LiPF_n(C_pF_{2p+1})_{6-n}$ [wherein, n represents an integer of 1 to 5, and p represents an integer of 1 to 8], such as $LiPF_5(CF_3)$; organic lithium salts represented by $LiBF_q(C_sF_{2s+1})_{4-q}$ [wherein, q represents an integer of 1 to 3, and s represents an integer of 1 to 8], such as $LiBF_3(CF_3)$; lithium salts bound with a polyvalent anion; and organic lithium salts each represented by:

the following Formula (a):

$$LiC(SO_2R^A)(SO_2R^B)(SO_2R^C) \quad (a)$$

{wherein, $R^A$, $R^B$, and $R^C$ are optionally the same or different from each other, and each represent a perfluoroalkyl group having 1 to 8 carbon atoms}, the following Formula (b):

$$LiN(SO_2OR^D)(SO_2OR^E) \quad (b)$$

{wherein, $R^D$ and $R^E$ are optionally the same or different from each other, and each represent a perfluoroalkyl group having 1 to 8 carbon atoms}, or the following Formula (c):

$$LiN(SO_2R^F)(SO_2OR^G) \quad (c)$$

{wherein, $R^F$ and $R^G$ are optionally the same or different from each other, and each represent a perfluoroalkyl group having 1 to 8 carbon atoms}.

One or more of these lithium salts can be used along with a fluorine-containing inorganic lithium salt.

<Dinitrile Compound>

The non-aqueous electrolyte solution of the present embodiment preferably contains a dinitrile compound represented by the following Formula (1):

[Chem. 4]

$$NC-R-CN \quad (1)$$

{wherein, R represents a straight-chain or branched divalent aliphatic alkyl group having 1 to 12 carbon atoms and optionally containing oxygen atoms}.

With regard to the dinitrile compound, it is presumed that its nitrile groups having a high metal coordination ability are coordinated to the transition metals contained in the positive electrode active material and thereby stabilizes the crystal structure of the positive electrode, as a result of which the rate of change in the c-axis lattice constant is reduced, and cracking of the positive electrode active material is inhibited. Consequently, various deterioration phenomena under a high temperature environment can be inhibited.

In Formula (1), the number of carbon atoms in the straight-chain or branched divalent aliphatic alkyl group R is preferably 1 to 12, more preferably 1 to 10, particularly preferably 1 to 8.

Specific examples of a straight-chain dinitrile compound include malononitrile, succinonitrile, glutaronitrile, adiponitrile, 1,5-dicyanopentane, 1,6-dicyanohexane, 1,7-dicyanoheptane, 1,8-dicyanooctane, 1,9-dicyanononane, 1,10-dicyanodecane, and 1,12-dicyanododecane.

Specific examples of a branched dinitrile compound include methylsuccinonitrile, tetramethylsuccinonitrile, 2-methylglutaronitrile, 2,4-dimethylglutaronitrile, 1,4-dicyanopentane, 1,4-dicyanoheptane, 1,5-dicyanoheptane, 2,6-dicyanoheptane, 1,7-dicyanooctane, 2,7-dicyanooctane, 1,8-dicyanononane, 2,8-dicyanononane, and 1,6-dicyanodecane.

Specific examples of dinitrile compound containing oxygen atoms include ethylene glycol bis(propionitrile) ether, diethylene glycol bis(2-cyanoethyl) ether, triethylene glycol bis(2-cyanoethyl) ether, tetraethylene glycol bis(2-cyanoethyl) ether, 1,3-bis(2-cyanoethoxy)propane, 1,4-bis(2-cyanoethoxy)butane, and 1,5-bis(2-cyanoethoxy)pentane.

Among these specific examples of the dinitrile compound, malononitrile, succinonitrile, glutaronitrile, adiponitrile, methylsuccinonitrile, 2-methylglutaronitrile, and ethylene glycol bis(propionitrile) ether are preferred; succinonitrile, glutaronitrile, methylsuccinonitrile, 2-methylglutaronitrile, and ethylene glycol bis(propionitrile) ether are more preferred; and succinonitrile, methylsuccinonitrile, and ethylene glycol bis(propionitrile) ether are still more preferred. These compounds may be used singly, or in combination of two or more thereof.

The content of the dinitrile compound in the non-aqueous electrolyte solution is 25% by weight or less, preferably 20% by weight or less, more preferably 18% by weight or less, with respect to a total amount of the non-aqueous electrolyte solution. The content of the dinitrile compound in the non-aqueous electrolyte solution is also preferably not less than 0.1% by weight, more preferably not less than 1% by weight, still more preferably not less than 1.5% by weight, particularly preferably not less than 5% by weight, with respect to a total amount of the non-aqueous electrolyte solution. By adjusting the content of the dinitrile compound to be in the above-described range, the crystal structure of the positive electrode can be stabilized and various deterioration phenomena under a high temperature environment can be inhibited while maintaining the properties of acetonitrile, such as high ionic conductivity and high output characteristics.

<Nitrogen-Containing Cyclic Compound>

The electrolyte solution in the present embodiment preferably contains a compound represented by the following Formula (2) (nitrogen-containing cyclic compound) as an additive:

[Chem. 5]

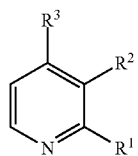

(2)

{wherein, substituents represented by $R^1$, $R^2$, and $R^3$ each independently represent a hydrogen atom, an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, a phenyl group, a cyclohexyl group, a nitrile group, a nitro group, an amino group, an N,N-dimethylamino group, or an N,N-diethylamino group; and at least two of these substituents are hydrogen atoms}.

Specific examples of the nitrogen-containing cyclic compound include pyridine, 2-methylpyridine, 3-methylpyridine, 4-methylpyridine, 2-ethylpyridine, 3-ethylpyridine, 4-ethylpyridine, 2-(n-propyl)pyridine, 3-(n-propyl)pyridine, 4-(n-propyl)pyridine, 2-isopropylpyridine, 3-isopropylpyridine, 4-isopropylpyridine, 2-(n-butyl)pyridine, 3-(n-butyl)pyridine, 4-(n-butyl)pyridine, 2-(1-methylpropyl)pyridine, 3-(1-methylpropyl)pyridine, 4-(1-methylpropyl)pyridine, 2-(2-methylpropyl)pyridine, 3-(2-methylpropyl)pyridine, 4-(2-methylpropyl)pyridine, 2-(tert-butyl)pyridine, 3-(tert-butyl)pyridine, 4-(tert-butyl)pyridine, 2-trifluoromethylpyridine, 3-trifluoromethylpyridine, 4-trifluoromethylpyridine, 2-(2,2,2-trifluoroethyl)pyridine, 3-(2,2,2-trifluoroethyl)pyridine, 4-(2,2,2-trifluoroethyl)pyridine, 2-(pentafluoroethyl)pyridine, 3-(pentafluoroethyl)pyridine, 4-(pentafluoroethyl)pyridine, 2-methoxypyridine, 3-methoxypyridine, 4-methoxypyridine, 2-ethoxypyridine, 3-ethoxypyridine, 4-ethoxypyridine, 2-(n-propoxy)pyridine, 3-(n-propoxy)pyridine, 4-(n-propoxy)pyridine, 2-isopropoxypyridine, 3-isopropoxypyridine, 4-isopropoxypyridine, 2-(n-butoxy)pyridine, 3-(n-butoxy)pyridine, 4-(n-butoxy)pyridine, 2-(1-methylpropoxy)pyridine, 3-(1-methylpropoxy)pyridine, 4-(1-methylpropoxy)pyridine, 2-(2-methylpropoxy)pyridine, 3-(2-methylpropoxy)pyridine, 4-(2-methylpropoxy)pyridine, 2-trifluoromethoxypyridine, 3-trifluoromethoxypyridine, 4-trifluoromethoxypyridine, 2-(2,2,2-trifluoroethoxy)pyridine, 3-(2,2,2-trifluoroethoxy)pyridine, 4-(2,2,2-trifluoroethoxy)pyridine, 2-phenylpyridine, 3-phenylpyridine, 4-phenylpyridine, 2-cyclohexylpyridine, 3-cyclohexylpyridine, 4-cyclohexylpyridine, 2-cyanopyridine, 3-cyanopyridine, 4-cyanopyridine, 2-aminopyridine, 3-aminopyridine, 4-aminopyridine, 2-(N,N-dimethylamino)pyridine, 3-(N,N-dimethylamino)pyridine, 4-(N,N-dimethylamino)pyridine, 2-(N,N-diethylamino)pyridine, 3-(N,N-diethylamino)pyridine, and 4-(N,N-diethylamino)pyridine. These compounds may be used singly, or in combination of two or more thereof.

There is desirably no steric hindrance around the nitrogen atom in the nitrogen-containing cyclic compound. Accordingly, it is preferred that $R^1$ in Formula (2) be a hydrogen atom, and it is more preferred that both $R^1$ and $R^2$ be hydrogen atoms. When $R^1$ and $R^2$ in Formula (2) are both hydrogen atoms, from the standpoint of the electronic effect on the lone electron pair existing on the nitrogen atom, $R^3$ in Formula (2) is preferably a hydrogen atom or a tert-butyl group.

When the electrolyte solution on the present embodiment contains the above-described nitrogen-containing cyclic compound represented by Formula (2) as an additive, the rate of change in the c-axis lattice constant tends to be reduced. The nitrogen-containing cyclic compound not only functions as a stabilizer of $LiPF_6$ but also inhibits phase transition of the positive electrode active material and thereby contributes to stabilization of the crystal structure, so that cracking of the positive electrode active material is inhibited. As a result, various deterioration phenomena under a high temperature environment can be inhibited.

The content of the nitrogen-containing cyclic compound in the electrolyte solution of the present embodiment is not particularly limited; however, it is preferably 0.01 to 10% by weight, more preferably 0.02 to 5% by weight, still more preferably 0.05 to 3% by weight, based on a total amount of the electrolyte solution. By adjusting the content of the nitrogen-containing cyclic compound to be in the above-described range, the crystal structure of the positive electrode can be stabilized, and various deterioration phenomena under a high temperature environment can be inhibited while maintaining the properties of acetonitrile, such as high ionic conductivity and high output characteristics.

<Condensation Polycyclic Heterocyclic Compound>

The non-aqueous electrolyte solution of the present embodiment may contain a compound (condensation polycyclic heterocyclic compound) that has a structure satisfying the following 1 to 5:

1. the structure is a condensation polycyclic heterocycle,
2. a pyrimidine skeleton is contained in the condensation polycyclic heterocycle,
3. three or more nitrogen atoms are contained in the condensation polycyclic heterocycle,
4. five or more sp2 carbon atoms are contained in the condensation polycyclic heterocycle, and
5. no hydrogen atom is bound to the nitrogen atoms in the condensation polycyclic heterocycle.

As such a condensation polycyclic heterocyclic compound, a purine derivative is preferred and, particularly, caffeine is more preferred. The term "purine derivative" used herein refers to a compound that has, as a basic skeleton, a bicyclic heterocycle in which an imidazole ring is bound to a pyrimidine skeleton. In the present embodiment, the condensation polycyclic heterocyclic compound inhibits the generation of a complex cation formed from a transition metal and acetonitrile. Therefore, a non-aqueous secondary battery containing the condensation polycyclic heterocyclic compound exhibits excellent load characteristics, and an increase in the internal resistance during repeated charge-discharge cycles is inhibited.

The content of the condensation polycyclic heterocyclic compound in the electrolyte solution of the present embodiment is preferably 0.01% by weight to 5% by weight, more preferably 0.05% by weight to 1% by weight, still more preferably 0.1% by weight to 0.5% by weight, based on a total amount of the electrolyte solution. By adjusting the content of the condensation polycyclic heterocyclic compound in the present embodiment to be in this range, a complex cation-generating reaction on the electrode surface can be inhibited and an increase in the internal resistance due to charging and discharging can be reduced, without impairing the basic functions of the non-aqueous secondary battery. By preparing the electrolyte solution of the present embodiment in this range, the cyclic performance, the high-output performance under a low temperature environment, and other battery characteristics can all be further improved in the resulting non-aqueous secondary battery.

<Silanol Compound>

The non-aqueous electrolyte solution of the present embodiment may contain a silanol compound represented by the following Formula (3):

{wherein, $R^3$ and $R^4$ each represent an alkyl group optionally substituted with an aryl group, an alkoxysilyl group or a halogen atom, or an aryl group optionally substituted with an alkyl group, an alkoxysilyl group or a halogen atom; and X represents the following Formula (5):

[Chem. 6]

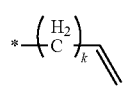

(5)

(wherein, k represents an integer of 0 to 8, and * represents a binding site with Si)}.

As such a silanol compound, triethoxyvinylsilane, trimethoxy(7-octen-1-yl)silane, vinyltrimethoxysilane, vinyl-tris(2-methoxyethoxy)silane, diethoxymethylvinylsilane, and dimethoxymethylvinylsilane are preferred and, thereamong, triethoxyvinylsilane is more preferred.

The silanol compound has an effect of inhibiting the active site (active site of the positive electrode active material) that causes oxidative deterioration of the non-aqueous electrolyte solution. Therefore, the use of such a compound enables to provide a non-aqueous electrolyte solution and a non-aqueous secondary battery, which can exert excellent load characteristics and in which various deterioration phenomena during high-temperature storage or repeated charge-discharge cycles can be inhibited.

The content of the silanol compound is preferably 0.01% by weight to 10% by weight, more preferably 0.05% by weight to 1% by weight, still more preferably 0.1% by weight to 0.5% by weight, in terms of the amount per total amount of the non-aqueous electrolyte solution. In this range, the active site of the positive electrode active material that causes oxidative deterioration of the non-aqueous electrolyte solution can be effectively inhibited while maintaining the non-aqueous secondary battery to be in a state of having a low internal resistance.

<Electrode Protection Additive>

The electrolyte solution of the present embodiment may contain an additive for protecting the electrodes. This electrode protection additive is not particularly limited as long as it does not interfere with solving the problems of the present invention. The electrode protection additive may be substantially redundant with a substance that plays a role as a solvent for dissolving the lithium salt (i.e., the above-described non-aqueous solvent). The electrode protection additive is preferably a substance that contributes to an improvement in the performance of the electrolyte solution and the non-aqueous secondary battery of the present embodiment, and it also encompasses a substance that is not directly involved in an electrochemical reaction.

Specific examples of the electrode protection additive include: fluoroethylene carbonates typified by 4-fluoro-1,3-dioxolan-2-one, 4,4-difluoro-1,3-dioxolan-2-one, cis-4,5-difluoro-1,3-dioxolan-2-one, trans-4,5-difluoro-1,3-dioxolan-2-one, 4,4,5-trifluoro-1,3-dioxolan-2-one, 4,4,5,5-tetrafluoro-1,3-dioxolan-2-one, and 4,4,5-trifluoro-5-methyl-1,3-dioxolan-2-one; unsaturated bond-containing cyclic carbonates typified by vinylene carbonate, 4,5-dimethylvinylene carbonate, and vinylethylene carbonate; lactones typified by γ-butyrolactone, γ-valerolactone, γ-caprolactone, δ-valerolactone, δ-caprolactone, and ε-caprolactone; cyclic ethers typified by 1,4-dioxane; cyclic sulfur compounds typified by ethylene sulfite, propylene sulfite, butylene sulfite, pentene sulfite, sulfolane, 3-sulfolene, 3-methyl sulfolane, 1,3-propane sultone, 1,4-butane sultone, 1-propen-1,3-sultone, and tetramethylene sulfoxide; chain acid anhydrides typified by acetic anhydride, propionic anhydride, and benzoic anhydride; cyclic acid anhydrides typified by malonic anhydride, succinic anhydride, glutaric anhydride, maleic anhydride, phthalic anhydride, 1,2-cyclohexane dicarboxylic anhydride, 2,3-naphthalene dicarboxylic anhydride, and naphthalene-1,4,5,8-tetracarboxylic dianhydride; and mixed acid anhydrides having a structure in which different kinds of acids, such as two different carboxylic acids or a combination of a carboxylic acid and a sulfonic acid, are dehydrated and condensed. These electrode protection additives may be used singly, or in combination of two or more thereof.

The content of the electrode protection additive in the electrolyte solution of the present embodiment is not particularly limited; however, it is preferably 0.1 to 30% by volume, more preferably 0.3 to 15% by volume, still more preferably 0.5 to 4% by volume, with respect to a total amount of the non-aqueous solvent.

In the present embodiment, a higher content of the electrode protection additive leads to a further inhibition of the deterioration of the electrolyte solution. However, a lower content of the electrode protection additive leads to a further improvement in the high-output characteristics of the non-aqueous secondary battery under a low temperature environment. Therefore, by adjusting the content of the electrode protection additive to be in the above-described range, excellent performance based on the high ionic conductivity of the electrolyte solution tends to be maximized without impairing the basic functions of the non-aqueous secondary battery. By preparing the electrolyte solution to have such a composition, the cyclic performance, the high-output performance under a low temperature environment, and other characteristics of the non-aqueous secondary battery all tend to be further improved.

Acetonitrile, which is one component of the non-aqueous solvent, is electrochemically easily reduced and decomposed; therefore, the non-aqueous solvent containing acetonitrile preferably contains at least one cyclic aprotic polar solvent, more preferably contains at least one unsaturated bond-containing cyclic carbonate, as an electrode protection additive for the formation of a protective film on the negative electrode.

The mixing molar ratio of the electrode protection additive with respect to acetonitrile is preferably 0.06 to 2, since this prevents the low-temperature performance from being deteriorated by an excessive protective film while forming a negative electrode protective film for the inhibition of reductive decomposition of acetonitrile.

The unsaturated bond-containing cyclic carbonate is preferably vinylene carbonate, and the content of vinylene carbonate in the non-aqueous electrolyte solution is preferably 0.1% by volume to 4% by volume, more preferably 0.2% by volume or more but less than 3% by volume, still more preferably 0.5% by volume or more but less than 2.5% by volume. This can improve the low-temperature durability more effectively, so that a secondary battery having excellent low-temperature performance can be provided.

Vinylene carbonate used as the electrode protection additive is often indispensable since it inhibits a reductive decomposition reaction of acetonitrile on the negative electrode surface, and an insufficient amount of vinylene carbonate can cause rapid deterioration of the battery performance. On the other hand, excessive film formation leads to deterioration of the low-temperature performance. Therefore, by adjusting the amount of vinylene carbonate to be in the above-described range, not only the interfacial (film) resistance can be kept low, but also the cycle deterioration at a low temperature can be inhibited.

(Other Optional Additives)

In the present embodiment, for the purpose of improving the charge-discharge cycle characteristics, the high-temperature storage characteristics, the safety (e.g., inhibition of overcharging) and the like of the non-aqueous secondary battery, an optional additive(s) selected from, for example, sulfonic acid esters, diphenyl disulfide, cyclohexylbenzene, biphenyl, fluorobenzene, tert-butylbenzene, phosphoric acid esters [e.g., ethyl diethyl phosphonoacetate (EDPA); $(C_2H_5O)_2(P=O)—CH_2(C=O)OC_2H_5$, tris(trifluoroethyl) phosphate (TFEP): $(CF_3CH_2O)_3P=O$, triphenyl phosphate (TPP): $(C_6H_5O)_3P=O$:$(CH_2=CHCH_2O)_3P=O$, and triallyl phosphate], nitrogen-containing cyclic compounds with no steric hindrance around a lone electron pair [e.g., pyridine, 1-methyl-1H-benzotriazole, and 1-methylpyrazole] and derivatives of these compounds, may be incorporated into the non-aqueous electrolyte solution as appropriate. Particularly, a phosphoric acid ester is effective since it has an effect of inhibiting side reactions during storage.

In the present embodiment, the content of other optional additive is calculated in terms of the weight percentage with respect to a total weight of all components constituting the non-aqueous electrolyte solution. The content of other optional additive is not particularly limited; however, it is in a range of preferably 0.01% by weight to 10% by weight, more preferably 0.02% by weight to 5% by weight, still more preferably 0.05 to 3% by weight, with respect to a total amount of the non-aqueous electrolyte solution. By adjusting the content of other optional additive to be in this range, further improved battery characteristics tend to be provided without impairing the basic functions of the non-aqueous secondary battery.

<$FSO_3$ Anion>

An acetonitrile-containing electrolyte solution tends to increase the amount of lithium ions extracted from the positive electrode. It was found that, as a result, the crystal structure of the positive electrode active material is destabilized, and this facilitates the elution of transition metals from the positive electrode active material and causes the transition metals to precipitate on the negative electrode surface. Accordingly, when the $FSO_3$ anion content is excessively high, $FSO_3$ anions undergo reductive decomposition reactions with the eluted metals precipitated on the negative electrode surface, and the thus deposited decomposition products increase the interfacial (coating film) resistance, causing deterioration of the output performance. Meanwhile, a small amount of $FSO_3$ anions has an effect of reinforcing the negative electrode protective film; therefore, the $FSO_3$ anion content is preferably in a range of 0.001 ppm to 100 ppm, more preferably in a range of 0.005 ppm to 70 ppm, still more preferably in a range of 0.011 ppm to 50 ppm, with respect to the non-aqueous electrolyte solution.

<Propionitrile>

Propionitrile quickly undergoes a reaction in the event of overcharging and contributes to α-hydrogen abstraction. This allows the battery to expand and rupture before combustion. Meanwhile, when deterioration of the positive electrode active material progresses, the positive electrode active material isolated due to cracking no longer contributes to the capacity and, when the battery is tried to be charged up to 4.2 V using only the chargeable/dischargeable positive electrode active material, the amount of lithium ions extracted from the chargeable/dischargeable positive electrode active material is increased, as a result of which the potential on the positive electrode side is increased. Thus, an addition of propionitrile in excess facilitates α-hydrogen abstraction reaction even in an ordinary voltage range, causing the generation of a gas reservoir in the electrode and a reduction in the capacity. Therefore, by controlling the amount of propionitrile contained in the non-aqueous electrolyte solution to be 1 ppm or less, or less than 1.0 ppm, the safety of the battery can be improved without deteriorating the battery performance in an ordinary voltage range.

The propionitrile content is preferably 0.001 ppm to 1 ppm, or 0.001 ppm or more but less than 1.0 ppm, more preferably 0.01 ppm to 1 ppm, or 0.01 ppm or more but less than 1.0 ppm, with respect to the non-aqueous electrolyte solution.

<Ionic Conductivity of Non-Aqueous Electrolyte Solution>

In the non-aqueous secondary battery, an increase in the electrode thickness can reduce the amount of members not contributing to the capacity and thus increase the energy density; however, when this is combined with the use of an electrolyte solution having a low ionic conductivity, the moving rate of lithium ions is limited by the ionic conductivity of the non-aqueous electrolyte solution, and the desired input-output characteristics are not obtained in some cases. Meanwhile, batteries in which a positive electrode active material having a high Ni ratio is used for a further increase in the energy density have been the mainstream of the development; however, when such batteries are used in combination with an electrolyte solution having a high ionic conductivity, even in the same voltage range, the charge-discharge capacity tends to be larger than in a case of using an electrolyte solution having a low ionic conductivity. When a cross-sectional SEM image of the positive electrode after 100 cycles was observed, a greater amount of cracks of the positive electrode active material was confirmed on the positive electrode surface side than on the current collector side. In other words, it is believed that, when an electrolyte solution having a high ionic conductivity is used, extraction of lithium ions occurs more excessively on the electrode surface where insertion and release of lithium ions are more likely to take place, as a result of which a greater amount of cracks of the positive electrode active material was generated.

Accordingly, the ionic conductivity of the non-aqueous electrolyte solution according to the present embodiment at 20° C. is preferably 10 mS/cm or higher but lower than 15 mS/cm, more preferably 11 mS/cm or higher but lower than 15 mS/cm, still more preferably 12 mS/cm or higher but lower than 15 mS/cm. When the ionic conductivity is 10 mS/cm or higher, the rate of insertion/release of lithium ions to/from the electrode is increased, so that high output characteristics tends to be exerted. Meanwhile, when the ionic conductivity is lower than 15 mS/cm, the amount of lithium extraction from the positive electrode is made uniform, so that cracking of the positive electrode active material is inhibited. In addition, since the amount of lithium extraction from the positive electrode is made uniform, not only spinel transition, which is facilitated by non-uniform lithium extraction, is inhibited, but also the rate of change in the c-axis lattice constant of the positive electrode is reduced, so that cracking of the positive electrode active material is inhibited. As a result, various deterioration phenomena under a high temperature environment can be inhibited.

<Separator>

From the standpoint of preventing a short circuit between the positive electrode 150 and the negative electrode 160 and providing safety such as shutdown, the non-aqueous secondary battery 100 of the present embodiment preferably includes a separator 170 between the positive electrode 150 and the negative electrode 160. The separator 170 is not limited and may be the same as one used in any known non-aqueous secondary battery, and the separator 170 is preferably an insulating thin film that has high ion permeability and excellent mechanical strength. Examples of the separator 170 include a woven fabric, a nonwoven fabric, and a microporous membrane made of a synthetic resin, among which a microporous membrane made of a synthetic resin is preferred.

As the microporous membrane made of a synthetic resin, for example, a polyolefin-based microporous membrane, such as a microporous membrane containing polyethylene or polypropylene as a main component, or a microporous membrane containing both of these polyolefins, is preferably used. Examples of the nonwoven fabric include porous membranes made of glass, ceramic, or a heat-resistant resin such as a polyolefin, a polyester, a polyamide, a liquid-crystal polyester, or aramid.

The separator 170 may be a single layer of one kind of microporous membrane, or may have a structure in which one kind of microporous membrane is disposed in plural layers, or two or more kinds of microporous membranes are laminated. The separator 170 may also have a structure in which a mixed resin material obtained by melt-kneading two or more resin materials constitutes a single layer or is disposed in plural layers.

Inorganic particles may be provided on the surface layer or the inside of the separator for the purpose of imparting a function to the separator, and other organic layer may be further formed by coating or laminated on the separator. The separator may contain a crosslinked structure as well. In order to improve the safety performance of the non-aqueous secondary battery, these techniques may be used in combination as required.

By using the above-described separator 170, good input-output characteristics and low self-discharge characteristics, which are required for a lithium ion secondary battery particularly in the above-described high-output application, can be realized. The thickness of the microporous membrane is not particularly limited; however, it is preferably not less than 1 μm from the standpoint of the membrane strength, but preferably 500 μm or less from the standpoint of the permeability. From the standpoint of the use in a high-output application such as a safety test where a relatively large amount of heat is generated and superior self-discharge characteristics than before are required, as well as from the standpoint of the windability using a large battery winding machine, the thickness of the microporous membrane is preferably 5 μm to 30 μm, more preferably 10 μm to 25 μm. The thickness of the microporous membrane is still more preferably 15 μm to 25 μm when importance is placed on attaining both satisfactory short-circuit resistance and satisfactory output performance, or still more preferably 10 μm or greater but less than 15 μm when importance is placed on attaining both high energy density and satisfactory output performance. From the standpoint of conforming to the rapid movement of lithium ions during high output, the porosity is 30% to 90%, more preferably 35% to 80%, still more preferably 40% to 70%. The porosity is particularly preferably 50% to 70% when priority is given to improving the output performance while ensuring safety, or particularly preferably 40% or higher but less than 50% when importance is placed on attaining both satisfactory short-circuit resistance and satisfactory output performance. From the standpoint of the balance between the membrane thickness and the porosity, the air permeability is preferably 1 sec/100 cm$^3$ to 400 sec/100 cm$^3$, more preferably 100 sec/100 cm$^3$ to 350 sec/100 cm$^3$. The air permeability is particularly preferably 150 sec/100 cm$^3$ to 350 sec/100 cm$^3$ when importance is placed on attaining both satisfactory short-circuit resistance and satisfactory output performance, or particularly preferably 100 sec/100 cm$^3$ or higher but less than 150 sec/100 cm$^3$ when priority is given to improving the output performance while ensuring safety. Meanwhile, in cases where a non-aqueous electrolyte solution having a low ionic conductivity is used in combination with the above-described separator, the moving rate of lithium ions is limited not by the structure of the separator but by the ionic conductivity of the electrolyte solution, and there is a tendency that the expected input-output characteristics cannot be obtained. Therefore, the ionic conductivity of the non-aqueous electrolyte solution at 20° C. is preferably 10 mS/cm or higher, and it is also preferably lower than 15 mS/cm. It is noted here, however, that the membrane thickness, the air permeability and the porosity of the separator, as well as the ionic conductivity of the non-aqueous electrolyte solution are not limited to the above-described examples.

<Battery Exterior>

In the present embodiment, the configuration of the battery exterior 110 of the non-aqueous secondary battery 100 is not particularly limited and, for example, a battery exterior composed of a battery can or a laminate film exterior can be used. As the battery can, for example, a square-type, square tube-type, cylindrical-type, elliptical-type, flat-type, coin-type, or button-type metal can made of steel, stainless steel, aluminum, a clad material or the like can be used. As the laminate film exterior, for example, a laminate film having a three-layer structure of hot-melt resin/metal film/resin can be used.

The laminate film exterior can be used as an exterior in a state where two films are laminated with the hot-melt resin side facing inward, or folded such that the hot-melt resin side faces inward, and the ends thereof are sealed by heat sealing. When this laminate film exterior is used, the positive electrode lead 130 (or a positive electrode terminal and a lead tab connected to the positive electrode terminal) may be connected to a positive electrode current collector, and the negative electrode lead 140 (or a negative electrode terminal and a lead tab connected to the negative electrode terminal) may be connected to a negative electrode current collector. In this case, the laminate film exterior may be sealed with the ends of the positive electrode lead 130 and the negative electrode lead 140 (or the lead tabs connected to each of the positive electrode terminal and the negative electrode terminal) being exposed to the outside of the exterior.

<Shape of Non-Aqueous Secondary Battery>

The shape of the non-aqueous secondary battery of the present embodiment is not particularly limited and, for example, a cylindrical shape, an elliptical shape, a square tube shape, a button shape, a coin shape, a flat shape, or a laminate shape can be adopted.

<Method of Producing Non-Aqueous Secondary Battery>

The non-aqueous secondary battery 100 of the present embodiment is produced by a known method using the above-described non-aqueous electrolyte solution, the positive electrode 150 having a positive electrode active material layer on one or both sides of a current collector, the negative electrode 160 having a negative electrode active material layer on one or both sides of a current collector, the battery exterior 110 and, as required, the separator 170.

First, a layered product composed of the positive electrode 150, the negative electrode 160 and, as required, the separator 170 is formed. For example, a mode of forming a layered product having a wound structure by winding the elongated positive electrode 150 and the elongated negative electrode 160 in a layered state with the elongated separator being interposed between the positive electrode 150 and the negative electrode 160; a mode of forming a layered product having a laminated structure in which positive electrode sheets and negative electrode sheets obtained by cutting the positive electrode 150 and the negative electrode 160 into plural sheets having certain area and shape, respectively, are alternately laminated via separator sheets; or a mode of forming a layered product having a laminated structure in which the elongated separator is folded in a zigzag shape, and positive electrode sheets and negative electrode sheets are alternately inserted between the zigzag-folded parts of the separator, can be employed.

Next, the above-described layered product is placed in the battery exterior 110 (battery casing), and the electrolyte solution of the present embodiment is injected into the battery casing to immerse the layered product into the electrolyte solution, after which the battery casing is sealed, whereby the non-aqueous secondary battery of the present embodiment can be produced.

Alternatively, the non-aqueous secondary battery 100 can be produced by preparing a gel-state electrolyte membrane in advance by impregnating a substrate made of a polymer material with the electrolyte solution, forming a layered product having a laminated structure using the positive electrode 150 and the negative electrode 160 that are in a sheet form along with the electrolyte membrane and, as required, the separator 170, and subsequently placing the thus formed laminate in the battery exterior 110.

It is noted here that, when the arrangement of the electrodes is designed such that there is a portion where the outer peripheral edge of the negative electrode active material layer and that of the positive electrode active material layer overlap with each other, or such that a non-facing part of the negative electrode active material layer includes a portion having an excessively small width, misalignment of the electrodes may occur at the time of battery assembly, and this may cause deterioration of the charge-discharge cycle characteristics in the resulting non-aqueous secondary battery. Therefore, the positions of the electrode structures used in the non-aqueous secondary battery are preferably fixed in advance using, for example, a tape such as a polyimide tape, a polyphenylene sulfide tape or a PP tape, or an adhesive.

In the present embodiment, when an acetonitrile-containing non-aqueous electrolyte solution is used, due to its high ionic conductivity, lithium ions released from the positive electrode during initial charging of the non-aqueous secondary battery may diffuse to the entire negative electrode. In the non-aqueous secondary battery, the negative electrode active material layer is generally designed to have a larger area than the positive electrode active material layer. However, if lithium ions are diffused and occluded to a portion of the negative electrode active material layer that does not face the positive electrode active material layer, the lithium ions are not released during initial discharging and thus remain in the negative electrode. Accordingly, the amount of the unreleased lithium ions contributes to an irreversible capacity. For this reason, the non-aqueous secondary battery using an acetonitrile-containing non-aqueous electrolyte solution sometimes has a low initial charging-discharging efficiency.

Meanwhile, when the area of the positive electrode active material layer is the same as or larger than that of the negative electrode active material layer, electric current is likely to be concentrated in the edge portion of the negative electrode active material layer during charging, and this makes the formation of lithium dendrite more likely to occur.

A ratio of the area of the entire negative electrode active material layer with respect to the area of the portion where the positive electrode active material layer and the negative electrode active material layer face each other is not particularly limited; however, for the above-described reasons, it is preferably higher than 1.0 but lower than 1.1, more preferably higher than 1.002 but lower than 1.09, still more preferably higher than 1.005 but lower than 1.08, and particularly preferably higher than 1.01 but lower than 1.08. In the non-aqueous secondary battery using an acetonitrile-containing non-aqueous electrolyte solution, the initial charging-discharging efficiency can be improved by reducing the ratio of the area of the entire negative electrode active material layer with respect to the area of the portion where the positive electrode active material layer and the negative electrode active material layer face each other.

To reduce the ratio of the area of the entire negative electrode active material layer with respect to the area of the portion where the positive electrode active material layer and the negative electrode active material layer face each other means to limit the proportion of the area of the portion of the negative electrode active material layer that does not face the positive electrode active material layer. This enables to reduce as much as possible the amount of lithium ions, which are released from the positive electrode during initial charging, to be occluded in the portion of the negative electrode active material layer that does not face the positive electrode active material layer (i.e., the amount of lithium ions that are not released from the negative electrode during initial discharging and contribute to an irreversible capacity). Therefore, by designing the ratio of the area of the entire negative electrode active material layer with respect to the area of the portion where the positive electrode active material layer and the negative electrode active material layer face each other to be in the above-described range, the initial charging-discharging efficiency of the battery can be improved and the generation of lithium dendrite can be inhibited while improving load characteristics of the battery by using acetonitrile.

The non-aqueous secondary battery 100 of the present embodiment can function as a battery upon initial charging, and is stabilized by partial decomposition of the electrolyte solution during the initial charging. A method of carrying out the initial charging is not particularly limited; however, the initial charging is preferably carried out at 0.001 to 0.3 C, more preferably at 0.002 to 0.25 C, and still more preferably at 0.003 to 0.2 C. The initial charging performed by way of constant-voltage charging in the middle also yields a preferred result. A constant current at which a design capacity is discharged in one hour is 1 C. By setting a broad voltage range in which the lithium salt is involved in an electrochemical reaction, a stable and strong SEI is formed on the electrode surface, and this not only has an effect of inhibiting an increase in the internal resistance but also, without causing the reaction product to be firmly immobilized only on the negative electrode 160, somehow exerts a favorable effect on the members other than the negative electrode 160, such as the positive electrode 150 and the separator 170. Therefore, it is extremely effective to perform the initial charging while taking into consideration the electrochemical reaction of the lithium salt dissolved in the non-aqueous electrolyte solution.

The non-aqueous secondary battery 100 of the present embodiment can also be used as a battery pack in which plural non-aqueous secondary batteries 100 are connected in series or in parallel. From the standpoint of controlling the charge/discharge state of the battery pack, the working voltage range per battery pack is preferably 2 V to 5 V, more preferably 2.5 V to 5 V, particularly preferably 2.75 V to 5 V.

Second Embodiment

The non-aqueous electrolyte solution according to the second embodiment and a non-aqueous secondary battery containing the same will now be described. According to the non-aqueous electrolyte solution of the present embodiment and a non-aqueous secondary battery containing the same, in a non-aqueous electrolyte solution containing a dinitrile compound at a molar ratio of 0.10 or higher with respect to the content of acetonitrile, the two nitrile groups of the dinitrile compound are each coordinated to two molecules of soluble metal complex formed by coordination of acetonitrile to transition metals contained in a positive electrode active material, and the dinitrile compound can be dimerized. In addition, it is presumed that, by this dimerization of the dinitrile compound according to the second embodiment, the molecular weight of the metal complex increased and the metal complex is insolubilized, so that the movement of the metal complex to a negative electrode is inhibited. Therefore, a non-aqueous secondary battery in which deterioration of a negative electrode SEI caused by reduction and precipitation of the metal complex on the negative electrode is inhibited and excellent cycle durability is realized can be provided.

[Non-Aqueous Electrolyte Solution]

The "non-aqueous electrolyte solution" in the present embodiment refers to an electrolyte solution containing water in an amount of 1% by weight or less with respect to a total amount of the electrolyte solution. The electrolyte solution of the present embodiment preferably contains as little water as possible, but may contain a very small amount of water as long as it does not interfere with solving the problems of the present invention. The content of water is preferably 300 ppm by weight or less, more preferably 200 ppm by weight or less, with respect to a total amount of the non-aqueous electrolyte solution. As long as the non-aqueous electrolyte solution has a constitution as prescribed in the present invention, those constituent materials of a known non-aqueous electrolyte solution used in a lithium ion battery can be selected and applied as appropriate.

The non-aqueous electrolyte solution of the present embodiment includes:

an acetonitrile-containing non-aqueous solvent;
a dinitrile compound; and
a lithium salt containing $LiPF_6$ and LiFSI,
wherein the content of acetonitrile is 10% by volume to 70% by volume with respect to a total amount of the non-aqueous solvent, the content of the dinitrile compound is 25% by weight or less with respect to a total amount of the non-aqueous electrolyte solution, the content of the dinitrile compound is 0.10 or higher in terms of molar ratio with respect to the content of acetonitrile, and the content of $LiPF_6$ and that of an imide salt containing LiFSI have a relationship of $0<LiPF_6 \leq$ imide salt in terms of molar concentration.

In the non-aqueous electrolyte solution of the present embodiment, from the standpoint of inhibiting association of the lithium salt and acetonitrile at a low temperature (e.g., −10° C.) and the standpoint of the battery low-temperature cycle characteristics, the content of lithium hexafluorophosphate (abbreviation: $LiPF_6$) and that of an imide salt containing lithium bis(fluorosulfonyl)imide (abbreviation: LiFSI) preferably satisfy $0<LiPF_6 \leq$ imide salt.

In the non-aqueous electrolyte solution of the present embodiment, from the standpoint of inhibiting elution of transition metals from the positive electrode active material, the content of the dinitrile compound is preferably not less than 1% by weight with respect to a total amount of the non-aqueous electrolyte solution.

In the non-aqueous electrolyte solution of the present embodiment, from the standpoint of inhibiting an increase in the viscosity as well as the standpoint of the ionic conductivity, the content of the non-aqueous solvent is preferably more than 70% by volume and/or more than 70% by weight, with respect to a total amount of the non-aqueous solvent and the dinitrile compound.

In the non-aqueous electrolyte solution of the present embodiment, the content of the lithium salt is preferably less than 3 mol in terms of the amount per 1 L of the non-aqueous solvent.

The non-aqueous electrolyte solution of the present embodiment may further contain additives other than the above-described ones.

<Non-Aqueous Solvent>

The term "non-aqueous solvent" used in the present embodiment refers to an element of the electrolyte solution, excluding the lithium salt and various additives.

The non-aqueous solvent in the present embodiment contains acetonitrile.

By incorporating acetonitrile into the non-aqueous solvent, the rapid charging characteristics of the non-aqueous secondary battery can be improved. In constant current-constant voltage (CC-CV) charging of the non-aqueous secondary battery, the capacity per unit time in a CC charging period is larger than the charging capacity per unit time in a CV charging period. When acetonitrile is used in the non-aqueous solvent of the non-aqueous electrolyte solution, not only the CC-chargeable region can be increased (the CC charging time can be extended) but also the charging current can be increased; therefore, the time required for bringing the non-aqueous secondary battery into a fully-charged state from the start of charging can be greatly reduced.

It is noted here that acetonitrile is electrochemically easily reduced and decomposed. In addition, some conventional lithium ion secondary batteries using an acetonitrile-containing non-aqueous electrolyte solution have poor long-term durability. From the results of various verification experiments, the reason why a lithium ion secondary battery using an acetonitrile-containing non-aqueous electrolyte solution has poor long-term durability is considered as follows:

Since the nitrile group of acetonitrile has a high metal coordination ability, the nitrile group forms a complex with and stabilizes transition metals contained in a positive electrode active material and thereby facilitates metal elution. Metal ions eluted into the non-aqueous electrolyte solution are reduced and precipitated on the negative electrode side, damaging the negative electrode SEI. As a result, not only the reductive decomposition of the solvent on the negative electrode is facilitated and the irreversible capacity is increased, but also the reductively decomposed solvent is accumulated on the negative electrode and the internal resistance increased. This phenomenon is facilitated as the temperature increases and, therefore, has a large effect on the high-temperature durability as well.

The content of acetonitrile is 10% by volume to 70% by volume with respect to a total amount of the non-aqueous solvent.

When the content of acetonitrile is 10% by volume or more with respect to a total amount of the non-aqueous solvent, the ionic conductivity of the non-aqueous electrolyte solution is increased, so that high output characteristics can be exerted and the lithium salt can be dissolved at a high concentration. When the content of acetonitrile is 70% by volume or less with respect to a total amount of the non-aqueous solvent, favorable charge-discharge cycle characteristics and other battery characteristics can be obtained.

The content of acetonitrile is preferably 12% by volume to 50% by volume, more preferably 15% by volume to 35% by volume, with respect to a total amount of the non-aqueous solvent.

Examples of other solvent used in combination as the non-aqueous solvent include: alcohols, such as methanol and ethanol; and aprotic solvents other than acetonitrile. Thereamong, the non-aqueous solvent preferably contains an aprotic solvent other than acetonitrile.

The aprotic solvent other than acetonitrile may be, for example, a cyclic carbonate, a linear carbonate, fluoroethylene carbonate, a lactone, a sulfur compound, a cyclic ether, a linear ether, a fluorinated ether, a mononitrile other than acetonitrile, an alkoxy group-substituted nitrile, a cyclic nitrile, a linear ester, a ketone, or a halide.

Specific examples of these aprotic solvents other than acetonitrile include:

saturated cyclic carbonates, such as ethylene carbonate, propylene carbonate, 1,2-butylene carbonate, trans-2,3-butylene carbonate, cis-2,3-butylene carbonate, 1,2-pentylene carbonate, trans-2,3-pentylene carbonate, and cis-2,3-pentylene carbonate;

unsaturated cyclic carbonates, such as vinylene carbonate, 4,5-dimethylvinylene carbonate, and vinylethylene carbonate;

linear carbonates, such as ethyl methyl carbonate, dimethyl carbonate, diethyl carbonate, methyl propyl carbonate, methyl isopropyl carbonate, dipropyl carbonate, methyl butyl carbonate, dibutyl carbonate, ethyl propyl carbonate, and methyl trifluoroethyl carbonate;

fluoroethylene carbonates, such as 4-fluoro-1,3-dioxolan-2-one, 4,4-difluoro-1,3-dioxolan-2-one, cis-4,5-difluoro-1,3-dioxolan-2-one, trans-4,5-difluoro-1,3-dioxolan-2-one, 4,4,5-trifluoro-1,3-dioxolan-2-one, 4,4,5,5-tetrafluoro-1,3-dioxolan-2-one, 4,4,5-trifluoro-5-methyl-1,3-dioxolan-2-one, and 4-(2,2,2-trifluoroethoxy)-1,3-dioxolan-2-one;

lactones, such as γ-butyrolactone, α-methyl-γ-butyrolactone, γ-valerolactone, γ-caprolactone, δ-valerolactone, δ-caprolactone, and ε-caprolactone;

sulfur compounds, such as ethylene sulfite, propylene sulfite, butylene sulfite, pentene sulfite, sulfolane, 3-sulfolane, 3-methyl sulfolane, 1,3-propane sultone, 1,4-butane sultone, 1-propene-1,3-sultone, dimethyl sulfoxide, tetramethylene sulfoxide, and ethylene glycol sulfite;

cyclic ethers, such as tetrahydrofuran, 2-methyl tetrahydrofuran, 1,4-dioxane, and 1,3-dioxane;

linear ethers, such as dimethoxyethane, diethyl ether, 1,3-dioxolan, diglyme, triglyme, and tetraglyme;

fluorinated ethers, such as $Rf^{20}$—$OR^{21}$ (wherein, $Rf^{20}$ represents a fluorine atom-containing alkyl group, and $R^{21}$ represents an organic group optionally containing a fluorine atom);

mononitriles other than acetonitrile, such as propionitrile, butyronitrile, valeronitrile, benzonitrile, and acrylonitrile;

alkoxy group-substituted nitriles, such as methoxyacetonitrile and 3-methoxypropionitrile;

cyclic nitriles, such as benzonitrile;

linear esters, such as methyl propionate, ethyl propionate, ethyl acetate, propyl propionate, and 2,2-difluoroethyl acetate; and ketones, such as acetone, methyl ethyl ketone, and methyl isobutyl ketone; and halides, such as fluorinated products of the above-exemplified compounds.

In the present embodiment, these aprotic solvents other than acetonitrile may be used singly, or in combination of two or more thereof.

From the standpoint of improving the stability of the non-aqueous electrolyte solution, in the non-aqueous solvent of the present embodiment, it is preferable to use at least one of a saturated cyclic carbonate, an unsaturated cyclic carbonate, and a linear carbonate in combination. From the same standpoint, in the non-aqueous solvent of the present embodiment, it is more preferable to use a saturated cyclic carbonate and an unsaturated cyclic carbonate in combination, and it is still more preferable to use all of a saturated cyclic carbonate, an unsaturated cyclic carbonate, and a linear carbonate.

The saturated cyclic carbonate used in combination is particularly preferably at least one selected from the group consisting of ethylene carbonate and fluoroethylene carbonate. The content of the saturated cyclic carbonate is preferably 0.5% by volume to 50% by volume, more preferably 1% by volume to 25% by volume, with respect to a total amount of the non-aqueous solvent.

The unsaturated cyclic carbonate used in combination is particularly preferably vinylene carbonate. The content of the unsaturated cyclic carbonate is preferably 0.5% by volume to 10% by volume, more preferably 1% by volume to 5% by volume, with respect to a total amount of the non-aqueous solvent. When the content of the unsaturated cyclic carbonate is in this range, not only a strong negative electrode SEI can be formed, but also gas swelling during charging and discharging can be inhibited.

The linear carbonate is particularly preferably at least one selected from the group consisting of dimethyl carbonate, diethyl carbonate, and methyl ethyl carbonate. The content of the linear carbonate is preferably 5% by volume to 50% by volume, more preferably 10% by volume to 40% by volume, with respect to a total amount of the non-aqueous solvent.

The non-aqueous solvent of the present embodiment may also contain a sulfur compound. The sulfur compound used in combination is particularly preferably at least one selected from the group consisting of ethylene sulfite, propylene sulfite, and 1,3-propane sultone. The content of the sulfur compound is preferably 0.1% by volume to 10% by volume, more preferably 0.5% by volume to 5% by volume, with respect to a total amount of the non-aqueous solvent. When the content of the sulfur compound is in this range, a high-quality negative electrode SEI can be formed.

<Dinitrile Compound>

The non-aqueous electrolyte solution of the present embodiment contains a dinitrile compound represented by the following Formula (1):

[Chem. 7]

$$NC-R-CN \quad (1)$$

{wherein, R represents a straight-chain or branched divalent aliphatic alkyl group having 1 to 12 carbon atoms and optionally containing oxygen atoms}.

Similarly to acetonitrile, the dinitrile compound used in the present invention has nitrile groups with a high metal coordination ability, and is coordinated to transition metals contained in a positive electrode active material. It is presumed that the two nitrile groups of the dinitrile compound are each coordinated to two molecules of soluble metal complex formed by coordination of acetonitrile to the transition metals contained in the positive electrode active material, and the dinitrile compound can be dimerized, whereby the molecular weight of the metal complex increased and the metal complex is insolubilized, so that the movement of the metal complex to a negative electrode is inhibited. Therefore, a non-aqueous secondary battery in which deterioration of a negative electrode SEI caused by reduction and precipitation of the metal complex on the negative electrode is inhibited and excellent cycle durability is realized can be provided.

In Formula (1), the number of carbon atoms in the straight-chain or branched divalent aliphatic alkyl group R is preferably 1 to 12, more preferably 1 to 10, particularly preferably 1 to 8.

Specific examples of a straight-chain dinitrile compound include malononitrile, succinonitrile, glutaronitrile, adiponitrile, 1,5-dicyanopentane, 1,6-dicyanohexane, 1,7-dicyanoheptane, 1,8-dicyanooctane, 1,9-dicyanononane, 1,10-dicyanodecane, and 1,12-dicyanododecane.

Specific examples of a branched dinitrile compound include methylsuccinonitrile, tetramethylsuccinonitrile, 2-methylglutaronitrile, 2,4-dimethylglutaronitrile, 1,4-dicyanopentane, 1,4-dicyanoheptane, 1,5-dicyanoheptane, 2,6-dicyanoheptane, 1,7-dicyanooctane, 2,7-dicyanooctane, 1,8-dicyanononane, 2,8-dicyanononane, and 1,6-dicyanodecane.

Specific examples of a dinitrile compound containing oxygen atoms include ethylene glycol bis(propionitrile) ether, diethylene glycol bis(2-cyanoethyl) ether, triethylene glycol bis(2-cyanoethyl) ether, tetraethylene glycol bis(2-cyanoethyl) ether, 1,3-bis(2-cyanoethoxy)propane, 1,4-bis(2-cyanoethoxy)butane, and 1,5-bis(2-cyanoethoxy)pentane.

Among these specific examples of the dinitrile compound, malononitrile, succinonitrile, glutaronitrile, adiponitrile, methylsuccinonitrile, 2-methylglutaronitrile, and ethylene glycol bis(propionitrile) ether are preferred; succinonitrile, glutaronitrile, methylsuccinonitrile, 2-methylglutaronitrile, and ethylene glycol bis(propionitrile) ether are more preferred; and succinonitrile, methylsuccinonitrile, and ethylene glycol bis(propionitrile) ether are still more preferred. These compounds may be used singly, or in combination of two or more thereof.

In the second embodiment, the content of the dinitrile compound in the non-aqueous electrolyte solution is 0.10 or higher in terms of molar ratio with respect to the content of acetonitrile.

Generally, transition metals such as Ni form 4 to 6-coordinate complex compounds in a stable manner. Accordingly, it is presumed that any of the following structures is generated when two molecules of soluble metal complex formed by coordination of acetonitrile to a transition metal is dimerized by one molecule of a dinitrile compound:

[Chem. 8]

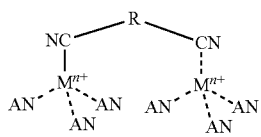

•4-coordinate + 4-coordinate
dinitrile compound/acetonitrile = 1/6(0.17)

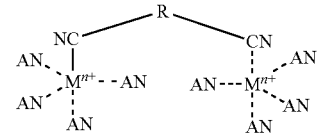

•5-coordinate + 5-coordinate
dinitrile compound/acetonitrile = 1/8(0.13)

[Chem. 9]

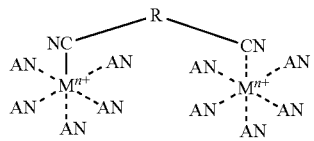

•6-coordinate + 6-coordinate
dinitrile compound/acetonitrile = 1/10(0.10)

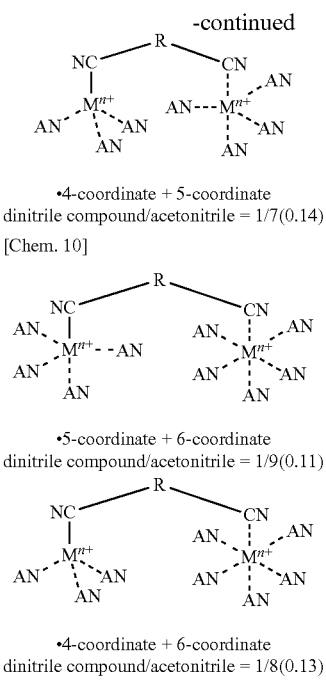

• 4-coordinate + 5-coordinate
dinitrile compound/acetonitrile = 1/7(0.14)

[Chem. 10]

• 5-coordinate + 6-coordinate
dinitrile compound/acetonitrile = 1/9(0.11)

• 4-coordinate + 6-coordinate
dinitrile compound/acetonitrile = 1/8(0.13)

AN: acetonitrile
NC---R---CN: dinitrile compound

Therefore, in order to dimerize and insolubilize such a soluble metal complex formed by coordination of acetonitrile to a transition metal, the content of the dinitrile compound is 0.10 or higher, preferably 0.17 or higher, more preferably 0.25 or higher, in terms of molar ratio with respect to the content of acetonitrile. By adjusting the content of the dinitrile compound to be in this range, elution of a transition metal from a positive electrode active material caused by acetonitrile can be inhibited.

The content of the dinitrile compound in the non-aqueous electrolyte solution is 25% by weight or less, preferably 10% by weight or less, more preferably 5% by weight or less, with respect to a total amount of the non-aqueous electrolyte solution. The content of the dinitrile compound in the non-aqueous electrolyte solution is also preferably not less than 0.5% by weight, more preferably not less than 1% by weight, still more preferably not less than 1.5% by weight, particularly preferably not less than 3% by weight, with respect to a total amount of the non-aqueous electrolyte solution. By adjusting the content of the dinitrile compound to be in the above-described range, elution of a transition metal from a positive electrode active material can be inhibited and favorable cycle characteristics and other battery characteristics can be obtained while maintaining the properties of acetonitrile, such as high ionic conductivity and high output characteristics.

In the present embodiment, the content of the non-aqueous solvent is preferably higher than 70% by volume, more preferably higher than 73% by volume, still more preferably higher than 76% by volume, with respect to a total amount of the non-aqueous solvent and the dinitrile compound.

In the present embodiment, the content of the non-aqueous solvent is preferably higher than 70% by weight, more preferably higher than 73% by weight, still more preferably higher than 76% by weight, with respect to a total amount of the non-aqueous solvent and the dinitrile compound.

In the present embodiment, when the content of the non-aqueous solvent is in the above-described range, not only an excessive increase in the viscosity caused by the dinitrile compound can be inhibited, but also the ionic conductivity increased and high output characteristics tend to be exerted.

<Lithium Salt>

The non-aqueous electrolyte solution of the present embodiment contains, as the lithium salt, $LiPF_6$ and LiFSI (abbreviation) that can be represented by a formula $LiN(SO_2F)_2$. Further, the content of $LiPF_6$ and that of an imide salt containing LiFSI have a relationship of $0 < LiPF_6 \leq $ imide salt in terms of molar concentration.

When the non-aqueous solvent contains acetonitrile, since the saturation concentration of the imide salt with respect to acetonitrile is higher than that of $LiPF_6$, the non-aqueous solvent preferably contains the imide salt at a molar concentration that satisfies $0 < LiPF_6 \leq $ imide salt as this can inhibit association and precipitation of the lithium salt with acetonitrile at a low temperature.

$LiPF_6$ is a fluorine-containing inorganic lithium salt having a phosphorus atom and facilitates the release of free fluorine atoms.

As the lithium salt in the present embodiment, an imide salt represented by $LiN(SO_2C_mF_{2m+1})_2$ {wherein, m represents an integer of 1 to 8} can be used in combination with LiFSI.

The content of the lithium salt in the non-aqueous electrolyte solution of the present embodiment is preferably less than 3 mol in terms of the amount per 1 L of the non-aqueous solvent. When the content of the lithium salt is in this range, not only an excessive increase in the viscosity is inhibited, but also the ionic conductivity is increased and high output characteristics tend to be exerted.

In the present embodiment, the amount of a lithium salt other than $LiPF_6$ and LiFSI to be added to the non-aqueous electrolyte solution may be set as appropriate in a range of, for example, 0.01 mol to 0.5 mol in terms of the amount per 1 L of the non-aqueous solvent.

(Imide Salt)

The imide salt according to the second embodiment is the same as in the first embodiment.

PTL 5 describes that it is preferable to incorporate an imide salt at a molar concentration satisfying $LiPF_6 >$ imide salt, and it is thus presumably difficult to obtain excellent low-temperature characteristics using the non-aqueous electrolyte solution disclosed in PTL 5.

Further, in PTL 6, incorporation of LiFSI as a lithium salt is not assumed. Therefore, it is presumably difficult to obtain excellent low-temperature characteristics using the non-aqueous electrolyte solution disclosed in PTL 6.

(Fluorine-Containing Inorganic Lithium Salt)

A fluorine-containing inorganic lithium salt according to the second embodiment is the same as in the first embodiment.

(Organic Lithium Salt)

An organic lithium salt according to the second embodiment is the same as in the first embodiment.

(Other Lithium Salts)

Other lithium salts according to the second embodiment are the same as in the first embodiment.

<Electrode Protection Additive>

An electrode protection additive according to the second embodiment is the same as in the first embodiment.

(Other Optional Additives)

Other optional additives according to the second embodiment are the same as in the first embodiment.

<Ionic Conductivity of Non-Aqueous Electrolyte Solution>

In the non-aqueous secondary battery, an increase in the electrode thickness can reduce the amount of members not contributing to the capacity and thus increase the energy density; however, when this is combined with the use of an electrolyte solution having a low ionic conductivity, the moving rate of lithium ions is limited by the ionic conductivity of the non-aqueous electrolyte solution, and the desired input-output characteristics are not obtained in some cases. In addition, when a separator of the below-described preferred mode is used in combination with a non-aqueous electrolyte solution having a low ionic conductivity in a non-aqueous secondary battery, the moving rate of lithium ions is limited by the ionic conductivity of the non-aqueous electrolyte solution, and the desired input-output characteristics are not obtained in some cases. Therefore, the ionic conductivity of the non-aqueous electrolyte solution of the present embodiment is preferably 10 mS/cm or higher, more preferably 15 mS/cm or higher, still more preferably 20 mS/cm or higher.

<Specific Gravity of Non-Aqueous Electrolyte Solution>

When the non-aqueous electrolyte solution has a high specific gravity, not only the viscosity of the electrolyte solution is high and this causes a reduction in the ionic conductivity, but also the wettability of the electrolyte solution to a separator is low and this tends to result in insufficient impregnation of the separator with the electrolyte solution. Thus, a high specific gravity contributes to an increase in the battery internal resistance, adversely affects the battery characteristics such as cycle characteristics, and potentially causes a problem in the electrolyte solution injection process at the time of producing a lithium battery. Therefore, the specific gravity of the non-aqueous electrolyte solution of the present embodiment is preferably 1.5 or less under normal temperature and normal pressure.

[Non-Aqueous Secondary Battery]

According to another mode of the present invention, a non-aqueous secondary battery containing the non-aqueous electrolyte solution of the present embodiment is provided.

The non-aqueous secondary battery of the second embodiment is the same as that of the first embodiment.

The elements constituting the non-aqueous secondary battery of the present embodiment will now be described one by one.

[Positive Electrode]

In the non-aqueous secondary battery of the present embodiment, the positive electrode has a positive electrode active material layer on one or both sides of a positive electrode current collector.

<Positive Electrode Active Material Layer>

The positive electrode active material layer contains a positive electrode active material, and may further contain a conductive aid and a binder as required.

(Positive Electrode Active Material)

The positive electrode active material preferably contains a material capable of occluding and releasing lithium ions. When such a material is used, a high voltage and a high energy density tend to be obtained, which is preferred.

Examples of the positive electrode active material include:

lithium cobalt oxides typified by $LiCoO_2$;

lithium manganese oxides typified by $LiMnO_2$, $LiMn_2O_4$ and $Li_2Mn_2O_4$;

lithium nickel oxides typified by $LiNiO_2$; and lithium-containing composite metal oxides represented by $Li_zMO_2$ {wherein, M contains at least one transition metal element selected from the group consisting of Ni, Mn, and Co and represents two or more metal elements selected from the group consisting of Ni, Mn, Co, Al, and Mg; and z represents a number of larger than 0.9 but smaller than 1.2}, which are typified by $LiNi_{1/3}Co_{1/3}Mn_{1/3}O_2$, $LiNi_{0.5}Co_{0.2}Mn_{0.3}O_2$, $LiNi_{0.6}Co_{0.2}Mn_{0.2}O_2$, $LiNi_{0.8}Co_{0.1}Mn_{0.1}O_2$, $LiNi_{0.8}Co_{0.2}O_2$, $LiNi_{0.75}Co_{0.15}Mn_{0.15}O_2$, $LiNi_{0.8}Co_{0.1}Mn_{0.1}O_2$, $LiNi_{0.85}Co_{0.075}Mn_{0.075}O_2$, $LiNi_{0.8}Co_{0.15}Al_{0.05}O_2$, $LiNi_{0.81}Co_{0.1}Al_{0.09}O_2$, and $LiNi_{0.85}Co_{0.1}Al_{0.05}O_2$.

The positive electrode active material of the present embodiment preferably contains a lithium-containing metal oxide represented by the following Formula (d) since this allows occlusion and release of lithium ions to occur in a reversible and stable manner and can achieve a high energy density:

$$Li_pNi_qCo_rM^1_sM^2_tO_u \quad (d)$$

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.4<q<1$, $0<r<0.4$, $0<s<0.4$, $0 \leq t<0.3$, $0.7 \leq q+r+s+t \leq 1.2$, and $1.8<u<2.2$ are satisfied; and p is a value determined by a charge-discharge state of the battery}.

Particularly, the lithium-containing metal oxide represented by Formula (d) preferably has a high Ni content ratio q and satisfies $0.7<q<1$, $0<r<0.2$, and $0<s<0.2$, since both a reduction in the usage of Co, which is a rare metal, and an increase in the energy density are thereby attained.

On the other hand, cycle deterioration under a high temperature environment tends to progress as the Ni content ratio increases in the lithium-containing metal oxide.

The positive electrode active material may be a lithium-containing compound other than the lithium-containing metal oxide represented by Formula (d), and is not particularly limited as long as it contains lithium. Examples of such a lithium-containing compound include: composite oxides containing lithium and a transition metal element; metal chalcogenides containing lithium; metal phosphate compounds containing lithium and a transition metal element; and metal silicate compounds containing lithium and a transition metal element. From the standpoint of obtaining a higher voltage, the lithium-containing compound is particularly preferably a metal phosphate compound that contains lithium and at least one transition metal element selected from the group consisting of Co, Ni, Mn, Fe, Cu, Zn, Cr, V, and Ti.

More specific examples of the lithium-containing compound include compounds represented by any of the following Formulae (Xa), (Xb), and (Xc):

$$Li_vM^ID_2 \quad (Xa)$$

{wherein, D represents a chalcogen element; $M^I$ represents one or more transition metal elements; and v is determined by a charge-discharge state of the battery and represents a number of 0.05 to 1.10};

$$Li_wM^{II}PO_4 \quad (Xb)$$

{wherein, D represents a chalcogen element; $M^{II}$ represents one or more transition metal elements; and w is determined by a charge-discharge state of the battery and represents a number of 0.05 to 1.10}; and $$Li_tM^{III}_uSiO_4 \quad (Xc)$$

{wherein, D represents a chalcogen element; $M^{III}$ represents one or more transition metal elements; t is determined by a charge-discharge state of the battery and represents a number of 0.05 to 1.10; and u represent a number of 0 to 2}.

The lithium-containing compounds represented by Formula (Xa) have a layered structure, while the compounds represented by Formulae (Xb) or (Xc) have an olivine structure. For the purposes of structure stabilization and the like, these lithium-containing compounds may be, for example, those in which some of the transition metal elements are substituted with Al, Mg, or other transition metal element, those in which these metal elements are incorporated into the crystal grain boundaries, those in which some of the oxygen atoms are substituted with fluorine atoms or the like, or those in which the surface of the positive electrode active material is at least partially coated with other positive electrode active material.

As the positive electrode active material in the present embodiment, any of the above-described lithium-containing compounds may be used, and other positive electrode active material may be used in combination with the lithium-containing compound. Examples of the other positive electrode active material include: metal oxides and metal chalcogenides which have a tunnel structure and a layered structure; sulfur; and conductive polymers. Examples of the metal oxides and metal chalcogenides which have a tunnel structure and a layered structure include oxides, sulfides, and selenides of metals other than lithium, which are typified by $MnO_2$, $FeO_2$, $FeS_2$, $V_2O_5$, $V_6O_{13}$, $TiO_2$, $TiS_2$, $MoS_2$, and $NbSe_2$. The conductive polymers are typified by, for example, polyaniline, polythiophene, polyacetylene, and polypyrrole.

The above-described other positive electrode active material may be used singly or in combination of two or more thereof, and is not particularly limited. However, the positive electrode active material layer preferably contains at least one transition metal element selected from Ni, Mn, and Co, since this allows occlusion and release of lithium ions to occur in a reversible and stable manner and can achieve a high energy density.

When a lithium-containing compound and other positive electrode active material are used in combination as the positive electrode active material, their usage ratio, namely the usage ratio of the lithium-containing compound with respect to the whole positive electrode active material, is preferably 80% by weight or higher, more preferably 85% by weight or higher.

(Conductive Aid) The conductive aid according to the second embodiment is the same as in the first embodiment.
(Binder)
The binder according to the second embodiment is the same as in the first embodiment.
<Positive Electrode Current Collector>
The positive electrode current collector according to the second embodiment is the same as in the first embodiment.
<Formation of Positive Electrode Active Material Layer>
The positive electrode active material layer according to the second embodiment is formed in the same manner as in the first embodiment.
[Negative Electrode]
The negative electrode according to the second embodiment is the same as in the first embodiment.
<Si Material-Containing Negative Electrode>
In the present embodiment, a Si material, particularly $SiO_x$ (wherein, $0.5 \leq x \leq 1.5$), may be incorporated as a negative electrode active material. The Si material may be in any form of a crystalline material, a low crystalline material, and an amorphous material. When such a Si material is used as the negative electrode active material, it is preferable to coat the surface of the active material with a conductive material since the conductivity between particles of the active material is thereby improved.

Si (silicon) has an operating potential of about 0.5 V (vs $Li/Li^+$), which is slightly higher than the operating potential of graphite of about 0.05 V (vs. $Li/Li^+$). Accordingly, the use of a Si material reduces the risk of lithium electrodeposition. Acetonitrile used in the non-aqueous solvent of the present embodiment may undergo a reductive reaction with lithium metal to cause gas generation. Therefore, a negative electrode active material that hardly causes lithium electrodeposition is preferred when it is to be used in combination with an acetonitrile-containing electrolyte solution.

On the other hand, a negative electrode active material having an excessively high operating potential reduces the energy density of the battery; therefore, from the standpoint of improving the energy density, the operating potential of the negative electrode active material is preferably lower than 0.4 V vs $Li/Li^+$.

The content of the Si material is preferably in a range of 0.1% by weight to 100% by weight, more preferably in a range of 1% by weight to 80% by weight, still more preferably in a range of 3% by weight to 60% by weight, with respect to a total amount of the negative electrode active material layer of the present embodiment. By adjusting the content of the Si material to be in this range, a balance between an increase in the capacity and the charge-discharge cycle performance can be ensured in the non-aqueous secondary battery.

[Separator]
A separator according to the second embodiment is the same as in the first embodiment.
<Battery Exterior>
A battery exterior according to the second embodiment is the same as in the first embodiment.
<Shape of Non-Aqueous Secondary Battery>
The shape of the non-aqueous secondary battery according to the second embodiment is the same as in the first embodiment.
<Method of Producing Non-Aqueous Secondary Battery>
A method of producing the non-aqueous secondary battery according to the second embodiment is the same as in the first embodiment.

Modes for carrying out the present invention have been described thus far; however, the present invention is not limited to the above-described embodiments. The present invention can be carried out with various modifications within the gist of the present invention.

EXAMPLES

The present invention will now be described in more detail by way of Examples; however, the present invention is not limited to the below-described Examples.

First Embodiment (1) Preparation of Non-Aqueous Electrolyte Solutions
Non-aqueous electrolyte solutions (S1) to (S31) were prepared by mixing various non-aqueous solvents and additives at prescribed concentrations in an inert atmosphere and further adding various lithium salts such that the resultants each have a prescribed concentration thereof. For these non-aqueous electrolyte solutions, the composition and the ionic conductivity are shown in Table 1.

The abbreviations used for non-aqueous solvents, lithium salts and additives in Table 1 have the below-described meanings. The molar concentration of each lithium salt in Table 1 indicates a molar concentration per 1 L of the respective non-aqueous solvents, and the amount (% by weight) of each additive in Table 1 indicates an amount (% by weight) with respect to a total amount of the respective non-aqueous electrolyte solutions. A value in % by volume and a value in % by weight are interconvertible using the specific gravity values (25° C.) of the respective non-aqueous solvents, lithium salt, and additive.

(Non-Aqueous Solvents)
  AcN: acetonitrile
  EMC: ethyl methyl carbonate
  DEC: diethyl carbonate
  DFA: 2,2-difluoroethyl acetate
  MBL: α-methyl-γ-butyrolactone
  EC: ethylene carbonate
  ES: ethylene sulfite
  VC: vinylene carbonate (Lithium Salts)
  $LiPF_6$: lithium hexafluorophosphate
  LiFSI: lithium bis(fluorosulfonyl)imide ($LiN(SO_2F)_2$)
  LiTFSI: lithium bis(trifluoromethanesulfonyl)imide ($LiN(SO_2CF_3)_2$)

(Additives)
  SN: succinonitrile
  MeSN: methylsuccinonitrile
  Pyridine: pyridine
  CAF: caffeine
  V0044: triethoxyvinylsilane
  $FSO_3CH_3$: methyl fluorosulfate
  PN: propionitrile

TABLE 1

| Non-aqueous electrolyte solution | Non-aqueous solvent (% by volume) | | | | | | | | Lithium salt (mol/1 L solvent) | |
|---|---|---|---|---|---|---|---|---|---|---|
| | AcN | EMC | DEC | DFA | MBL | EC | ES | VC | LiPF6 | LiFSI |
| S1 | 20 | 19 | | 54.5 | | | 4 | 2.5 | 0.3 | 1 |
| S2 | 47 | 19 | | 28 | | | 4 | 2 | 0.3 | 1 |
| S3 | | 69 | | | | 29 | | 2 | 1 | |
| S4 | 5 | 78.7 | | | | 10 | 3.8 | 2.5 | 0.3 | 1.5 |
| S5 | 5 | 78.7 | | | | 10 | 3.8 | 2.5 | 0.3 | 1.5 |
| S6 | 5 | 78.7 | | | | 10 | 3.8 | 2.5 | 0.3 | 1.5 |
| S7 | 10 | 73.7 | | | | 10 | 3.8 | 2.5 | 0.3 | 1.5 |
| S8 | 10 | 73.7 | | | | 10 | 3.8 | 2.5 | 0.3 | 1.5 |
| S9 | 10 | 73.7 | | | | 10 | 3.8 | 2.5 | 0.3 | 1.25 |
| S10 | 10 | 62.7 | | | | 21 | 3.8 | 2.5 | 0.3 | 1.5 |
| S11 | 20 | 63.7 | | | | 10 | 3.8 | 2.5 | 0.3 | 1.5 |
| S12 | 5 | 67.7 | | | | 21 | 3.8 | 2.5 | 0.3 | 1.5 |
| S13 | 10 | 83.2 | | | | | 3.8 | 3 | 0.3 | 1.5 |
| S14 | 10 | 83.2 | | | | | 3.8 | 3 | 0.3 | 1.5 |
| S15 | 49 | | | 28 | | 21 | | 2 | | |
| S16 | 49 | 28 | | | | 21 | | 2 | | |
| S17 | 47 | | | 28 | 19 | | 4 | 2 | | |
| S18 | 48.5 | 28 | | | | 21 | | 2.5 | 0.3 | 1 |
| S19 | 5 | 71.5 | | | | 21 | | 2.5 | 0.3 | 1 |
| S20 | 20 | | 56.5 | | | 21 | | 2.5 | 0.3 | |
| S21 | 20 | | 56.5 | | | 21 | | 2.5 | 0.3 | |
| S22 | 20 | 63.7 | | | | 10 | 3.8 | 2.5 | 0.3 | 1.5 |
| S23 | 20 | 63.7 | | | | 10 | 3.8 | 2.5 | 0.3 | 1.5 |
| S24 | 20 | 63.7 | | | | 10 | 3.8 | 2.5 | 0.3 | 1.5 |
| S25 | 10 | 73.7 | | | | 10 | 3.8 | 2.5 | 0.3 | 1 |
| S26 | 10 | 73.7 | | | | 10 | 3.8 | 2.5 | 0.3 | 1 |
| S27 | 20 | 63.7 | | | | 10 | 3.8 | 2.5 | 0.3 | 1.5 |
| S28 | 5 | 71.2 | | | | 21 | | 2.8 | 0.3 | 1 |
| S29 | 60 | 18 | | | | 20 | | 2 | 0.3 | 1 |
| S30 | 10 | 64 | | | | 20 | 4 | 2 | 0.3 | 1 |
| S31 | 10 | 64 | | | | 20 | 4 | 2 | 0.3 | 1 |

| Non-aqueous electrolyte solution | Additive (% by weight) | | | | | | | Ionic conductivity (mS/cm) |
|---|---|---|---|---|---|---|---|---|
| | LiTFSI | SN | MeSN | Pyridine | CAF | V0044 | FSO3CH3 | PN | |
| S1 | | | | | | 0.1 | 0.005 | 0.00008 | 14.1 |
| S2 | | | | | | 0.1 | 0.020 | 0.00020 | 22.0 |
| S3 | | | | | | | 0 | 0 | 9.0 |
| S4 | | | | | | | 0.0075 | 0.00002 | 10.1 |
| S5 | | | | | 0.1 | | 0.0075 | 0.00002 | 10.4 |
| S6 | | 3.2 | | | 0.1 | | 0.0075 | 0.00002 | 10.1 |
| S7 | | 3.2 | | | 0.1 | | 0.0075 | 0.00004 | 10.8 |
| S8 | | 1.6 | | | | | 0.0075 | 0.00004 | 10.8 |
| S9 | | | | | | | 0.00625 | 0.00004 | 11.5 |
| S10 | | 3.2 | | | 0.1 | | 0.0075 | 0.00004 | 11.1 |
| S11 | | 3.2 | | | | | 0.0075 | 0.00008 | 13.5 |
| S12 | | | | | | | 0.0075 | 0.00002 | 10.3 |
| S13 | | | | | 0.1 | | 0.0075 | 0.00004 | 11.1 |
| S14 | | 1.6 | | | 0.1 | | 0.0075 | 0.00004 | 10.9 |
| S15 | | | | | | 0.1 | 0 | 0.000196 | 24.5 |

TABLE 1-continued

| | | | | | | |
|---|---|---|---|---|---|---|
| S16 | | | | 0.5 | 0 | 0.000196 | 24.3 |
| S17 | | | | 0.1 | 0 | 0.000188 | 24.9 |
| S18 | | | | | 0.005 | 0.000194 | 22.8 |
| S19 | | | | | 0.005 | 0.00002 | 11.1 |
| S20 | 1 | | | | 0 | 0.00008 | 10.5 |
| S21 | 1 | 1.6 | | | 0 | 0.00008 | 10.1 |
| S22 | | | | | 0.0075 | 0.00008 | 14.0 |
| S23 | | 3.2 | | | 0.0075 | 0.00008 | 13.1 |
| S24 | | | 0.1 | | 0.0075 | 0.00008 | 13.9 |
| S25 | | | | | 0.005 | 0.00004 | 11.5 |
| S26 | | 1.9 | | | 0.005 | 0.00004 | 11.3 |
| S27 | | 7.5 | | | 0.0075 | 0.00008 | 12.6 |
| S28 | | | | | 0.005 | 0.00002 | 10.3 |
| S29 | | | | | 0.005 | 0.00024 | 28.0 |
| S30 | | | | | 0.005 | 0.00004 | 12.3 |
| S31 | | | 0.1 | | 0.005 | 0.00004 | 12.0 |

(2) Production of Coin-Type and Small-Sized Non-Aqueous Secondary Batteries (2-1) Production of Positive Electrodes (2-1-1) Production of Positive Electrode (I-P1)

A composite oxide ($LiNi_{0.8}Mn_{0.1}Co_{0.1}O_2$) of lithium, nickel, manganese, and cobalt as core particles of a positive electrode active material and zirconium oxide ($ZrO_2$) as a coating agent are mixed using a Henschel mixer. The mixing amount of zirconium oxide is adjusted to be 0.05% by mole in terms of zirconium with respect to a total molar amount of nickel, cobalt, and manganese. The thus obtained mixture is calcined at 580° C. for 10 hours in the atmosphere.

A positive electrode active material composite obtained in the above-described manner, an acetylene black powder, and polyvinylidene fluoride (PVDF) were mixed as (A) a positive electrode active material, (B) a conductive aid, and a binder, respectively, at a mass ratio of 94:3:3 to obtain a positive electrode mixture.

To the thus obtained positive electrode mixture, N-methyl-2-pyrrolidone was added as a solvent such that a solid content of 68% by weight was obtained, and the resultant was further mixed to prepare a positive electrode mixture-containing slurry. One side of an aluminum foil having a thickness of 15 μm and a width of 280 mm, which served as a positive electrode current collector, was coated with the positive electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 130° C. for 8 hours. Thereafter, the electrode roll was rolled using a roll press such that the resulting positive electrode active material layer had a density of 2.9 g/cm$^3$, whereby a positive electrode (I-P1) composed of the positive electrode active material layer and the positive electrode current collector was obtained. The basis weight excluding the positive electrode current collector was 16.6 mg/cm$^2$.

(2-1-2) Production of Positive Electrode (I-P2)

A positive electrode (I-P2) was produced in the same manner as in (2-1-1), except that aluminum oxide ($Al_2O_3$) was used as the coating agent, and the mixing amount of aluminum oxide was adjusted to be 3.6% by mole in terms of aluminum with respect to a total molar amount of nickel, cobalt, and manganese.

(2-1-3) Production of Positive Electrode (I-P3)

A positive electrode (I-P3) was produced in the same manner as in (2-1-1), except that titanium oxide ($TiO_2$) was used as the coating agent, and the mixing amount of titanium oxide was adjusted to be 0.12% by mole in terms of titanium with respect to a total molar amount of nickel, cobalt, and manganese.

(2-1-4) Production of Positive Electrode (I-P4)

A positive electrode (I-P4) was produced in the same manner as in (2-1-1), except that the positive electrode active material was not coated, and a composite oxide ($LiNi_{0.8}Mn_{0.1}Co_{0.1}O_2$) of lithium, nickel, manganese, and cobalt was used as the positive electrode active material.

(2-1-5) Production of Positive Electrode (I-P5)

A positive electrode (I-P5) was produced in the same manner as in (2-1-1), except that the positive electrode active material was not coated, and a composite oxide ($LiNi_{0.8}Mn_{0.1}Co_{0.1}Zr_{0.005}O_2$) of lithium, nickel, manganese, cobalt, and zirconium was used as the positive electrode active material.

(2-1-6) Production of Positive Electrode (I-P6)

A composite oxide ($LiNi_{0.6}Mn_{0.2}Co_{0.2}O_2$) of lithium, nickel, manganese, and cobalt as core particles of a positive electrode active material and aluminum oxide ($Al_2O_3$) as a coating agent are mixed using a Henschel mixer. The mixing amount of aluminum oxide is adjusted to be 3.6% by mole in terms of aluminum with respect to a total molar amount of nickel, cobalt, and manganese. The thus obtained mixture is calcined at 580° C. for 10 hours in the atmosphere.

The mixture obtained in the above-described manner, an acetylene black powder, and polyvinylidene fluoride (PVDF) were mixed as (A) a positive electrode active material, (B) a conductive aid, and a binder, respectively, at a weight ratio of 94:3:3 to obtain a positive electrode mixture.

To the thus obtained positive electrode mixture, N-methyl-2-pyrrolidone was added as a solvent such that a solid content of 68% by weight was obtained, and the resultant was further mixed to prepare a positive electrode mixture-containing slurry. One side of an aluminum foil having a thickness of 15 μm and a width of 280 mm, which served as a positive electrode current collector, was coated with the positive electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 130° C. for 8 hours. Thereafter, the electrode roll was rolled using a roll press such that the resulting positive electrode active material layer had a density of 2.9 g/cm$^3$, whereby a positive electrode (I-P6) composed of the positive electrode active material layer and the positive electrode current collector was obtained. The basis weight excluding the positive electrode current collector was 19.7 mg/cm$^2$.

(2-1-7) Production of Positive Electrode (I-P7)

A positive electrode (I-P7) was produced in the same manner as in (2-1-6), except that zirconium oxide (ZrO$_2$) was used as the coating agent, and the mixing amount of zirconium oxide was adjusted to be 0.05% by mole in terms of zirconium with respect to a total molar amount of nickel, cobalt, and manganese.

(2-1-8) Production of Positive Electrode (I-P8)

A positive electrode (I-P8) was produced in the same manner as in (2-1-6), except that the positive electrode active material was not coated, and a composite oxide (LiNi$_{0.6}$Mn$_{0.2}$Co$_{0.2}$O$_2$) of lithium, nickel, manganese, and cobalt was used as the positive electrode active material.

(2-1-9) Production of Positive Electrode (I-P9)

A composite oxide (LiNi$_{0.8}$Mn$_{0.1}$Co$_{0.1}$O$_2$) of lithium, nickel, manganese, and cobalt as core particles of a positive electrode active material and zirconium oxide (ZrO$_2$) as a coating agent are mixed using a Henschel mixer. The mixing amount of zirconium oxide is adjusted to be 0.05% by mole in terms of zirconium with respect to a total molar amount of nickel, cobalt, and manganese. The thus obtained mixture is calcined at 580° C. for 10 hours in the atmosphere.

A positive electrode active material composite obtained in the above-described manner, an acetylene black powder, and polyvinylidene fluoride (PVDF) were mixed as (A) a positive electrode active material, (B) a conductive aid, and a binder, respectively, at a weight ratio of 94:3:3 to obtain a positive electrode mixture.

To the thus obtained positive electrode mixture, N-methyl-2-pyrrolidone was added as a solvent such that a solid content of 68% by weight was obtained, and the resultant was further mixed to prepare a positive electrode mixture-containing slurry. One side of an aluminum foil having a thickness of 15 μm and a width of 280 mm, which served as a positive electrode current collector, was coated with the positive electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 130° C. for 8 hours. Thereafter, the electrode roll was rolled using a roll press such that the resulting positive electrode active material layer had a density of 2.7 g/cm$^3$, whereby a positive electrode (I-P9) composed of the positive electrode active material layer and the positive electrode current collector was obtained. The basis weight excluding the positive electrode current collector was 8.4 mg/cm$^2$.

(2-1-10) Production of Positive Electrode (I-P10)

A composite oxide (LiNi$_{0.6}$Mn$_{0.2}$Co$_{0.2}$O$_2$) of lithium, nickel, manganese, and cobalt as core particles of a positive electrode active material and aluminum oxide (Al$_2$O$_3$) as a coating agent are mixed using a Henschel mixer. The mixing amount of aluminum oxide is adjusted to be 3.6% by mole in terms of aluminum with respect to a total molar amount of nickel, cobalt, and manganese. The thus obtained mixture is calcined at 580° C. for 10 hours in the atmosphere.

The mixture obtained in the above-described manner, an acetylene black powder, and polyvinylidene fluoride (PVDF) were mixed as (A) a positive electrode active material, (B) a conductive aid, and a binder, respectively, at a weight ratio of 94:3:3 to obtain a positive electrode mixture.

To the thus obtained positive electrode mixture, N-methyl-2-pyrrolidone was added as a solvent such that a solid content of 68% by weight was obtained, and the resultant was further mixed to prepare a positive electrode mixture-containing slurry. One side of an aluminum foil having a thickness of 15 μm and a width of 280 mm, which served as a positive electrode current collector, was coated with the positive electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 130° C. for 8 hours. Thereafter, the electrode roll was rolled using a roll press such that the resulting positive electrode active material layer had a density of 2.7 g/cm$^3$, whereby a positive electrode (I-P10) composed of the positive electrode active material layer and the positive electrode current collector was obtained. The basis weight excluding the positive electrode current collector was 10.0 mg/cm$^2$.

(2-2) Production of Negative Electrodes (2-2-1) Production of Negative Electrode (I-N1)

A graphite powder, an acetylene black powder, and polyvinylidene fluoride (PVDF) were mixed as (a) a negative electrode active material, (b) a conductive aid, and a binder, respectively, at a weight ratio of 90.0:3.0:7.0 to obtain a negative electrode mixture.

To the thus obtained negative electrode mixture, water was added as a solvent such that a solid content of 45% by weight was obtained, and the resultant was further mixed to prepare a negative electrode mixture-containing slurry. One side of a copper foil having a thickness of 8 μm and a width of 280 mm, which served as a negative electrode current collector, was coated with the negative electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 80° C. for 12 hours. Thereafter, the electrode roll was rolled using a roll press such that the negative electrode active material layer had a density of 1.4 g/cm$^3$, whereby a negative electrode (I-N1) composed of the negative electrode active material layer and the negative electrode current collector was obtained. The basis weight excluding the negative electrode current collector was 10.3 mg/cm$^2$.

(2-2-2) Production of Negative Electrode (I-N2)

A graphite powder, an acetylene black powder, and polyvinylidene fluoride (PVDF) were mixed as (a) a negative electrode active material, (b) a conductive aid, and a binder, respectively, at a weight ratio of 90.0:3.0:7.0 to obtain a negative electrode mixture.

To the thus obtained negative electrode mixture, water was added as a solvent such that a solid content of 45% by weight was obtained, and the resultant was further mixed to prepare a negative electrode mixture-containing slurry. One side of a copper foil having a thickness of 8 μm and a width of 280 mm, which served as a negative electrode current collector, was coated with the negative electrode mixture-containing slurry using a three-roll transfer coater while adjusting the basis weight of the slurry such that a coating pattern having a coated width of 240 to 250 mm, a coated length of 125 mm, and an uncoated length of 20 mm was obtained, and the solvent was subsequently removed by drying in a hot-air drying furnace. Both sides of the resulting electrode roll were trimmed by cutting, and this electrode roll was dried under reduced pressure at 80° C. for 12 hours. Thereafter, the electrode roll was rolled using a roll press such that the negative electrode active material layer had a density of 1.3 g/cm$^3$, whereby a negative electrode (I-N2) composed of the negative electrode active material layer and the negative electrode current collector was obtained. The basis weight excluding the negative electrode current collector was 5.4 mg/cm$^2$.

(2-3) Assembly of Coin-Type and Small-Sized Non-Aqueous Secondary Batteries (2-3-1) Assembly of Coin-Type Non-Aqueous Secondary Batteries A polypropylene gasket was set in a CR2032-type battery casing (SUS304/Al-clad), and the positive electrode obtained in the above-described manner was punched into a disk shape having a diameter of 15.958 mm and set in the center of the gasket with the positive electrode active material layer facing upward. A glass fiber filter paper (GA-100, manufactured by Advantec Co., Ltd.) punched into a disk shape having a diameter of 16.156 mm was set thereon, and 150 μL of a non-aqueous electrolyte solution was injected, after which the negative electrode obtained in the above-described manner was punched into a disk shape having a diameter of 16.156 mm and set with the negative electrode active material layer facing downward. Further, a spacer and a spring were set, and a battery cap was subsequently fitted and crimped using a caulking machine. The electrolyte solution overflowed from the thus obtained assembly was wiped off with a waste cloth. This assembly was maintained at a temperature of 25° C. for 12 hours to allow the non-aqueous electrolyte solution (one selected from the above Table 1) to thoroughly impregnate into the layered product, whereby a coin-type non-aqueous secondary battery was obtained.

(2-3-2) Assembly of Small-Sized Non-Aqueous Secondary Batteries

The positive electrode obtained in the above-described manner that had been punched into a disk shape of 15.958 mm in diameter and the negative electrode obtained in the above-described manner that had been punched into a disk shape of 16.156 mm in diameter were superimposed on the respective sides of a polyethylene microporous membrane separator (membrane thickness: 21 μm, air permeability: 285 s/100 cm$^3$, porosity: 41%) to obtain a layered product. This layered product was inserted into an SUS-made disk-shaped battery casing. Subsequently, 200 μL of a non-aqueous electrolyte solution (one selected from the above Table 1) was injected into the battery casing to immerse the layered product in the non-aqueous electrolyte solution, after which the battery casing was tightly sealed and maintained at 25° C. for 12 hours to allow the non-aqueous electrolyte solution to thoroughly impregnate into the layered product, whereby a small-sized non-aqueous secondary battery was obtained.

(3) Evaluation of Coin-Type and Small-Sized Non-Aqueous Secondary Batteries (3-1) Evaluation of Coin-Type Non-Aqueous Secondary Batteries For the coin-type non-aqueous secondary batteries obtained in the above-described manner, first, an initial charging treatment was carried out and the initial charge-discharge capacity was measured in accordance with the procedures described below in (3-1-1). Next, each coin-type non-aqueous secondary battery was evaluated in accordance with the procedures of (3-1-2). Charging and discharging were carried out using a charge-discharge device ACD-M01A (trade name) manufactured by Aska Electronic Co., Ltd. and a programmable incubator IN804 (trade name) manufactured by Yamato Scientific Co., Ltd.

It is noted here that "1 C" means a current value at which discharging of a battery in a fully-charged state is expected to be completed in one hour when the discharging is carried out at a constant current.

In Examples according to the first embodiment, the current value corresponding to 1 C for each coin-type non-aqueous secondary battery is 6 mA.

(3-1-1) Initial Charge-Discharge Treatment (Step 1)

The ambient temperature of each coin-type non-aqueous secondary battery was set at 25° C., and the battery was charged to 3.1 V with a constant current of 0.15 mA corresponding to 0.025 C and subsequently further charged to 4.2 V with a constant current of 0.3 mA corresponding to 0.05 C, after which the battery was charged with a constant voltage of 4.2 V until the current value was reduced to 0.025 C. Thereafter, the battery was discharged to 3.0 V at a constant current of 0.9 mA corresponding to 0.15 C.

Next, the battery was charged to 4.2 V with a constant current of 1.2 mA corresponding to 0.2 C, and then further charged with a constant voltage of 4.2 V until the current value was reduced to 0.025 C. Subsequently, the battery was discharged to 3 V at a current value of 1.2 mA corresponding to 0.2 C. Thereafter, one cycle of the same charging and discharging operations as described above was carried out.

(3-1-2) 50° C. Cycle Test (Step 2)

For each coin-type non-aqueous secondary battery on which an initial charge-discharge treatment had been carried out by the method described above in (3-1-1), the ambient temperature was set at 50° C. and, after the battery was charged to 4.2 V with a constant current of 9 mA corresponding to 1.5 C, the battery was further charged with a constant voltage of 4.2 V until the current value was reduced to 0.025 C. Subsequently, the battery was discharged to 3 V at a current value of 9 mA corresponding to 1.5 C. Thereafter, 100 cycles of the same charging and discharging operations as described above were carried out.

The discharge capacity in the 100th cycle of this cycle test was calculated as 50° C. cycle capacity retention rate, taking the discharge capacity in the 2nd cycle of the initial charge-discharge treatment as 100%.

(3-1-3) 5 C Output Test

For each coin-type non-aqueous secondary battery on which an initial charge-discharge treatment had been carried out by the method described above in (3-1-1), the ambient temperature was set at 25° C. and, after the battery was charged to 4.2 V with a constant current of 3.0 mA corresponding to 0.5 C, the battery was further charged with a constant voltage of 4.2 V until the current value was reduced to 0.025 C. Thereafter, the battery was discharged to 3.0 V at a current value of 1.2 mA corresponding to 0.2 C.

Next, the battery was charged to 4.2 V with a constant current of 3 mA corresponding to 0.5 C, and then further charged with a constant voltage of 4.2 V until the current value was reduced to 0.025 C. Subsequently, the battery was discharged to 3.0 V at a current value of 30 mA corresponding to 5 C. The discharge capacity at 5 C was calculated as 5 C capacity retention rate, taking the discharge capacity in the 2nd cycle of the initial charge-discharge treatment as 100%.

The 5 C capacity retention rate serves as an index of the output performance at normal temperature, and it is preferably 30% or higher, more preferably 35% or higher.

(3-2) Evaluation of Small-Sized Non-Aqueous Secondary Batteries

Small-sized non-aqueous secondary batteries were evaluated by the same method as in (3-1).

In Examples according to the first embodiment, the current value corresponding to 1 C for each small-sized non-aqueous secondary battery is 3 mA.

(3-2-1) Initial Charge-Discharge Treatment (Step 1)

The ambient temperature of each small-sized non-aqueous secondary battery was set at 25° C., and the battery was charged to 4.2 V with a constant current of 0.3 mA corresponding to 0.1 C and then further charged with a constant voltage of 4.2 V until the current value was reduced to 0.025 C. Subsequently, the battery was discharged to 3.0 V at a constant current of 0.3 mA corresponding to 0.1 C. Thereafter, two cycles of the same charging and discharging operations as described above were carried out.

(3-2-2) 50° C. Cycle Test (Step 2)

For each small-sized non-aqueous secondary battery on which an initial charge-discharge treatment had been carried out by the method described above in (3-2-1), the ambient temperature was set at 50° C. and, after the battery was charged to 4.2 V with a constant current of 3 mA corresponding to 1 C, the battery was further charged with a constant voltage of 4.2 V until the current value was reduced to 0.025 C. Subsequently, the battery was discharged to 3 V at a current value of 3 mA corresponding to 1 C. Thereafter, 100 cycles of the same charging and discharging operations as described above were carried out.

The discharge capacity in the 100th cycle of this 50° C. cycle test was calculated as 50° C. cycle capacity retention rate, taking the discharge capacity in the 2nd cycle of the initial charge-discharge treatment as 100%.

(3-2-3) Output Tests at 10 C and 20 C

For each small-sized non-aqueous secondary battery on which an initial charge-discharge treatment had been carried out by the method described above in (3-2-1), the ambient temperature was set at 25° C. and, after the battery was charged to 4.2 V with a constant current of 3.0 mA corresponding to 1 C, the battery was further charged with a constant voltage of 4.2 V until the current value was reduced to 0.025 C. Thereafter, the battery was discharged to 3.0 V at a current value of 0.3 mA corresponding to 0.1 C. The discharge capacity in this process is defined as 0.1 C discharge capacity (H).

Next, the battery was charged to 4.2 V with a constant current of 3 mA corresponding to 1 C, and then further charged with a constant voltage of 4.2 V until the current value was reduced to 0.025 C. Subsequently, the battery was discharged to 3.0 V at a current value of 30 mA corresponding to 10 C. The discharge capacity at 10 C was calculated as 10 C capacity retention rate, taking the 0.1 C discharge capacity (H) as 100%.

The 10 C capacity retention rate serves as an index of the output performance at normal temperature, and it is preferably 45% or higher, more preferably 50% or higher.

Next, the battery was charged to 4.2 V with a constant current of 3 mA corresponding to 1 C, and then further charged with a constant voltage of 4.2 V until the current value was reduced to 0.025 C. Subsequently, the battery was discharged to 3.0 V at a current value of 60 mA corresponding to 20 C. The discharge capacity at 20 C was calculated as 20 C capacity retention rate, taking the 0.1 C discharge capacity (H) as 100%.

The 20 C capacity retention rate serves as an index of the output performance at normal temperature, and it is preferably 7.5% or higher, more preferably 10% or higher.

(4) Powder X-Ray Diffraction of Positive Electrodes

After the completion of the 50° C. cycle test corresponding to the step 2 and subsequent discharging at a constant current corresponding to 0.1 C until the battery voltage dropped to 2.5 V under a 25° C. environment, each coin-type or small-sized non-aqueous secondary battery was disassembled in an argon atmosphere to take out the positive electrode, which was subsequently washed with diethyl carbonate, dried, and then measured using a powder X-ray diffractometer. In addition, the (unenergized) positive electrode prior to the assembly of each coin-type or small-sized non-aqueous secondary battery was also measured using a powder X-ray diffractometer.

As the diffractometer, ULTIMA-IV manufactured by Rigaku Corporation was employed. The measurement conditions were set as follows: X-ray source=Cu-K$\alpha$, excitation voltage=40 kV; current=40 mA; optical system=centralized optical system; Cu-K$\beta$ radiation filter=Ni foil; detector=Dtex (high-sensitivity detector); measurement method=$\theta/2\theta$ method; slit: DS=1°, SS=open, RS=open; vertical slit=10 mm; and 2$\theta$ in 2$\theta/\theta$ scan=5 to 90° (0.02°/step, 0.5°/min).

The lattice constant was calculated using a software (PDXL) manufactured by Rigaku Corporation. The lattice constant was refined by the least-squares method using all observed peaks. The lattice was a hexagonal crystal, and the space group was R-3m (a=b, $\alpha=\beta=90°$, $\gamma=120°$).

The c-axis lattice constant of the (unenergized) positive electrode prior to the assembly of each coin-type or small-sized non-aqueous secondary battery is defined as c1, and the c-axis lattice constant of the positive electrode after the 50° C. cycle test is defined as c2.

The rate of change in the c-axis lattice constant was calculated based on the following equation:

$$\{(c2/c1)-1\} \times 100.$$

It is noted here that when an assembled non-aqueous secondary battery is measured, the non-aqueous secondary battery is discharged at a constant current until the battery voltage drops to 2.5 V or less under a 25° C. environment, and subsequently disassembled in an argon atmosphere to take out the positive electrode, which is subsequently washed with diethyl carbonate, dried, and then measured using a powder X-ray diffractometer. The c-axis lattice constant of this positive electrode is defined as c1.

(5) Cross-Sectional SEM Observation of Positive Electrodes

After the completion of the cycle test, the coin-type non-aqueous secondary batteries (Example I-1 and Comparative Example I-1) were each disassembled in an argon atmosphere to take out the positive electrode, which was subsequently washed with diethyl carbonate and dried, and a cross-section thereof was observed under an SEM.

A sample was cut out in an appropriate size in an argon atmosphere and immobilized on a BIB (Broad Ion Beam) processing sample holder. Subsequently, the sample was introduced to an apparatus in an isolated atmosphere using a special transfer vessel, and a cross-section was prepared by BIB processing. Thereafter, the sample was introduced to an SEM apparatus, again in an isolated atmosphere.

For the BIB processing, IB-09029CP manufactured by JEOL Ltd. was employed. The processing conditions were set as follows: ion species=$Ar^+$, preset temperature=$-150°$ C., and acceleration voltage=4.5 kV. For the SEM observation, SU8220 manufactured by Hitachi, Ltd. was employed. The measurement condition was set as follows: acceleration voltage=1 kV.

Figure 1:
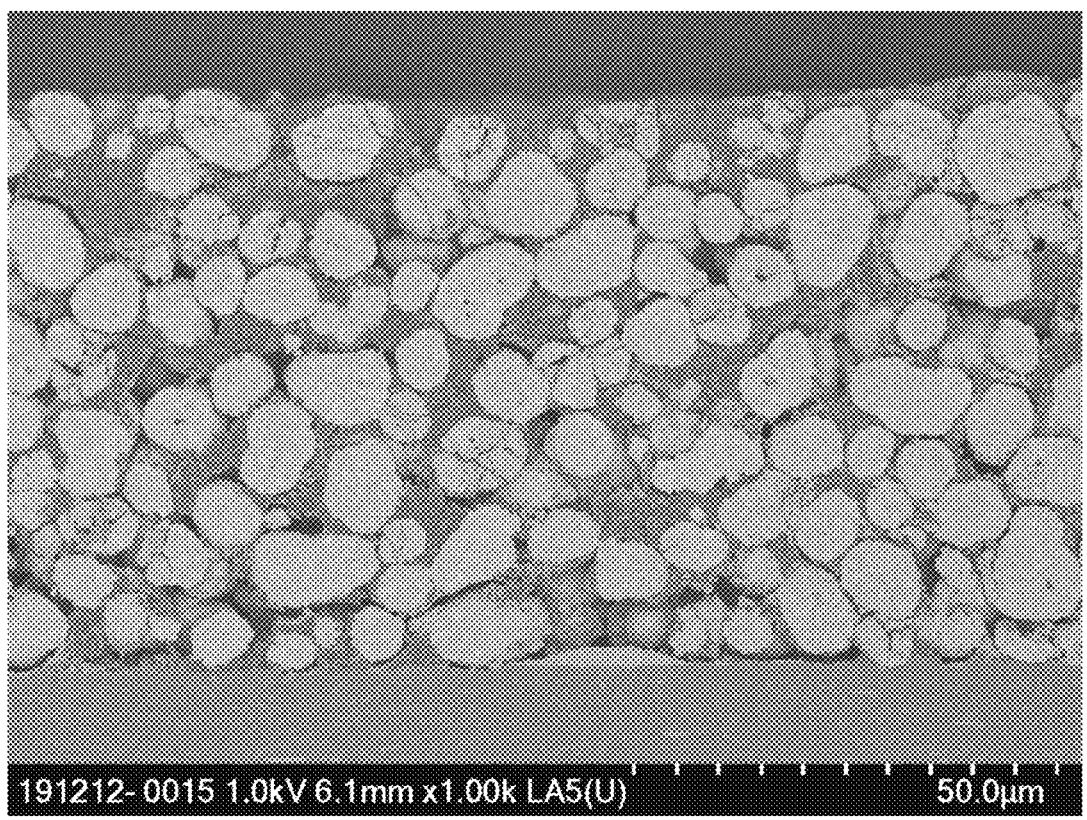
FIG. 1 is a cross-sectional SEM image of a positive electrode, which was taken after producing a non-aqueous secondary battery using the electrolyte solution of Example I-1 and carrying out 100 cycles of charging and discharging under a 50° C. environment after initial charging and discharging.
Figure 2:
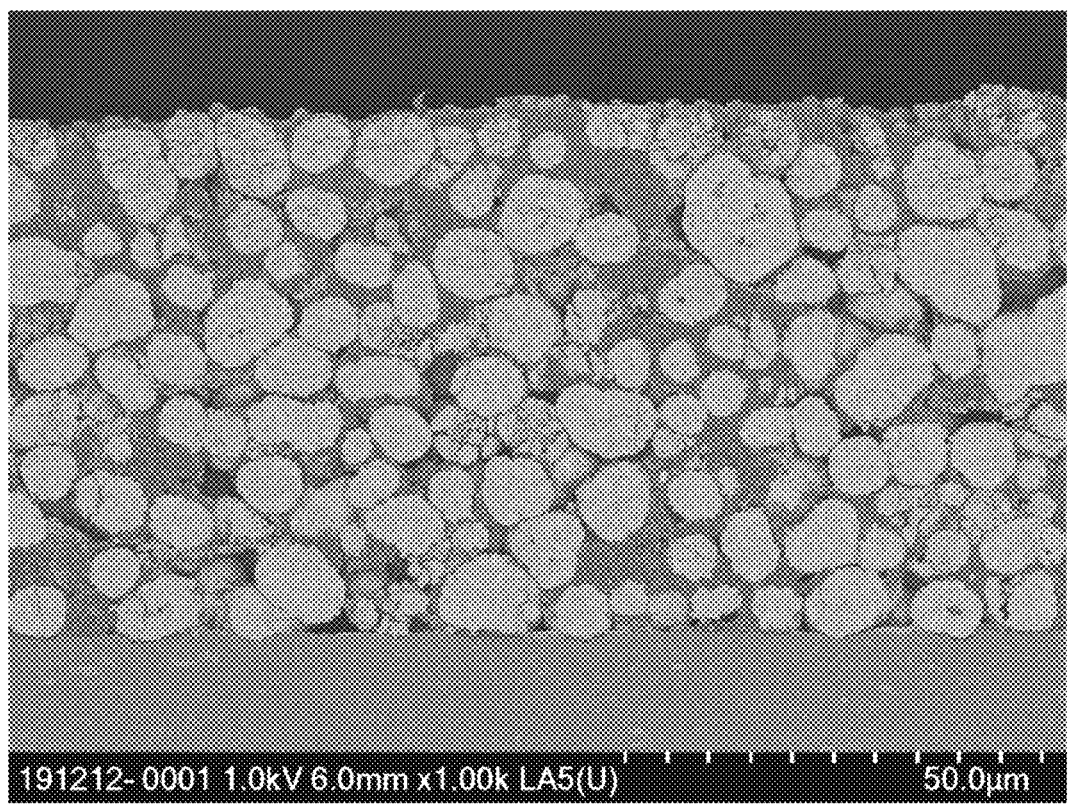
FIG. 2 is a cross-sectional SEM image of a positive electrode, which was taken after producing a non-aqueous secondary battery using the electrolyte solution of Comparative Example I-1 and carrying out 100 cycles of charging and discharging under a 50° C. environment after initial charging and discharging.

FIGS. 1 and 2 provide cross-sectional SEM images of the positive electrodes of the non-aqueous secondary batteries produced with the electrolyte solutions used in Examples I-1 and Comparative Example I-1, respectively, that were taken after a cycle test.

Examples I-1 to I-32 and Comparative Examples I-1 to I-11

Coin-type and small-sized non-aqueous secondary batteries were produced in accordance with the method described above in (2) using the respective positive electrodes and negative electrodes along with the non-aqueous electrolyte solutions shown in Table 1. Subsequently, the coin-type and small-sized non-aqueous secondary batteries were each evaluated in accordance with the procedures described above in (3) to (5). The test results are shown in Tables 2 to 4.

TABLE 2

| | Cell type | Positive electrode | Negative electrode | Non-aqueous electrolyte solution | Initial efficiency (%) | Initial discharge capacity (mAh) | 50° C. cycle capacity retention rate (%) | 5 C capacity retention rate (%) |
|---|---|---|---|---|---|---|---|---|
| Example I-1 | coin | I-P1 | I-N1 | S1 | 87.4 | 6.12 | 84.5 | 56.5 |
| Comparative Example I-1 | coin | I-P1 | I-N1 | S2 | 87.5 | 6.12 | 65.7 | 62.7 |
| Example I-2 | coin | I-P2 | I-N1 | S1 | 87.7 | 6.12 | 78.5 | 54.6 |
| Example I-3 | coin | I-P3 | I-N1 | S1 | 87.3 | 6.11 | 75.5 | 54.9 |
| Comparative Example I-2 | coin | I-P4 | I-N1 | S1 | 87.6 | 6.13 | 52.5 | 52.5 |
| Comparative Example I-3 | coin | I-P4 | I-N1 | S2 | 87.7 | 6.13 | 20.0 | 61.7 |
| Example I-4 | coin | I-P5 | I-N1 | S1 | 87.6 | 6.12 | 82.1 | 56.0 |
| Comparative Example I-4 | coin | I-P1 | I-N1 | S3 | 87.6 | 6.04 | 94.4 | 25.3 |
| Example I-5 | coin | I-P1 | I-N1 | S4 | 85.9 | 6.04 | 91.5 | 45.1 |
| Example I-6 | coin | I-P1 | I-N1 | S5 | 85.7 | 6.03 | 91.6 | 41.2 |
| Example I-7 | coin | I-P1 | I-N1 | S6 | 88.0 | 6.06 | 91.8 | 39.4 |
| Example I-8 | coin | I-P1 | I-N1 | S7 | 86.9 | 6.09 | 88.0 | 43.2 |
| Example I-9 | coin | I-P1 | I-N1 | S8 | 87.4 | 6.08 | 87.0 | 47.7 |
| Example I-10 | coin | I-P1 | I-N1 | S9 | 86.9 | 6.07 | 90.0 | 51.7 |
| Example I-11 | coin | I-P1 | I-N1 | S10 | 87.7 | 6.11 | 88.1 | 45.1 |
| Example I-12 | coin | I-P1 | I-N1 | S11 | 87.0 | 6.03 | 81.0 | 55.7 |
| Example I-13 | coin | I-P1 | I-N1 | S12 | 89.3 | 6.11 | 88.1 | 43.5 |
| Example I-14 | coin | I-P1 | I-N1 | S13 | 89.1 | 6.10 | 83.2 | 42.2 |
| Example I-15 | coin | I-P1 | I-N1 | S14 | 87.6 | 5.98 | 84.8 | 40.4 |
| Comparative Example I-5 | coin | I-P1 | I-N1 | S15 | 87.8 | 6.13 | 51.8 | 65.5 |
| Comparative Example I-6 | coin | I-P1 | I-N1 | S16 | 87.6 | 6.11 | 57.2 | 66.3 |
| Comparative Example I-7 | coin | I-P1 | I-N1 | S17 | 86.1 | 6.06 | 49.8 | 62.5 |
| Comparative Example I-8 | coin | I-P1 | I-N1 | S18 | 85.9 | 6.15 | 21.2 | 60.8 |
| Example I-16 | coin | I-P1 | I-N1 | S19 | 85.1 | 5.95 | 91.5 | 41.1 |
| Example I-17 | coin | I-P1 | I-N1 | S20 | 87.4 | 5.98 | 87.0 | 43.5 |
| Example I-18 | coin | I-P1 | I-N1 | S21 | 87.1 | 5.96 | 88.1 | 42.2 |
| Example I-19 | coin | I-P1 | I-N1 | S22 | 86.9 | 6.08 | 81.7 | 51.1 |
| Example I-20 | coin | I-P1 | I-N1 | S23 | 87.1 | 6.04 | 82.1 | 53.5 |
| Example I-21 | coin | I-P1 | I-N1 | S24 | 87.2 | 6.05 | 84.1 | 51.7 |
| Example I-22 | coin | I-P1 | I-N1 | S25 | 87.2 | 7.70 | 82.5 | 46.5 |
| Example I-23 | coin | I-P1 | I-N1 | S26 | 87.1 | 7.72 | 83.6 | 45.5 |
| Example I-24 | coin | I-P6 | I-N1 | S22 | 83.9 | 3.03 | 87.2 | 53.2 |
| Example I-25 | coin | I-P6 | I-N1 | S27 | 84.5 | 3.02 | 88.4 | 51.0 |
| Example I-26 | coin | I-P6 | I-N1 | S28 | 84.1 | 3.04 | 90.8 | 40.5 |
| Example I-27 | coin | I-P7 | I-N1 | S22 | 83.5 | 3.05 | 88.5 | 50.9 |
| Example I-28 | coin | I-P7 | I-N1 | S28 | 84.3 | 3.01 | 91.5 | 41.2 |
| Comparative Example I-9 | coin | I-P8 | I-N1 | S29 | 84.5 | 3.06 | 62.8 | 66.1 |

TABLE 3

| | Cell type | Positive electrode | Negative electrode | Non-aqueous electrolyte solution | Initial efficiency (%) | Initial discharge capacity (mAh) | 50° C. cycle capacity retention rate (%) | 10 C capacity retention rate (%) | 20 C capacity retention rate (%) |
|---|---|---|---|---|---|---|---|---|---|
| Example I-29 | small-sized | I-P9 | I-N2 | S30 | 87.2 | 3.06 | 85.9 | 69.9 | 11.0 |
| Example I-30 | small-sized | I-P9 | I-N2 | S31 | 84.4 | 3.11 | 89.5 | 67.2 | 13.4 |
| Example I-31 | small-sized | I-P10 | I-N2 | S30 | 82.5 | 2.96 | 85.7 | 77.8 | 29.5 |
| Example I-32 | small-sized | I-P10 | I-N2 | S31 | 83.7 | 3.04 | 90.9 | 68.3 | 16.7 |
| Comparative Example I-10 | small-sized | I-P9 | I-N2 | S3 | 85.1 | 3.02 | 89.1 | 40.6 | 5.0 |
| Comparative Example I-11 | small-sized | I-P10 | I-N2 | S3 | 84.4 | 3.02 | 89.4 | 37.3 | 6.0 |

TABLE 4

| | Positive electrode before step 1 Lattice constant c1 (angstrom) | Positive electrode after step 2 Lattice constant c2 (angstrom) | Rate of change in c-axis lattice constant (%) |
|---|---|---|---|
| Example I-1 | 14.190 | 14.270 | 0.564 |
| Comparative Example I-1 | 14.190 | 14.350 | 1.128 |
| Example I-2 | 14.190 | 14.280 | 0.634 |
| Example I-3 | 14.190 | 14.278 | 0.620 |
| Comparative Example I-2 | 14.190 | 14.345 | 1.092 |
| Comparative Example I-3 | 14.190 | 14.380 | 1.339 |
| Example I-4 | 14.190 | 14.275 | 0.599 |
| Comparative Example I-4 | 14.190 | 14.260 | 0.493 |
| Example I-5 | 14.190 | 14.220 | 0.211 |
| Example I-6 | 14.190 | 14.243 | 0.374 |
| Example I-7 | 14.190 | 14.240 | 0.352 |
| Example I-8 | 14.190 | 14.250 | 0.423 |
| Example I-9 | 14.190 | 14.263 | 0.514 |
| Example I-10 | 14.190 | 14.240 | 0.352 |
| Example I-11 | 14.190 | 14.245 | 0.388 |
| Example I-12 | 14.190 | 14.270 | 0.564 |
| Example I-13 | 14.190 | 14.258 | 0.479 |
| Example I-14 | 14.190 | 14.250 | 0.423 |
| Example I-15 | 14.190 | 14.246 | 0.395 |
| Comparative Example I-5 | 14.190 | 14.340 | 1.057 |
| Comparative Example I-6 | 14.190 | 14.350 | 1.128 |
| Comparative Example I-7 | 14.190 | 14.350 | 1.128 |
| Comparative Example I-8 | 14.190 | 14.410 | 1.550 |
| Example I-16 | 14.190 | 14.200 | 0.070 |
| Example I-17 | 14.190 | 14.220 | 0.211 |
| Example I-18 | 14.190 | 14.214 | 0.169 |
| Example I-19 | 14.190 | 14.263 | 0.514 |
| Example I-20 | 14.190 | 14.250 | 0.423 |
| Example I-21 | 14.190 | 14.219 | 0.204 |
| Example I-22 | 14.190 | 14.270 | 0.564 |
| Example I-23 | 14.190 | 14.260 | 0.493 |
| Example I-24 | 14.218 | 14.285 | 0.471 |
| Example I-25 | 14.218 | 14.282 | 0.450 |
| Example I-26 | 14.218 | 14.250 | 0.225 |
| Example I-27 | 14.218 | 14.268 | 0.352 |
| Example I-28 | 14.218 | 14.245 | 0.190 |
| Comparative Example I-9 | 14.218 | 14.365 | 1.034 |
| Example I-29 | 14.190 | 14.252 | 0.437 |
| Example I-30 | 14.190 | 14.246 | 0.395 |
| Example I-31 | 14.218 | 14.271 | 0.373 |
| Example I-32 | 14.218 | 14.250 | 0.225 |
| Comparative Example I-10 | 14.190 | 14.245 | 0.388 |
| Comparative Example I-11 | 14.218 | 14.248 | 0.211 |

As shown in Tables 2 and 4, in Examples I-1 to I-28, the capacity retention rate in the cycle test was 70% or higher, the rate of change in the c-axis lattice constant of the positive electrode after the cycle test with respect to before the assembly of each coin-type non-aqueous secondary battery was 1.0% or lower, and the 5 C capacity retention rate was 30% or higher. On the other hand, in Comparative Examples I-1 to I-3 and I-5 to I-9, the capacity retention rate in the cycle test was 66% or lower, and the rate of change in the c-axis lattice constant was higher than 1.0%. In addition, in Comparative Example I-4, the 5 C capacity retention rate was lower than 30%.

Further, as shown in Tables 3 and 4, in Examples I-29 to I-32, the capacity retention rate in the cycle test was 70% or higher, the rate of change in the c-axis lattice constant of the positive electrode after the cycle test with respect to before the assembly of each small-sized non-aqueous secondary battery was 1.0% or lower, the 10 C capacity retention rate was 45% or higher, and the 20 C capacity retention rate was 7.5% or higher. On the other hand, in Comparative Examples I-10 and I-11, the 10 C capacity retention rate was lower than 45%, and the 20 C capacity retention rate was lower than 7.5%.

As indicated by these results, it was revealed that, by using an non-aqueous electrolyte solution and a specific positive electrode active material that are within the scope of the present invention and thereby reducing the rate of change in the c-axis lattice constant to be in a prescribed range, the cycle performance under a high temperature environment can be inhibited while allowing sufficient output performance to be exerted.

Comparing Examples I-1 and I-5 to I-23 with Comparative Examples I-1 and I-5 to I-8, the capacity retention rate in the cycle test was improved to 70% or higher by controlling the acetonitrile amount and the ionic conductivity in the respective non-aqueous electrolyte solutions to be in prescribed ranges and reducing the rate of change in the c-axis lattice constant to be 1.0% or lower. This is believed to be because not only cracking of the positive electrode active material during charge-discharge cycles under a high temperature environment was inhibited by reducing the rate of change in the c-axis lattice constant of the positive electrode to 1.0% or lower, but also the amount of lithium extraction from the positive electrode was made uniform and cracking of the positive electrode active material was inhibited by controlling the acetonitrile amount and the ionic conductivity to be in prescribed ranges, as a result of which various deterioration phenomena under a high temperature environment were inhibited.

Comparing Examples I-1 to I-3 with Comparative Example I-2, the capacity retention rate in the cycle test was improved to 70% or higher by using the positive electrode having a coating layer and reducing the rate of change in the c-axis lattice constant to 1.0% or lower. This is believed to be because, by allowing the positive electrode active material to have a coating layer, not only the diffusion rate of the acetonitrile-containing non-aqueous electrolyte solution into deep parts of positive electrode active material particles was reduced and lithium extraction in the deep parts of the positive electrode active material particles was thereby inhibited, but also the crystal structure of the positive electrode active material was stabilized and spinel transition occurring with the progress of deterioration caused by non-uniform lithium extraction was inhibited, whereby the rate of change in the c-axis lattice constant of the positive electrode was reduced and cracking of the positive electrode active material was inhibited, as a result of which various deterioration phenomena under a high temperature environment were inhibited.

Comparing Example I-4 with Comparative Example I-2, the capacity retention rate in the cycle test was improved to 80% or higher by using the positive electrode containing a doping element and reducing the rate of change in the c-axis lattice constant to 1.0% or lower. This is believed to be because, by incorporating the doping element into the positive electrode active material, the crystal structure of the positive electrode active material was stabilized and spinel transition caused by non-uniform lithium extraction was inhibited, whereby the rate of change in the c-axis lattice constant of the positive electrode was reduced and cracking of the positive electrode active material was inhibited, as a result of which various deterioration phenomena under a high temperature environment were inhibited.

Comparing Examples I-1 and I-5 to I-23 with Comparative Example I-4, the 5 C capacity retention rate was improved to 30% or higher by controlling the acetonitrile amount and the ionic conductivity in the non-aqueous electrolyte solution to be in prescribed ranges. This is believed to be because, by controlling the acetonitrile amount and the ionic conductivity to be in prescribed ranges, the rate of insertion/release of lithium ions to/from the electrode was improved, as a result of which high output characteristics was exerted.

Comparing Examples I-24 to I-28 with Comparative Example I-9, the capacity retention rate in the cycle test was improved to 70% or higher by using the positive electrode having a coating layer, controlling the acetonitrile amount and the ionic conductivity in the non-aqueous electrolyte solution to be in prescribed ranges, and reducing the rate of change in the c-axis lattice constant to 1.0% or lower. This is believed to be because, by allowing the positive electrode active material to have a coating layer, not only the diffusion rate of the acetonitrile-containing non-aqueous electrolyte solution into deep parts of positive electrode active material particles was reduced and lithium extraction in the deep parts of the positive electrode active material particles was thereby inhibited, but also the crystal structure of the positive electrode active material was stabilized and spinel transition occurring with the progress of deterioration caused by non-uniform lithium extraction was inhibited, whereby the rate of change in the c-axis lattice constant of the positive electrode was reduced and cracking of the positive electrode active material was inhibited, as a result of which various deterioration phenomena under a high temperature environment were inhibited. It is also believed that, in addition to the above, not only cracking of the positive electrode active material during charge-discharge cycles under a high temperature environment was inhibited by reducing the rate of change in the c-axis lattice constant of the positive electrode to 1.0% or lower, but also the amount of lithium extraction from the positive electrode was made uniform and cracking of the positive electrode active material was inhibited by controlling the acetonitrile amount and the ionic conductivity to be in prescribed ranges, as a result of which various deterioration phenomena under a high temperature environment were inhibited.

Comparing Examples I-29 and I-30 with Comparative Example I-10 or Examples I-31 and I-32 with Comparative Example I-11, by controlling the acetonitrile amount and the ionic conductivity in the non-aqueous electrolyte solution to be in prescribed ranges, the 10 C capacity retention rate was improved to 45% or higher and the 20 C capacity retention rate was improved to 7.5% or higher. This is believed to be because, by controlling the acetonitrile content to be not less than 5% by volume per total amount of the non-aqueous solvent(s), the ionic conductivity was increased and the rate of insertion/release of lithium ions to/from the electrode was improved, as a result of which high output characteristics was exerted.

Comparing Examples I-1 and I-4 with Examples I-2 and I-3, the capacity retention rate in the cycle test was improved by incorporating zirconium as a doping element or using zirconium oxide as a coating agent, and reducing the rate of change in the c-axis lattice constant to 0.6% or lower. This is believed to be because by using zirconium as a coating element or a doping element, the crystal structure of the positive electrode active material is stabilized, and the rate of change in the c-axis lattice constant of the positive electrode was reduced so that cracking of the positive electrode active material can be inhibited, as a result of which various deterioration phenomena under a high temperature environment were inhibited.

Comparing Example I-1 with Example I-4, the capacity retention rate in the cycle test was improved in the case where zirconium oxide was used as a coating agent than in the case where zirconium was incorporated as a doping element. This is believed to be because, when a coating layer was incorporated as compared to when a doping element was incorporated, not only the diffusion rate of the acetonitrile-containing non-aqueous electrolyte solution into deep parts of positive electrode active material particles was reduced and lithium extraction in the deep parts of the positive electrode active material particles was thereby inhibited, but also the crystal structure of the positive electrode active material was stabilized and spinel transition occurring with the progress of deterioration caused by non-uniform lithium extraction was inhibited, whereby the rate of change in the c-axis lattice constant of the positive electrode was reduced and cracking of the positive electrode active material was inhibited, as a result of which various deterioration phenomena under a high temperature environment were inhibited.

Comparing Example I-7 with Example I-6, Example I-15 with Example I-14, Example I-18 with Example I-17, Example I-20 with Example I-19, Example I-23 with Example I-22, or Example I-25 with Example I-24, the rate of change in the c-axis lattice constant was reduced and the capacity retention rate in the cycle test was improved by adding a prescribed amount of a dinitrile compound to the respective non-aqueous electrolyte solutions as an additive. This is believed to be because, by adding a dinitrile compound to the respective non-aqueous electrolyte solutions as an additive, the crystal structure of the positive electrode active material was stabilized and the rate of change in the c-axis lattice constant of the positive electrode was thereby reduced, so that cracking of the positive electrode active material was inhibited, as a result of which various deterioration phenomena under a high temperature environment were inhibited.

Comparing Example I-21 with Example I-19, Example I-30 with Example I-29, or Example I-32 with I-31, the rate of change in the c-axis lattice constant was reduced and the capacity retention rate in the cycle test was improved by adding a prescribed amount of a nitrogen-containing cyclic compound to the respective non-aqueous electrolyte solutions as an additive. This is believed to be because, by adding a nitrogen-containing cyclic compound to the respective non-aqueous electrolyte solutions as an additive, the crystal structure of the positive electrode active material was stabilized through inhibition of phase transition of the positive electrode active material, and the rate of change in the c-axis lattice constant of the positive electrode was thereby reduced, so that cracking of the positive electrode active material was inhibited, as a result of which various deterioration phenomena under a high temperature environment were inhibited.

Second Embodiment (1) Preparation of Non-Aqueous Electrolyte Solutions

Non-aqueous electrolyte solutions (T01) to (T25) were prepared by mixing various non-aqueous solvents and additives each at a prescribed concentration in an inert atmosphere and further adding various lithium salts such that the resultants each have a prescribed concentration thereof. The compositions of these non-aqueous electrolyte solutions are shown in Table 5.

The abbreviations used for non-aqueous solvents, dinitrile compounds, and lithium salts in Table 5 have the below-described meanings.

In Table 5, "DN" represents a dinitrile compound.

The molar concentration of each lithium salt in Table 5 indicates a molar concentration per 1 L of the non-aqueous solvent(s), and the amount (% by weight) of each dinitrile compound in Table 5 indicates an amount (% by weight) with respect to a total amount of each non-aqueous electrolyte solution. A value in % by volume and a value in % by weight are interconvertible using the specific gravity values (25° C.) of the respective non-aqueous solvents, lithium salt, and dinitrile compound.

(Non-Aqueous Solvents)
AcN: acetonitrile
EMC: ethyl methyl carbonate
DEC: diethyl carbonate
GBL: γ-butyrolactone
PP: propyl propionate
EC: ethylene carbonate
ES: ethylene sulfite
VC: vinylene carbonate
SN: succinonitrile
MeSN: methylsuccinonitrile
(Lithium Salts)
$LiPF_6$: lithium hexafluorophosphate
LiFSI: lithium bis(fluorosulfonyl)imide ($LiN(SO_2F)_2$)
(Dinitrile Compounds)
SN: succinonitrile
MeSN: methylsuccinonitrile (2) Measurement of Ionic Conductivity of Non-Aqueous Electrolyte Solutions For the non-aqueous electrolyte solutions (T01) to (T11), (T18), (T19), (T21), (T23) and (T24) among those obtained in the above-described manner, the ionic conductivity was measured.

The ionic conductivity of each non-aqueous electrolyte solution was measured at 25° C. by inserting an ionic conductivity measurement cell "CT-58101B" (trade name) manufactured by DKK-TOA Corporation, which was connected to an ionic conductivity meter "CM-41X" (trade name) manufactured by DKK-TOA Corporation, into a polypropylene container in which the non-aqueous electrolyte solution was placed.

When a non-aqueous electrolyte solution having a low ionic conductivity is used in a non-aqueous secondary battery, since the moving rate of lithium ions is limited by the ionic conductivity of the non-aqueous electrolyte solution, the desired input-output characteristics cannot be obtained in some cases. Therefore, the ionic conductivity of the non-aqueous electrolyte solution is desirably 10 mS/cm or higher.

The thus obtained measurement results are shown in Table 6.

TABLE 6

| | Electrolyte solution No. | Ionic conductivity [mS/cm] |
|---|---|---|
| Example II-1 | T01 | 14.3 |
| Example II-2 | T02 | 14.6 |
| Example II-3 | T03 | 13.9 |

TABLE 5

| Electrolyte solution No. | Lithium salt [mol/L] | | Composition of non-aqueous solvent [% by volume] | | | | | | | | | | DN [% by weight] | DN/AN [molar ratio] | Ratio of non-aqueous solvents with respect to total amount of non-aqueous solvents and DN [% by volume] | Ratio of non-aqueous solvents with respect to total amount of non-aqueous solvents and DN [% by weight] |
|---|---|---|---|---|---|---|---|---|---|---|---|---|---|---|---|---|
| | LiPF6 | LiFSI | AcN | EMC | DEC | GBL | PP | EC | ES | VC | SN | MeSN | | | | |
| T01 | 0.33 | 1.10 | 22.1 | 38.1 | — | 13.8 | — | 23.2 | — | 2.8 | — | 7.1 | 0.26 | 90.5 | 91.2 |
| T02 | 0.32 | 1.08 | 21.6 | 37.3 | — | 15.7 | — | 22.7 | — | 2.7 | 5.9 | — | 0.25 | 92.5 | 92.8 |
| T03 | 0.35 | 1.18 | 23.5 | 40.6 | — | 8.2 | — | 24.7 | — | 2.9 | 11.6 | — | 0.50 | 85.0 | 85.4 |
| T04 | 0.38 | 1.28 | 12.8 | — | — | — | 57.1 | 26.9 | — | 3.2 | 17.5 | — | 1.47 | 78.0 | 77.7 |
| T05 | 0.44 | 1.47 | 14.7 | — | — | — | 50.7 | 30.9 | — | 3.7 | 26.0 | — | 2.34 | 68.0 | 68.0 |
| T06 | 0.46 | 1.54 | 15.4 | — | — | — | 48.5 | 32.3 | — | 3.8 | — | 27.4 | 1.90 | 65.0 | 66.3 |
| T07 | 0.33 | 1.11 | 38.3 | 22.2 | — | 13.3 | — | 23.3 | — | 2.8 | 8.1 | — | 0.17 | 90.0 | 90.0 |
| T08 | 0.34 | 1.15 | 69.0 | 4.0 | — | — | — | 24.1 | — | 2.9 | 11.2 | — | 0.12 | 87.0 | 86.0 |
| T09 | 0.38 | 1.28 | 6.4 | 63.5 | — | — | — | 26.9 | — | 3.2 | — | 16.4 | 2.38 | 78.0 | 80.0 |
| T10 | 0.38 | 1.28 | 6.4 | 63.5 | — | — | — | 26.9 | — | 3.2 | 17.2 | — | 2.51 | 78.0 | 79.1 |
| T11 | 0.98 | — | — | 69.0 | — | — | — | 29.0 | — | 2.0 | — | — | 0 | 100 | 100 |
| T12 | 0.33 | 1.11 | 44.4 | 27.8 | — | — | — | 23.3 | — | 4.4 | 8.3 | — | 0.14 | 90.0 | 89.8 |
| T13 | — | 1.11 | 44.4 | 27.8 | — | — | — | 23.3 | — | 4.4 | 8.6 | — | 0.14 | 90.0 | 89.8 |
| T14 | 1.44 | 0.33 | 44.4 | 27.8 | — | — | — | 23.3 | — | 4.4 | 8.6 | — | 0.14 | 90.0 | 89.8 |
| T15 | 0.30 | 1.00 | 20.0 | 34.5 | — | 22.0 | — | 21.0 | — | 2.5 | — | — | 0 | 100 | 100 |
| T16 | 0.32 | 1.07 | 52.4 | 22.5 | — | — | — | 22.5 | — | 2.7 | — | 5.2 | 0.07 | 93.5 | 93.5 |
| T17 | 0.32 | 1.07 | 52.4 | 22.5 | — | — | — | 22.5 | — | 2.7 | 5.5 | — | 0.08 | 93.5 | 93.2 |
| T18 | 0.30 | 1.00 | 10.0 | 73.7 | — | — | — | 10.0 | 3.8 | 2.5 | 1.6 | — | 0.12 | 98.4 | 98.4 |
| T19 | 0.30 | 1.00 | 25.0 | 58.7 | — | — | — | 10.0 | 3.8 | 2.5 | 3.2 | — | 0.10 | 96.9 | 96.8 |
| T20 | 0.30 | 1.00 | 25.0 | 58.7 | — | — | — | 10.0 | 3.8 | 2.5 | — | — | 0 | 100 | 100 |
| T21 | 0.30 | 1.00 | 10.0 | 73.7 | — | — | — | 10.0 | 3.8 | 2.5 | — | 1.9 | 0.12 | 98.1 | 98.1 |
| T22 | 0.30 | 1.00 | 10.0 | 73.7 | — | — | — | 10.0 | 3.8 | 2.5 | — | — | 0 | 100 | 100 |
| T23 | 0.30 | 1.00 | 35.0 | — | 39.0 | — | — | 20.0 | 4.0 | 2.0 | 6.0 | — | 0.12 | 94.3 | 94.2 |
| T24 | 0.30 | 1.00 | 35.0 | — | 39.0 | — | — | 20.0 | 4.0 | 2.0 | — | 7.0 | 0.12 | 93.5 | 93.5 |
| T25 | 0.30 | 1.00 | 35.0 | — | 39.0 | — | — | 20.0 | 4.0 | 2.0 | — | — | 0 | 100 | 100 |

TABLE 6-continued

| | Electrolyte solution No. | Ionic conductivity [mS/cm] |
|---|---|---|
| Example II-4 | T04 | 10.3 |
| Comparative Example II-1 | T05 | 9.4 |
| Comparative Example II-2 | T06 | 9.6 |
| Example II-5 | T07 | 17.5 |
| Example II-6 | T08 | 23.8 |
| Comparative Example II-3 | T09 | 9.1 |
| Comparative Example II-4 | T10 | 9.3 |
| Comparative Example II-5 | T11 | 9.0 |
| Example II-7 | T18 | 11.2 |
| Example II-8 | T19 | 14.9 |
| Example II-9 | T21 | 11.3 |
| Example II-10 | T23 | 18.2 |
| Example II-11 | T24 | 18.4 |

The ionic conductivity was lower than 10 mS/cm in Comparative Examples II-1 and II-2 where the content of a dinitrile compound was more than 25% by weight with respect to a total amount of each non-aqueous electrolyte solution or the content of non-aqueous solvents was 70% by volume or less and 70% by weight or less with respect to a total amount of the non-aqueous solvents and the dinitrile compound, as well as in Comparative Examples 11-3 to II-5 where the content of acetonitrile was less than 10% by volume with respect to a total amount of non-aqueous solvents; however, in Examples II-1 to II-11, the ionic conductivity was 10 mS/cm or higher. From these results, it was found desirable to control the content of acetonitrile, that of a dinitrile compound, and that of other non-aqueous solvent to be in prescribed ranges.

(3) Output Test (3-1) Production of Coin-Type Non-Aqueous Secondary Batteries (3-1-1) Production of Positive Electrode (II-P1) A composite oxide ($LiNi_{0.33}Mn_{0.33}Co_{0.33}O_2$) of lithium, nickel, manganese and cobalt as a positive electrode active material, a graphite powder and an acetylene black powder as conductive aids, and polyvinylidene fluoride (PVDF) as a binder were mixed at a weight ratio of 100:4.2:1.8:4.6 to obtain a positive electrode mixture.

To the thus obtained positive electrode mixture, N-methyl-2-pyrrolidone was added as a solvent such that a solid content of 68% by weight was obtained, and the resultant was further mixed to prepare a positive electrode mixture-containing slurry. One side of a 20 μm-thick aluminum foil serving as a positive electrode current collector was coated with the positive electrode mixture-containing slurry while adjusting the basis weight of the slurry to be 24.0 mg/cm$^2$, and the solvent was subsequently removed by drying. Thereafter, this aluminum foil was rolled using a roll press such that the resulting positive electrode active material layer had a density of 2.90 g/cm$^3$, whereby a positive electrode (II-P1) composed of the positive electrode active material layer and the positive electrode current collector was obtained.

(3-1-2) Production of Negative Electrode (II-N1)

A graphite powder having a number-average particle size of 12.7 μm and a graphite powder having a number-average particle size of 6.5 μm as negative electrode active materials were mixed with carboxymethyl cellulose and a diene-based rubber as binders at a weight ratio of 87.2:9.7:1.4:1.7 to obtain a negative electrode mixture.

To the thus obtained negative electrode mixture, water was added as a solvent such that a solid content of 45% by weight was obtained, and the resultant was further mixed to prepare a negative electrode mixture-containing slurry. One side of a 10 μm-thick copper foil serving as a negative electrode current collector was coated with the negative electrode mixture-containing slurry while adjusting the basis weight of the slurry to be 10.6 mg/cm$^2$, and the solvent was subsequently removed by drying. Thereafter, this copper foil was rolled using a roll press such that the resulting negative electrode active material layer had a density of 1.50 g/cm$^3$, whereby a negative electrode (II-N1) composed of the negative electrode active material layer and the negative electrode current collector was obtained.

(3-1-3) Assembly of Coin-Type Non-Aqueous Secondary Batteries

A polypropylene gasket was set in a CR2032-type battery casing (SUS304/Al-clad), and the positive electrode (II-P1) obtained in the above-described manner was punched into a disk shape having a diameter of 15.958 mm and set in the center of the gasket with the positive electrode active material layer facing upward. A glass fiber filter paper (GA-100, manufactured by Advantec Co., Ltd.) punched into a disk shape having a diameter of 16.156 mm was set thereon, and 150 μL of a non-aqueous electrolyte solution shown in Table 5 was injected, after which the negative electrode (II-N1) obtained in the above-described manner was punched into a disk shape having a diameter of 16.156 mm and set with the negative electrode active material layer facing downward. Further, a spacer and a spring were set in the battery casing, and a battery cap was subsequently fitted and crimped using a caulking machine. The overflowed non-aqueous electrolyte solution was wiped off with a waste cloth. The resulting assembly, which contained a layered product of the II-P1, the glass fiber filter paper and the II-N1 along with the non-aqueous electrolyte solution, was maintained at a temperature of 25° C. for 12 hours to allow the non-aqueous electrolyte solution to thoroughly impregnate into the layered product, whereby a coin-type non-aqueous secondary battery was obtained.

(3-2) Evaluation of Coin-Type Non-Aqueous Secondary Batteries

For the coin-type non-aqueous secondary batteries obtained in the above-described manner, first, an initial charging treatment was carried out in accordance with the procedures described below in (3-2-1). Next, each coin-type non-aqueous secondary battery was evaluated in accordance with the procedures of (3-2-2). Charging and discharging were carried out using a charge-discharge device ACD-M01A (trade name) manufactured by Aska Electronic Co., Ltd. and a programmable incubator IN804 (trade name) manufactured by Yamato Scientific Co., Ltd.

It is noted here that "1 C" means a current value at which discharging of a battery in a fully-charged state is expected to be completed in one hour when the discharging is carried out at a constant current. In the below-described evaluations of (3-2-1) and (3-2-2), "1 C" specifically means a current value at which discharging of a battery from a fully-charged state of 4.2 V to 3.0 V at a constant current is expected to be completed in one hour.

(3-2-1) Initial Charge-Discharge Treatment of Coin-Type Non-Aqueous Secondary Batteries The ambient temperature of each battery was set at 25° C., and the battery was charged to 4.2 V with a constant current of 0.6 mA corresponding to 0.1 C and then charged with a constant voltage of 4.2 V for a total of 1.5 hours. Subsequently, the battery was discharged to 3.0 V at a constant current of 1.8 mA corresponding to 0.3 C.

(3-2-2) Output Test of Coin-Type Non-Aqueous Secondary Batteries

For each battery on which an initial charge-discharge treatment had been carried out by the method described above in (3-2-1), the ambient temperature was set at 25° C., and the battery was charged to 4.2 V with a constant current of 6 mA corresponding to 1 C and then charged with a constant voltage of 4.2 V for a total of 3 hours. Subsequently, the battery was discharged to 3.0 V at a current value of 6 mA corresponding to 1 C. Thereafter, the battery was charged and discharged in the same manner, except that the current value in the constant-current discharging was changed to 30 mA corresponding to 5 C. After this output test, a discharge curve obtained at a current value of 30 mA corresponding to 5 C was examined. In this discharge curve, the time was plotted on the abscissa and the battery voltage was plotted on the ordinate.

An evaluation of "G (Al foil corrosion: absent)" was given when no abnormality was observed in the fluctuation of the battery voltage plotted on the ordinate of the discharge curve, while an evaluation of "B (Al foil corrosion: present)" was given when an erratic up and down abnormality was observed in the fluctuation of the battery voltage. The thus obtained evaluation results are shown in Table 7.

TABLE 7

| | Electrolyte solution No. | Output test (Al foil corrosion) |
| --- | --- | --- |
| Example II-12 | T12 | G |
| Comparative Example II-6 | T13 | B |

An abnormal fluctuation of the battery voltage occurred due to corrosion of the Al foil in Comparative Example II-6 where only LiFSI was contained in the electrolyte solution without $LiPF_6$; however, no abnormal fluctuation of the battery voltage occurred in Example II-12 where both $LiPF_6$ and LiFSI were contained in the electrolyte solution. From these results, it was found desirable that a non-aqueous electrolyte solution contains both $LiPF_6$ and LiFSI as lithium salts.

(4) −10° C. Cycle Test
(4-1) Production of Single-Layer Laminate-Type Non-Aqueous Secondary Batteries
(4-1-1) Production of Lead-Attached Positive Electrode (II-P2)

A composite oxide ($LiNi_{0.5}Mn_{0.3}Co_{0.2}O_2$) of lithium, nickel, manganese and cobalt as a positive electrode active material, an acetylene black powder as a conductive aid, and polyvinylidene fluoride (PVDF) as a binder were mixed at a weight ratio of 100:3.5:3 to obtain a positive electrode mixture.

To the thus obtained positive electrode mixture, N-methyl-2-pyrrolidone was added as a solvent, and the resultant was further mixed to prepare a positive electrode mixture-containing slurry. One side of a 15 μm-thick aluminum foil serving as a positive electrode current collector was coated with the positive electrode mixture-containing slurry while adjusting the basis weight of the slurry to be 9.50 mg/cm². When the aluminum foil was coated with the positive electrode mixture-containing slurry, an uncoated region was formed such that a portion of the aluminum foil was exposed. Thereafter, this aluminum foil was rolled using a roll press such that the resulting positive electrode active material layer had a density of 2.74 g/cm³, whereby a positive electrode composed of the positive electrode active material layer and the positive electrode current collector was obtained.

Next, this positive electrode was cut such that the positive electrode mixture layer had an area of 30 mm×50 mm and included the exposed portion of the aluminum foil. Subsequently, an aluminum-made lead piece for current extraction was welded to the exposed portion of the aluminum foil, and the resultant was vacuum-dried at 120° C. for 12 hours, whereby a lead-attached positive electrode (II-P2) was obtained.

(4-1-2) Production of Lead-Attached Negative Electrode (II-N2)

A graphite powder as a negative electrode active material was mixed with carboxymethyl cellulose and styrene-butadiene latex as binders at a weight ratio of 100:1.1:1.5 to obtain a negative electrode mixture.

To the thus obtained negative electrode mixture, water was added as a solvent, and the resultant was further mixed to prepare a negative electrode mixture-containing slurry. One side of a 10 μm-thick copper foil serving as a negative electrode current collector was coated with the negative electrode mixture-containing slurry while adjusting the basis weight of the slurry to be 6.10 mg/cm². When the copper foil was coated with the negative electrode mixture-containing slurry, an uncoated region was formed such that a portion of the copper foil was exposed. Thereafter, this copper foil was rolled using a roll press such that the resulting negative electrode active material layer had a density of 1.20 g/cm³, whereby a negative electrode composed of the negative electrode active material layer and the negative electrode current collector was obtained.

Next, this negative electrode was cut such that the negative electrode mixture layer had an area of 32 mm×52 mm and included the exposed portion of the copper foil. Subsequently, a nickel-made lead piece for current extraction was welded to the exposed portion of the copper foil, and the resultant was vacuum-dried at 80° C. for 12 hours, whereby a lead-attached negative electrode (II-N2) was obtained.

(4-1-3) Assembly of Single-Layer Laminate-Type Non-Aqueous Secondary Batteries

A laminated electrode structure was obtained by superimposing the lead-attached positive electrode (II-P2) and the lead-attached negative electrode (II-N2), which were obtained in the above-described manner, via a polyethylene microporous membrane separator (thickness=21 μm) such that the mixture-coated surfaces of these electrodes faced each other. This laminated electrode structure was placed in a 90 mm×80 mm aluminum laminate sheet exterior and vacuum-dried at 80° C. for 5 hours so as to remove moisture. Subsequently, a non-aqueous electrolyte solution shown in Table 5 above was injected into the exterior, and this exterior was sealed to produce single-layer laminate-type (pouch-type) non-aqueous secondary battery. The thus obtained single-layer laminate-type non-aqueous secondary battery had a design capacity value of 23 mAh and a rated voltage value of 4.2 V.

(4-2) Evaluation of Single-Layer Laminate-Type Non-Aqueous Secondary Batteries

For the single-layer laminate-type non-aqueous secondary batteries obtained in the above-described manner, first, an initial charging treatment was carried out in accordance with the procedures described below in (4-2-1). Next, each single-layer laminate-type non-aqueous secondary battery was evaluated in accordance with the procedures of (4-2-2). Charging and discharging were carried out using a charge-discharge device ACD-M01A (trade name) manufactured by Aska Electronic Co., Ltd. and a programmable incubator IN804 (trade name) manufactured by Yamato Scientific Co., Ltd.

It is noted here that "1 C" means a current value at which discharging of a battery in a fully-charged state is expected to be completed in one hour when the discharging is carried out at a constant current. In the below-described evaluations of (4-2-1) and (4-2-2), "1 C" specifically means a current value at which discharging of a battery from a fully-charged state of 4.2 V to 2.5 V at a constant current is expected to be completed in one hour.

(4-2-1) Initial Charge-Discharge Treatment of Single-Layer Laminate-Type Non-Aqueous Secondary Batteries The ambient temperature of each battery was set at 25° C., and the battery was charged to 4.2 V with a constant current of 2.3 mA corresponding to 0.1 C and then charged with a constant voltage of 4.2 V for a total of 1.5 hours. Subsequently, the battery was discharged to 2.5 V at a constant current of 6.9 mA corresponding to 0.3 C.

(4-2-2) −10° C. Cycle Test of Single-Layer Laminate-Type Non-Aqueous Secondary Batteries A cycle test was carried out for each battery on which an initial charge-discharge treatment had been carried out by the method described above in (4-2-1). The cycle test was started three hours after setting the ambient temperature of the battery at −10° C. First, the battery was charged to 4.2 V with a constant current of 4.6 mA corresponding to 0.2 C and then charged with a constant voltage of 4.2 V for a total of 3 hours. Subsequently, the battery was discharged to 2.5 V at a constant current of 4.6 mA. Defining this process of charging and discharging the battery once each as one cycle, 20 cycles of charging and discharging were carried out. The discharge capacity in the 20th cycle was calculated as −10° C. cycle capacity retention rate, taking the discharge capacity in the 1st cycle as 100%, and the thus obtained value was evaluated based on the following criteria.

Evaluation Criteria:

A: The capacity retention rate was 80% or higher.

B: The capacity retention rate was 70% or higher but lower than 80%.

C: The capacity retention rate was lower than 70%.

The −10° C. cycle capacity retention rate serves as an index of battery deterioration in the long-term use at a low temperature. The larger the value thereof, the smaller the reduction in the capacity caused by the long-term use at a low temperature, and it is believed that such a battery can be used in an application where the battery is intended to be used over a long period in a cold region. Accordingly, the −10° C. cycle capacity retention rate is desirably 70% or higher, more desirably 80% or higher.

The thus obtained evaluation results are shown in Table 8.

TABLE 8

| | Electrolyte solution No. | −10° C. cycle capacity retention rate |
|---|---|---|
| Example II-13 | T12 | A |
| Comparative Example II-7 | T14 | C |
| Comparative Example II-8 | T11 | C |

The −10° C. cycle capacity retention rate was lower than 70% in Comparative Example II-7 where the molar concentrations of lithium salts were $LiPF_6$>LiFSI and Comparative Example II-8 where the electrolyte solution contained only $LiPF_6$ without LiFSI; however, in Example II-13, the −10° C. cycle capacity retention rate was 80% or higher. From these results, it was found desirable to incorporate $LiPF_6$ and a LiFSI-containing imide salt as lithium salts at molar concentrations satisfying 0<$LiPF_6$≤imide salt.

(5) 50° C. Cycle Test of Coin-Type Non-Aqueous Secondary Batteries (5-1) Production of Coin-Type Non-Aqueous Secondary Batteries (5-1-1) Production of Positive Electrode (II-P3)

A composite oxide ($LiNi_{0.8}Mn_{0.1}Co_{0.1}O_2$) of lithium, nickel, manganese and cobalt as a positive electrode active material, a carbon black powder as a conductive aid, and polyvinylidene fluoride (PVDF) as a binder were mixed at a weight ratio of 94:3:3 to obtain a positive electrode mixture.

To the thus obtained positive electrode mixture, N-methyl-2-pyrrolidone was added as a solvent, and the resultant was further mixed to prepare a positive electrode mixture-containing slurry. One side of a 20 μm-thick aluminum foil serving as a positive electrode current collector was coated with the positive electrode mixture-containing slurry while adjusting the basis weight of the slurry to be 16.6 mg/cm$^2$, and the solvent was subsequently removed by drying. Thereafter, this aluminum foil was rolled using a roll press such that the resulting positive electrode active material layer had a density of 2.91 g/cm$^3$, whereby a positive electrode (II-P3) composed of the positive electrode active material layer and the positive electrode current collector was obtained.

(5-1-2) Production of Negative Electrode (II-N3)

A graphite powder as a negative electrode active material, a carbon black powder as a conductive aid, and polyvinylidene fluoride (PVDF) as a binder were mixed at a weight ratio of 90:3:7 to obtain a negative electrode mixture.

To the thus obtained negative electrode mixture, water was added as a solvent, and the resultant was further mixed to prepare a negative electrode mixture-containing slurry. One side of an 8 μm-thick copper foil serving as a negative electrode current collector was coated with the negative electrode mixture-containing slurry while adjusting the basis weight of the slurry to be 10.3 mg/cm$^2$, and the solvent was subsequently removed by drying. Thereafter, this copper foil was rolled using a roll press such that the resulting negative electrode active material layer had a density of 1.36 g/cm$^3$, whereby a negative electrode (II-N3) composed of the negative electrode active material layer and the negative electrode current collector was obtained.

(5-1-3) Assembly of Coin-Type Non-aqueous Secondary Batteries

A polypropylene gasket was set in a CR2032-type battery casing (SUS304/Al-clad), and the positive electrode (II-P3) obtained in the above-described manner was punched into a disk shape having a diameter of 15.958 mm and set in the center of the gasket with the positive electrode active material layer facing upward. A glass fiber filter paper (GA-100, manufactured by Advantec Co., Ltd.) punched into a disk shape having a diameter of 16.156 mm was set thereon, and 150 μL of a non-aqueous electrolyte solution was injected, after which the negative electrode (II-N3) obtained in the above-described manner was punched into a disk shape having a diameter of 16.156 mm and set with the negative electrode active material layer facing downward. Further, a spacer and a spring were set in the battery casing, and a battery cap was subsequently fitted and crimped using a caulking machine. The overflowed non-aqueous electrolyte solution was wiped off with a waste cloth. The resulting assembly, which contained a layered product of the II-P3, the glass fiber filter paper and the II-N3 along with the non-aqueous electrolyte solution, was maintained at a temperature of 25° C. for 12 hours to allow the non-aqueous electrolyte solution to thoroughly impregnate into the layered product, whereby a coin-type non-aqueous secondary battery was obtained.

(5-2) Evaluation of Coin-Type Non-Aqueous Secondary Batteries

For the coin-type non-aqueous secondary batteries obtained in the above-described manner, first, an initial charging treatment was carried out and the initial charge-discharge capacity was measured in accordance with the procedures described below in (5-2-1). Next, each non-aqueous secondary battery was evaluated in accordance with the procedures described below in (5-2-2). Charging and discharging were carried out using a charge-discharge device ACD-M01A (trade name) manufactured by Aska Electronic Co., Ltd. and a programmable incubator IN804 (trade name) manufactured by Yamato Scientific Co., Ltd.

It is noted here that "1 C" means a current value at which discharging of a battery in a fully-charged state is expected to be completed in one hour when the discharging is carried out at a constant current. In the below-described evaluations of (5-2-1) and (5-2-2), "1 C" specifically means a current value at which discharging of a battery from a fully-charged state of 4.2 V to 3.0 V at a constant current is expected to be completed in one hour.

In Examples according to the second embodiment, the current value corresponding to 1 C for each coin-type non-aqueous secondary battery is 6 mA.

(5-2-1) Initial Charge-Discharge Treatment

The ambient temperature of each coin-type non-aqueous secondary battery was set at 25° C., and the battery was charged to 3.1 V with a constant current of 0.15 mA corresponding to 0.025 C and then charged with a constant voltage of 3.1 V for 1.5 hours. After a subsequent 3-hour rest, the battery was charged to 4.2 V with a constant current of 0.3 mA corresponding to 0.05 C and then charged with a constant voltage of 4.2 V for 1.5 hours. Thereafter, the battery was discharged to 3.0 V at a constant current of 0.9 mA corresponding to 0.15 C. The discharge capacity in this process was defined as initial discharge capacity (X).

(5-2-2) 50° C. Cycle Test

For each coin-type non-aqueous secondary battery on which an initial charge-discharge treatment had been carried out by the method described above in (5-2-1), the ambient temperature was set at 50° C. and, after the battery was charged to 4.2 V with a constant current of 6 mA corresponding to 1 C, the battery was further charged with a constant voltage of 4.2 V for 1.5 hours. Subsequently, the battery was discharged to 3.0 V at a current value of 1.8 mA corresponding to 0.3 C. Next, the battery was charged with a constant current of 9 mA corresponding to 1.5 C and then charged until the battery voltage reached 4.2 V, after which the battery was charged with a constant current of 4.2 V for 1.5 hours. Subsequently, the battery was discharged to a battery voltage of 3.0 V at a constant current of 9 mA corresponding to 1.5 C. Defining this process of charging and discharging the battery once each as one cycle, 98 cycles of charging and discharging were carried out. Thereafter, the battery was charged to 4.2 V with a constant current of 6 mA corresponding to 1 C and then charged with a constant voltage of 4.2 V for 1.5 hours, after which the battery was discharged to 3.0 V at a current value of 1.8 mA corresponding to 0.3 C. The discharge capacity at this point was defined as 100th-cycle discharge capacity (hereinafter, may be denoted as "(T)"). The 50° C. cycle capacity retention rate was calculated based on the following equation:

50° C. cycle capacity retention rate=(100th-cycle discharge capacity (T) in 50° C. cycle test/Initial discharge capacity (X) in initial charge-discharge treatment)×100 [%]

The 50° C. cycle capacity retention rate serves as an index of battery deterioration caused by repeated use. The larger the value thereof, the smaller the reduction in the capacity caused by repeated use, and it is believed that such a battery can be used in an application where the battery is intended to be used over a long period.

In addition, the 50° C. cycle capacity retention rate can serve as an index of the extent of self-discharge at a high temperature. The larger the value thereof, the smaller the amount of self-discharge under a high temperature, and it is believed that such a battery can be used in an application intended to extract a greater amount of current from the battery.

Accordingly, the 50° C. cycle capacity retention rate is desirably 70% or higher, more desirably 80% or higher.

The thus obtained evaluation results are shown in Table 9.

TABLE 9

| | Electrolyte solution No. | 50° C. cycle capacity retention rate [%] |
|---|---|---|
| Example II-14 | T01 | 83.2 |
| Example II-15 | T02 | 80.9 |
| Example II-16 | T03 | 81.5 |
| Comparative Example II-9 | T15 | 79.5 |
| Comparative Example II-10 | T16 | 65.9 |
| Comparative Example II-11 | T17 | 66.1 |

The battery of Comparative Example II-9 containing no dinitrile compound exhibited a lower 50° C. cycle capacity retention rate than the batteries of Examples II-14 to II-16. In addition, in Comparative Examples II-10 and II-11 where the content of a dinitrile compound was less than 0.10 in terms of molar ratio with respect to the content of acetonitrile, the 50° C. cycle capacity retention rate was lower than 70%. From these results, it was found desirable to control the content of a dinitrile compound to be in a prescribed range.

(6) 50° C. Cycle Test of Small-Sized Non-Aqueous Secondary Batteries (6-1) Production of Small-Sized Non-Aqueous Secondary Batteries (6-1-1) Production of Positive Electrode (II-P4)

A composite oxide ($LiNi_{0.5}Mn_{0.3}Co_{0.2}O_2$) of lithium, nickel, manganese and cobalt as a positive electrode active material, a carbon black powder as a conductive aid, and polyvinylidene fluoride (PVDF) as a binder were mixed at a weight ratio of 94:3:3 to obtain a positive electrode mixture.

To the thus obtained positive electrode mixture, N-methyl-2-pyrrolidone was added as a solvent, and the resultant was further mixed to prepare a positive electrode mixture-containing slurry. One side of a 20 μm-thick aluminum foil serving as a positive electrode current collector was coated with the positive electrode mixture-containing slurry while adjusting the basis weight of the slurry to be 20.4 mg/cm$^2$, and the solvent was subsequently removed by drying. Thereafter, this aluminum foil was rolled using a roll press such that the resulting positive electrode active material layer had a density of 2.90 g/cm$^3$, whereby a positive electrode (II-P4) composed of the positive electrode active material layer and the positive electrode current collector was obtained.

(6-1-2) Production of Positive Electrode (II-P5)

A composite oxide ($LiNi_{0.6}Mn_{0.2}Co_{0.2}O_2$) of lithium, nickel, manganese and cobalt as a positive electrode active material, a carbon black powder as a conductive aid, and polyvinylidene fluoride (PVDF) as a binder were mixed at a weight ratio of 94:3:3 to obtain a positive electrode mixture.

To the thus obtained positive electrode mixture, N-methyl-2-pyrrolidone was added as a solvent, and the resultant was further mixed to prepare a positive electrode mixture-containing slurry. One side of a 20 μm-thick aluminum foil serving as a positive electrode current collector was coated with the positive electrode mixture-containing slurry while adjusting the basis weight of the slurry to be 19.7 mg/cm$^2$, and the solvent was subsequently removed by drying. Thereafter, this aluminum foil was rolled using a roll press such that the resulting positive electrode active material layer had a density of 2.90 g/cm$^3$, whereby a positive electrode (II-P5) composed of the positive electrode active material layer and the positive electrode current collector was obtained.

(6-1-3) Assembly of Small-Sized Non-Aqueous Secondary Batteries

The positive electrode (any of II-P3 to II-P5) obtained in the above-described manner that had been punched into a disk shape of 15.958 mm in diameter and the negative electrode (II-N3) obtained by the method described in (5-1-2) that had been punched into a disk shape of 16.156 mm in diameter were superimposed on the respective sides of a polyethylene microporous membrane separator (membrane thickness: 21 air permeability: 285 s/100 cm$^3$, porosity: 41%) to obtain a layered product. This layered product was inserted into an SUS-made disk-shaped battery casing. Subsequently, 2004 of a non-aqueous electrolyte solution (any of T18 to T25) was injected into the battery casing to immerse the layered product in the non-aqueous electrolyte solution, after which the battery casing was tightly sealed and maintained at 25° C. for 12 hours to allow the non-aqueous electrolyte solution to thoroughly impregnate into the layered product, whereby a small-sized non-aqueous secondary battery was obtained. Table 10 lists the combinations of positive electrode, negative electrode, and electrolyte solution in the thus obtained cells.

TABLE 10

| Cell No. | Positive electrode No. | Negative electrode No. | Electrolyte solution No. |
|---|---|---|---|
| C1 | II-P3 | II-N3 | T18 |
| C2 | II-P3 | II-N3 | T19 |
| C3 | II-P3 | II-N3 | T20 |
| C4 | II-P4 | II-N3 | T18 |
| C5 | II-P4 | II-N3 | T21 |
| C6 | II-P5 | II-N3 | T23 |
| C7 | II-P5 | II-N3 | T24 |
| C8 | II-P5 | II-N3 | T25 |
| C9 | II-P3 | II-N3 | T22 |
| C10 | II-P4 | II-N3 | T22 |

(6-2) Evaluation of Small-Sized Non-Aqueous Secondary Batteries

For the small-sized non-aqueous secondary batteries (C1 to C10) obtained in the above-described manner, first, an initial charging treatment was carried out and the initial charge-discharge capacity was measured in accordance with the procedures described below in (6-2-1). Next, each non-aqueous secondary battery was evaluated in accordance with the procedures described below in (6-2-2). Charging and discharging were carried out using a charge-discharge device ACD-M01A (trade name) manufactured by Aska Electronic Co., Ltd. and a programmable incubator IN804 (trade name) manufactured by Yamato Scientific Co., Ltd.

It is noted here that "1 C" means a current value at which discharging of a battery in a fully-charged state is expected to be completed in one hour when the discharging is carried out at a constant current. In the below-described evaluations of (6-2-1) and (6-2-2), "1 C" specifically means a current value at which discharging of a battery from a fully-charged state of 4.2 V to 3.0 V at a constant current is expected to be completed in one hour.

In Examples according to the second embodiment, the current value corresponding to 1 C for each small-sized non-aqueous secondary battery is 6 mA.

(6-2-1) Initial Charge-Discharge Treatment

The ambient temperature of each small-sized non-aqueous secondary battery was set at 25° C., and the battery was charged to 3.1 V with a constant current of 0.15 mA corresponding to 0.025 C and then charged with a constant voltage of 3.1 V for 1.5 hours. After a subsequent 3-hour rest, the battery was charged to 4.2 V with a constant current of 0.3 mA corresponding to 0.05 C and then charged with a constant voltage of 4.2 V for 1.5 hours. Thereafter, the battery was discharged to 3.0 V at a constant current of 0.9 mA corresponding to 0.15 C. The discharge capacity in this process was defined as initial discharge capacity (X).

(6-2-2) 50° C. Cycle Test

For each small-sized non-aqueous secondary battery on which an initial charge-discharge treatment had been carried out by the method described above in (6-2-1), the ambient temperature was set at 50° C. and, after the battery was charged to 4.2 V with a constant current of 6 mA corresponding to 1 C, the battery was further charged with a constant voltage of 4.2 V until the current value was reduced to 0.025 C. Subsequently, the battery was discharged to 3.0 V at a current value of 1.8 mA corresponding to 0.3 C. Next, the battery was charged with a constant current of 9 mA corresponding to 1.5 C and then charged until the battery voltage reached 4.2 V, after which the battery was charged with a constant current of 4.2 V until the current value was reduced to 0.025 C. Subsequently, the battery was discharged to a battery voltage of 3.0 V at a constant current of 9 mA corresponding to 1.5 C. Defining this process of charging and discharging the battery once each as one cycle, further 98 cycles of charging and discharging were carried out. Thereafter, the battery was charged to 4.2 V with a constant current of 6 mA corresponding to 1 C and then charged with a constant voltage of 4.2 V until the current value was reduced to 0.025 C, after which the battery was discharged to 3.0 V at a current value of 1.8 mA corresponding to 0.3 C. The discharge capacity at this point was defined as 100th-cycle discharge capacity (hereinafter, may be denoted as "(T)"). The 50° C. cycle capacity retention rate was calculated based on the following equation:

50° C. cycle capacity retention rate=(100th-cycle discharge capacity (T) in 50° C. cycle test/Initial discharge capacity (X) in initial charge-discharge treatment)×100 [%]

The 50° C. cycle capacity retention rate serves as an index of battery deterioration caused by repeated use. The larger the value thereof, the smaller the reduction in the capacity caused by repeated use, and it is believed that such a battery can be used in an application where the battery is intended to be used over a long period.

In addition, the 50° C. cycle capacity retention rate can serve as an index of the extent of self-discharge at a high temperature. The larger the value thereof, the smaller the amount of self-discharge under a high temperature, and it is believed that such a battery can be used in an application intended to extract a greater amount of current from the battery.

Accordingly, the 50° C. cycle capacity retention rate is desirably 80% or higher. The evaluation results obtained for the small-sized non-aqueous secondary batteries (C1 to C8) are shown in Table 11.

(6-3) Measurement of Alternating-Current (AC) Impedance after Rearrangement of Electrodes Two of each of the small-sized non-aqueous secondary batteries (C1 to C10) on which a 50° C. cycle test had been carried out by the method described above in (6-2-2) were prepared.

For these two small-sized non-aqueous secondary batteries, the ambient temperature was set at 25° C., and the batteries were charged to 4.0 V with a constant current of 3 mA corresponding to 0.5 C and then charged with a constant voltage of 4.0 V until the current value was reduced to 0.025 C. Subsequently, the two small-sized non-aqueous secondary batteries were disassembled in an argon atmosphere to take out the two positive electrodes and the two negative electrodes. Thereafter, the thus recovered two positive electrodes were superimposed on the respective sides of a polyethylene microporous membrane separator (membrane thickness: 21 win, air permeability: 285 s/100 cm$^3$, porosity: 41%) to obtain a layered product. This layered product was inserted into an SUS-made disk-shaped battery casing. Subsequently, 200 μL of a non-aqueous electrolyte solution shown in Table 10 was injected into the battery casing to immerse the layered product in the non-aqueous electrolyte solution, after which the battery casing was tightly sealed and maintained at 25° C. for 12 hours to allow the non-aqueous electrolyte solution to thoroughly impregnate into the layered product, whereby a positive electrode-facing cell was obtained. Further, by the same operations, a negative electrode-facing cell was obtained using the two negative electrodes recovered after the disassembly.

For the positive electrode-facing cell and the negative electrode-facing cell that were obtained in the above-described manner, the AC impedance was measured. For the measurement, FREQUENCY RESPONSE ANALYZER 1400 (trade name) manufactured by Solartron Metrology Co., Ltd. and POTENTIO-GALVANOSTAT 1470E (trade name) manufactured by Solartron Metrology Co., Ltd. were employed. AC signals were applied while changing the frequency in 1,000 kHz to 0.01 Hz, and the impedance was measured from the voltage-current response signals to determine the AC impedance values. A Nyquist diagram was prepared by plotting the thus obtained AC impedance values with the real part (Z') of the impedance being on the abscissa and the imaginary part (Z") of the impedance being on the ordinate. The amplitude of the applied AC voltage was set at ±5 mV, and the battery ambient temperature during the measurement of the AC impedance was set at 25° C.

Figure 5:
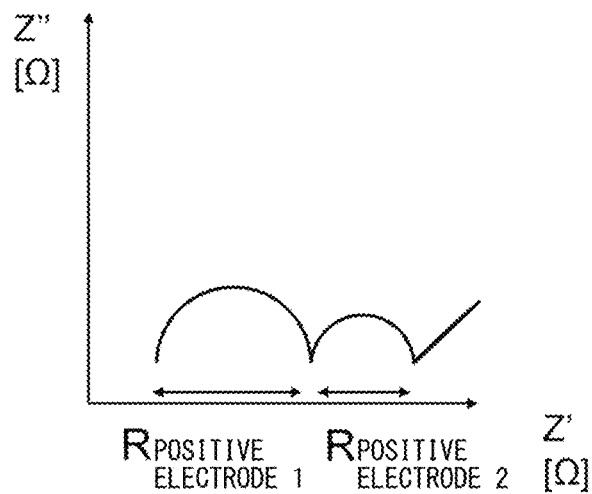
FIG. 5 is one example of a Nyquist plot of a positive electrode-facing cell.
Figure 6:
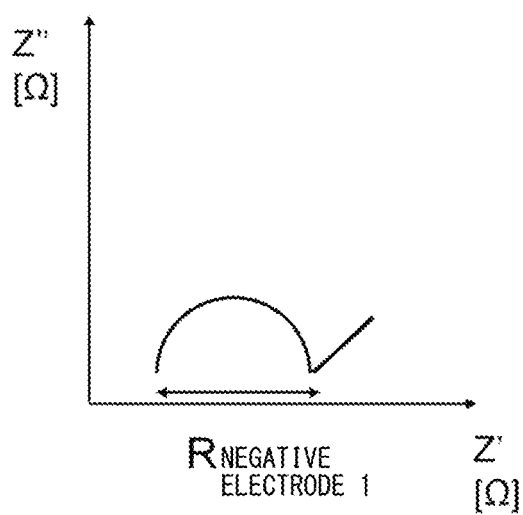
FIG. 6 is one example of a Nyquist plot of a negative electrode-facing cell.

In the present embodiment, the Nyquist plot of the positive electrode-facing cell and that of the negative electrode-facing cell are provided in FIG. 5 and FIG. 6, respectively.

In FIG. 5, a plot at 1,000 kHz is defined as "A1" and, among those plots giving inflection points at which the absolute value of the imaginary part of the impedance shifts from decreasing to increasing, a plot with the highest frequency is defined as "A2" and a plot with the second highest frequency is defined as "A3". The difference between the real part of A2 and that of A1 is defined as "$R_{positive\ electrode\ 1}$", and the difference between the real part of A3 and that of A2 is defined as "$R_{positive\ electrode\ 2}$". In FIG. 5, the $R_{positive\ electrode\ 1}$ and the $R_{positive\ electrode\ 2}$ of the positive electrode-facing cell each correspond to the interfacial resistance component of the positive electrodes. Smaller values thereof are believed to indicate further inhibition of an increase in the interfacial resistance component of the positive electrodes in the 50° C. cycle test.

Further, in FIG. 6, a plot at 1,000 kHz is defined as "B1" and, among those plots giving inflection points at which the absolute value of the imaginary part of the impedance shifts from decreasing to increasing, a plot with the highest frequency is defined as "B2". The difference between the real part of B2 and that of B1 is defined as "$R_{negative\ electrode\ 1}$". The $R_{negative\ electrode\ 1}$ of the negative electrode-facing cell corresponds to the interfacial resistance component of the negative electrodes. A smaller value thereof is believed to indicate further inhibition of an increase in the interfacial resistance component of the negative electrodes in the 50° C. cycle test.

Next, for each of cells (C1 to C8), the rate of increase in the positive electrode interfacial resistance and the rate of increase in the negative electrode interfacial resistance, which increases are caused by an addition of a dinitrile compound to the respective non-aqueous electrolyte solutions, were calculated using the following equations. The dinitrile compound-free cells corresponding to the respective small-sized non-aqueous secondary batteries are shown in Table 11.

Rate of increase in positive electrode interfacial resistance=($R_{positive\ electrode\ 2}$ of each cell)/($R_{positive\ electrode\ 2}$ of dinitrile compound-free cell corresponding to each cell)

Rate of increase in negative electrode interfacial resistance=($R_{negative\ electrode\ 1}$ of each cell)/($R_{negative\ electrode\ 1}$ of dinitrile compound-free cell corresponding to each cell)

The rate of increase in the positive electrode interfacial resistance corresponds to the rate of increase in the interfacial resistance component of the positive electrodes caused by an addition of a dinitrile compound. When this value is smaller than 1, it is believed that the addition of the dinitrile compound inhibited an increase in the interfacial resistance component of the positive electrodes in the 50° C. cycle test.

The rate of increase in the negative electrode interfacial resistance corresponds to the rate of increase in the interfacial resistance component of the negative electrodes caused by an addition of a dinitrile compound. When this value is smaller than 1, it is believed that the addition of the dinitrile compound inhibited an increase in the interfacial resistance component of the negative electrodes in the 50° C. cycle test.

The thus obtained evaluation results are shown in Table 11.

TABLE 11

| Cell No. | 50° C. cycle capacity retention rate [%] | Corresponding dinitrile compound-free cell No. | Rate of increase in positive electrode interfacial resistance [times] | Rate of increase in negative electrode interfacial resistance [times] |
|---|---|---|---|---|
| Example II-17 | C1 | 88.1 | C9 | 0.51 | 0.91 |
| Example II-18 | C2 | 81.4 | C3 | 0.42 | 0.86 |
| Comparative Example II-12 | C3 | 79.3 | C3 | 1 | 1 |
| Example II-19 | C4 | 90.4 | C10 | 0.45 | 0.92 |
| Example II-20 | C5 | 90.9 | C10 | 0.41 | 0.89 |
| Example II-21 | C6 | 80.4 | C8 | 0.44 | 0.95 |
| Example II-22 | C7 | 81.2 | C8 | 0.42 | 0.93 |
| Comparative Example II-13 | C8 | 75.4 | C8 | 1 | 1 |

The capacity retention rate in the 50° C. cycle test was lower than 80% in Comparative Examples II-12 and II-13 where a dinitrile compound was not incorporated, while the capacity retention rate in the 50° C. cycle test was 80% or higher in Examples II-17 to II-22; therefore, it was indicated that the high-temperature durability is improved by controlling the content of a dinitrile compound to be in a prescribed range.

Further, comparing Examples II-17 to II-22 with Comparative Examples II-12 and II-13, the values of the rate of increase in the positive electrode interfacial resistance and the rate of increase in the negative electrode interfacial resistance were both controlled to be smaller than 1 by controlling the content of a dinitrile compound to be in a prescribed range. This is presumed to be because not only cracking of the particles contained in the positive electrode active material was inhibited by the dinitrile compound and an increase in the positive electrode interfacial resistance was thereby inhibited, but also a damage to the negative electrode SEI caused by reduction and precipitation of a metal eluted from the positive electrode on the negative electrode was inhibited and an increase in the negative electrode interfacial resistance was thereby inhibited.

INDUSTRIAL APPLICABILITY

The non-aqueous secondary battery of the present invention is expected to be utilized as, for example, rechargeable batteries for portable devices, such as mobile phones, portable audio devices, personal computers, and integrated circuit (IC) tags; automotive rechargeable batteries of hybrid vehicles, plug-in hybrid vehicles, and electric vehicles; low-voltage power sources, such as 12-V power sources, 24-V power sources, and 48-V power sources; residential power storage systems; and IoT devices. Moreover, the non-aqueous secondary battery of the present invention can also be utilized in cold climate applications, summer outdoor applications and the like.

REFERENCE SIGNS LIST

100: non-aqueous secondary battery
110: battery exterior
120: space of battery exterior 110
130: positive electrode lead
140: negative electrode lead
150: positive electrode
160: negative electrode
170: separator

The invention claimed is:
1. A non-aqueous secondary battery, comprising:
a positive electrode that comprises a positive electrode active material;
a negative electrode that comprises a negative electrode active material;
a separator; and
a non-aqueous electrolyte solution,
wherein
the positive electrode active material comprises:
a lithium-containing metal oxide represented by the following Formula (a):

$$Li_pNi_qCo_rM^1{}_sM^2{}_tO_u \quad (a)$$

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0<t<0.3$, $0.7 \leq q+r+s+t \leq 1.2$, and $1.8<u<2.2$ are satisfied; and p is a value determined by a charge-discharge state of the battery},
or
a positive electrode active material composite formed of:
a core particle containing a lithium-containing metal oxide represented by the following Formula (b):

$$Li_pNi_qCo_rM^1{}_sM^2{}_tO_u \quad (b)$$

{wherein, $M^1$ represents at least one element selected from the group consisting of Mn and Al; $M^2$ represents at least one element selected from the group consisting of Fe, Cu, Nb, Mo, Ti, Cr, Zr, Zn, Na, K, Ca, Mg, Pt, Au, B, P, Eu, Sm, W, Ce, V, Ba, Ta, Sn, Hf, Gd, and Nd; ranges of $0<p<1.3$, $0.5<q<1$, $0<r<0.3$, $0<s<0.3$, $0 \leq t<0.3$, $0.7 \leq q+r+s+t \leq 1.2$, and $1.8<u<2.2$ are satisfied; and p is a value determined by a charge-discharge state of the battery}; and
a coating layer that exists on at least one portion of a surface of the core particle and contains at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd,
in a step 1 of constant-current charging the non-aqueous secondary battery to a battery voltage of 4.2 V under a 25° C. environment and subsequently constant-voltage charging the battery to a current value of 0.025 C followed by discharging to 3 V at a constant current, and a step 2 of, after the step 1, carrying out 100 cycles each of which consists of constant-current charging the non-aqueous secondary battery to a battery voltage of 4.2 V under a 50° C. environment and subsequently constant-voltage charging the battery to a current value of 0.025 C followed by discharging to 3 V at a constant current, when a c-axis lattice constant determined by an analysis of the positive electrode of the non-aqueous secondary battery based on powder X-ray diffraction using Cu-Kα radiation before the step 1 is defined as c1, while a c-axis lattice constant determined by an analysis of the positive electrode of the non-aqueous secondary battery based on powder X-ray diffraction using Cu-Kα radiation after constant-current discharging of the battery to a battery voltage of 2.5 V under a 25° C. environment following the step 2 is defined as c2, a rate of change represented by the following equation:

$$\{(c2/c1)-1\} \times 100$$

is 1.0% or lower, the non-aqueous electrolyte solution contains acetonitrile in an amount of 5 to 20% by volume with respect to a total amount of a non-aqueous solvent, and the non-aqueous electrolyte solution has an ionic conductivity of 10 mS/cm or higher and lower than 15 mS/cm at 20° C.

2. The non-aqueous secondary battery according to claim 1, wherein the lithium-containing metal oxide further satisfies $0.7<q<1$, $0<r<0.2$, and $0<s<0.2$ in Formula (a) or (b).

3. The non-aqueous secondary battery according to claim 1, wherein the coating layer comprises an oxide of at least one element selected from the group consisting of Fe, Cu, Nb, Mo, Ti, Al, Cr, Zr, Zn, Na, K, Ca, Mg, Pt, Au, B, P, Eu, Sm, W, Ce, V, Ba, Ta, Sn, Hf, Gd, and Nd.

4. The non-aqueous secondary battery according to claim 3, wherein the coating layer comprises zirconium (Zr) oxide.

5. The non-aqueous secondary battery according to claim 2, wherein $M^2$ in Formula (a) or (b) comprises Zr.

6. A non-aqueous secondary battery, comprising:
a positive electrode that comprises a positive electrode active material;
a negative electrode that comprises a negative electrode active material;
a separator; and
a non-aqueous electrolyte solution,
wherein
the positive electrode comprises a lithium-containing metal oxide,
the lithium-containing metal oxide is represented by the following Formula (c):

$$LiNi_xCo_yMn_zO_2 \qquad (c)$$

{wherein, $0.5<x<1$, $0<y<0.3$, and $0<z<0.3$}, in a step 1 of constant-current charging the non-aqueous secondary battery to a battery voltage of 4.2 V under a 25° C. environment and subsequently constant-voltage charging the battery to a current value of 0.025 C followed by discharging to 3 V at a constant current, and a step 2 of, after the step 1, carrying out 100 cycles each of which consists of constant-current charging the non-aqueous secondary battery to a battery voltage of 4.2 V under a 50° C. environment and subsequently constant-voltage charging the battery to a current value of 0.025 C followed by discharging to 3 V at a constant current, when a c-axis lattice constant determined by an analysis of the positive electrode of the non-aqueous secondary battery based on powder X-ray diffraction using Cu-Koradiation before the step 1 is defined as c1, while a c-axis lattice constant determined by an analysis of the positive electrode of the non-aqueous secondary battery based on powder X-ray diffraction using Cu-Kα radiation after constant-current discharging of the battery to a battery voltage of 2.5 V under a 25° C. environment following the step 2 is defined as c2, a rate of change represented by the following equation:

$$\{(c2/c1)-1\} \times 100$$

is 1.0% or lower, the non-aqueous electrolyte solution contains acetonitrile in an amount of 5 to 20% by volume with respect to a total amount of a non-aqueous solvent, and the non-aqueous electrolyte solution has an ionic conductivity of 10 mS/cm or higher and lower than 15 mS/cm at 20° C.

7. The non-aqueous secondary battery according to claim 6, wherein the lithium-containing metal oxide further satisfies $0.7<x<0.9$, $0<y<0.2$, and $0<z<0.2$ in Formula (c).

8. The non-aqueous secondary battery according to claim 1, wherein the c1 is a c-axis lattice constant determined by an analysis of the positive electrode based on powder X-ray diffraction using Cu-Kα radiation before assembly of the non-aqueous secondary battery.

9. The non-aqueous secondary battery according to claim 1, wherein the rate of change in the c-axis is 0.6% or lower.

10. The non-aqueous secondary battery according to claim 1, wherein the non-aqueous electrolyte solution comprises no acid anhydride.

11. The non-aqueous secondary battery according to claim 1, wherein the non-aqueous electrolyte solution further comprises an imide salt.

12. The non-aqueous secondary battery according to claim 1, wherein the non-aqueous electrolyte solution further comprises a dinitrile compound represented by the following Formula (1):

[Chem. 1]

$$NC-R-CN \qquad (1)$$

{wherein, R represents a straight-chain or branched divalent aliphatic alkyl group having 1 to 12 carbon atoms and optionally containing oxygen atoms}, and the content of the dinitrile compound is 0.01 to 25% by weight with respect to the whole non-aqueous electrolyte solution.

13. The non-aqueous secondary battery according to claim 12, wherein the dinitrile compound is at least one compound selected from the group consisting of succinonitrile and methylsuccinonitrile.

14. The non-aqueous secondary battery according to claim 1, wherein the non-aqueous electrolyte solution comprises a compound represented by the following Formula (2):

[Chem. 2]

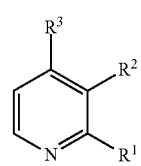

(2)

{wherein, substituents represented by $R^1$, $R^2$, and $R^3$ each independently represent a hydrogen atom, an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, a phenyl group, a cyclohexyl group, a nitrile group, a nitro group, an amino group, an N,N'-dimethylamino group, or an N,N'-diethylamino group; and at least two of the substituents are hydrogen atoms}, and the content of the compound represented by Formula (2) is 0.01 to 10% by weight with respect to the whole non-aqueous electrolyte solution.

15. The non-aqueous secondary battery according to claim 14, wherein the compound represented by Formula (2) is at least one compound selected from the group consisting of pyridine and 4-(tert-butyl) pyridine.

16. The non-aqueous secondary battery according to claim 1, wherein the $FSO_3$ anion content in the non-aqueous electrolyte solution is 100 ppm or less with respect to the non-aqueous electrolyte solution.

17. The non-aqueous secondary battery according to claim 1, wherein the c-axis lattice constants c1 and c2 are 14.3 Å or less.

18. The non-aqueous secondary battery according to claim 4, wherein the rate of change in the c-axis is 0.6% or lower, and the non-aqueous electrolyte solution comprises no acid anhydride.

19. The non-aqueous secondary battery according to claim 18, wherein the c1 is a c-axis lattice constant determined by an analysis of the positive electrode based on powder X-ray diffraction using Cu-Kα radiation before assembly of the non-aqueous secondary battery.

20. The non-aqueous secondary battery according to claim 5, wherein the rate of change in the c-axis is 0.6% or lower, and the non-aqueous electrolyte solution comprises no acid anhydride.

\* \* \* \* \*